US011693009B2

(12) United States Patent
Pimentel et al.

(10) Patent No.: US 11,693,009 B2
(45) Date of Patent: *Jul. 4, 2023

(54) METHODS FOR DETECTING POST-INFECTIOUS IRRITABLE BOWEL SYNDROME

(71) Applicant: Cedars-Sinai Medical Center, Los Angeles, CA (US)

(72) Inventors: Mark Pimentel, Los Angeles, CA (US); Christopher Chang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 16/877,230

(22) Filed: May 18, 2020

(65) Prior Publication Data

US 2020/0284804 A1   Sep. 10, 2020

Related U.S. Application Data

(63) Continuation-in-part of application No. 16/734,842, filed on Jan. 6, 2020, now abandoned, and a continuation-in-part of application No. 16/594,935, filed on Oct. 7, 2019, now abandoned, said application No. 16/734,842 is a continuation of application No. 16/185,955, filed on Nov. 9, 2018, now Pat. No. 10,527,621, application No. 16/877,230 is a continuation-in-part of application No. 16/152,806, filed on Oct. 5, 2018, now Pat. No. 10,690,679, said application No. 16/594,935 is a continuation of application No. 15/922,604, filed on Mar. 15, 2018, now Pat. No. 10,466,254, said application No. 16/185,955 is a continuation of application No. 15/855,792, filed on Dec. 27, 2017, now Pat. No. 10,151,752, said application No. 15/922,604 is a continuation of application No. 15/609,959, filed on May 31, 2017, now Pat. No. 9,952,223, said application No. 16/152,806 is a continuation of application No. 14/878,416, filed on Oct. 8, 2015, now Pat. No. 10,132,814, said application No. 15/855,792 is a continuation of application No. 14/793,523, filed on Jul. 7, 2015, now Pat. No. 9,869,676, said application No. 15/609,959 is a continuation of application No. 14/428,195, filed as application No. PCT/US2013/055626 on Aug. 19, 2013, now Pat. No. 9,702,884, said application No. 14/793,523 is a continuation of application No. 13/148,252, filed as application No. PCT/US2010/023911 on Feb. 11, 2010, now Pat. No. 9,110,081.

(60) Provisional application No. 62/085,825, filed on Dec. 1, 2014, provisional application No. 62/061,877, filed on Oct. 9, 2014, provisional application No. 61/762,632, filed on Feb. 8, 2013, provisional application No. 61/701,923, filed on Sep. 17, 2012, provisional application No. 61/286,250, filed on Dec. 14, 2009, provisional application No. 61/151,779, filed on Feb. 11, 2009.

(51) Int. Cl.
   G01N 33/68       (2006.01)

(52) U.S. Cl.
   CPC ... G01N 33/6854 (2013.01); *G01N 2333/205* (2013.01); *G01N 2800/065* (2013.01); *G01N 2800/52* (2013.01)

(58) Field of Classification Search
   CPC ......... G01N 33/6854; G01N 2333/205; G01N 2800/065; G01N 2800/52; G01N 33/56922; G01N 2469/20
   See application file for complete search history.

(56) References Cited

U.S. PATENT DOCUMENTS

| | | |
|---|---|---|
| 5,691,151 A | 11/1997 | Braun et al. |
| 6,805,852 B2 | 10/2004 | Lin et al. |
| 6,861,053 B1 | 3/2005 | Lin et al. |
| 7,048,906 B2 | 5/2006 | Lin et al. |
| 7,056,686 B2 | 6/2006 | Lin et al. |
| 7,081,239 B2 | 7/2006 | Lin |
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |

(Continued)

FOREIGN PATENT DOCUMENTS

| | | |
|---|---|---|
| AU | 2002256254 B2 | 5/2007 |
| AU | 2007201246 A1 | 3/2009 |

(Continued)

OTHER PUBLICATIONS

PCT/US2013/005626 International Search Report and Written Opinion dated Aug. 18, 2014; 14 pages.

(Continued)

*Primary Examiner* — Elly-Gerald Stoica
(74) *Attorney, Agent, or Firm* — Nixon Peabody LLP; Linda B. Huber

(57) ABSTRACT

Described herein are methods and systems for detecting and/or distinguishing irritable bowel syndrome (IBS) from inflammatory bowel disease (IBD) and celiac disease. The methods and systems can utilize the detection of anti-CdtB antibodies and/or anti-vinculin antibodies to detect IBS, distinguish IBS from IBD and/or celiac disease. Further described are methods for selecting a therapy to treat IBS, IBD or celiac disease.

18 Claims, 23 Drawing Sheets

Specification includes a Sequence Listing.

(56) References Cited

U.S. PATENT DOCUMENTS

| | | | |
|---|---|---|---|
| 7,608,245 B2 | 10/2009 | Lin | |
| 7,615,207 B2 | 11/2009 | Lin | |
| 7,718,608 B2 | 5/2010 | Lin et al. | |
| 7,736,622 B2 | 6/2010 | Lin et al. | |
| 7,935,799 B2 | 5/2011 | Lin et al. | |
| 8,110,177 B2 | 2/2012 | Lin et al. | |
| 8,197,805 B2 | 6/2012 | Lin et al. | |
| 8,388,935 B2 | 3/2013 | Lin et al. | |
| 8,562,952 B2 | 10/2013 | Lin et al. | |
| 9,110,081 B2 | 8/2015 | Pimentel et al. | |
| 9,358,276 B2 | 6/2016 | Lin et al. | |
| 9,702,884 B2 | 7/2017 | Pimentel et al. | |
| 9,851,361 B2 | 12/2017 | Pimentel | |
| 9,869,676 B2 | 1/2018 | Pimentel et al. | |
| 9,952,223 B2 | 4/2018 | Pimentel et al. | |
| 10,132,814 B2 | 11/2018 | Pimentel et al. | |
| 10,151,752 B2 | 12/2018 | Pimentel et al. | |
| 10,466,254 B2 | 11/2019 | Pimentel et al. | |
| 10,527,621 B2 | 1/2020 | Pimentel et al. | |
| 10,690,679 B2 | 6/2020 | Pimentel et al. | |
| 2003/0170726 A1 | 9/2003 | Fradelizi et al. | |
| 2004/0018528 A1 | 1/2004 | Morimoto et al. | |
| 2005/0014693 A1 | 1/2005 | Lin et al. | |
| 2006/0127359 A1 | 6/2006 | Borrelli | |
| 2006/0193871 A1 | 8/2006 | Lin | |
| 2006/0246085 A1 | 11/2006 | Lin et al. | |
| 2007/0142291 A1 | 6/2007 | Lin et al. | |
| 2007/0212691 A1* | 9/2007 | Yamasaki | C07K 14/205 435/69.3 |
| 2009/0298060 A1 | 12/2009 | Lal et al. | |
| 2011/0183337 A1 | 7/2011 | Von Stein et al. | |
| 2011/0294726 A1 | 12/2011 | Pimentel et al. | |
| 2012/0088257 A1 | 4/2012 | Mouthon et al. | |
| 2012/0263790 A1 | 10/2012 | Lin et al. | |
| 2013/0331283 A1 | 12/2013 | McAndrew et al. | |
| 2014/0206636 A1 | 7/2014 | Lin et al. | |
| 2015/0023394 A1 | 8/2015 | Pimentel et al. | |
| 2016/0103136 A1 | 4/2016 | Pimentel | |
| 2017/0095543 A1 | 4/2017 | Lin et al. | |
| 2018/0088130 A1 | 3/2018 | Pimentel et al. | |
| 2018/0196063 A1 | 7/2018 | Pimentel et al. | |
| 2018/0231551 A1 | 8/2018 | Pimentel et al. | |
| 2018/0364255 A1 | 12/2018 | Pimentel et al. | |
| 2020/0271665 A1 | 8/2020 | Pimentel et al. | |
| 2020/0284804 A1 | 9/2020 | Pimentel et al. | |
| 2021/0405046 A1 | 12/2021 | Pimentel et al. | |

FOREIGN PATENT DOCUMENTS

| | | |
|---|---|---|
| AU | 2010213708 B2 | 12/2015 |
| AU | 2014331841 A2 | 3/2016 |
| AU | 2015330872 A1 | 4/2017 |
| AU | 2016201529 | 6/2018 |
| AU | 2013315981 | 7/2019 |
| AU | 2014331841 | 6/2020 |
| AU | 2015330872 A1 | 8/2021 |
| BR | PI1008058-9 | 3/2016 |
| BR | 112016007474-2 A2 | 9/2017 |
| CA | 2923651 A1 | 4/2015 |
| CA | 2962493 A1 | 4/2016 |
| CA | 2444548 C | 6/2016 |
| CL | 1943-2011 | 2/2012 |
| CL | 2011-1944 | 2/2012 |
| CL | 2016000820 A1 | 9/2016 |
| CN | 105744956 A1 | 7/2016 |
| CN | 107003308 A | 8/2017 |
| CO | 16091069 | 9/2016 |
| DE | 602013027637.4 | 10/2017 |
| EP | 1 385 476 | 2/2004 |
| EP | 2 261 665 B1 | 6/2004 |
| EP | 1 200 828 B1 | 10/2007 |
| EP | 2 261 664 A2 | 12/2010 |
| EP | 2 305 213 A2 | 4/2011 |
| EP | 1 811 303 B1 | 6/2011 |
| EP | 2 256 498 B1 | 4/2015 |
| EP | 2 895 856 | 7/2015 |
| EP | 2 267 445 B1 | 8/2016 |
| EP | 3054977 A1 | 8/2016 |
| EP | 3204771 A1 | 8/2017 |
| EP | 2396652 | 12/2017 |
| EP | 3349004 | 7/2018 |
| EP | 1385476 B1 | 1/2021 |
| EP | 3054977 A1 | 7/2021 |
| HK | 1221898 | 3/2022 |
| IL | 251606 A | 12/2020 |
| IN | 201727012044 | 6/2017 |
| JP | 2009-102401 | 5/2009 |
| JP | 4653936 | 12/2010 |
| JP | 2017502253 A | 1/2017 |
| JP | 2017531801 | 10/2017 |
| JP | 6784669 | 11/2020 |
| KR | 20160062161 A | 6/2016 |
| KR | 20170067795 A | 6/2017 |
| KR | 102203568 | 1/2021 |
| KR | 102259588 B1 | 5/2021 |
| KR | 102426541 B1 | 7/2022 |
| MX | 2015-048142 | 7/2015 |
| MX | 2016004167 A | 6/2016 |
| MX | 348670 | 6/2017 |
| MX | 2017055077 | 7/2017 |
| MX | 2017-045632 | 11/2017 |
| NZ | 717633 A | 11/2021 |
| NZ | 730490 A | 11/2021 |
| PE | 08822016 A1 | 9/2016 |
| RU | 2397178 | 8/2010 |
| RU | 2397178 C1 | 8/2010 |
| RU | 2706361 C2 | 11/2019 |
| SG | 11201702395 | 4/2017 |
| SG | 11201601733 | 5/2018 |
| SG | 11201702395 | 3/2021 |
| WO | WO 01/11077 A2 | 2/2001 |
| WO | WO 01/11334 A2 | 2/2001 |
| WO | WO 2002/083926 A2 | 10/2002 |
| WO | WO 2004/024097 A2 | 3/2004 |
| WO | WO 2005/029091 | 3/2005 |
| WO | WO 2010/093801 A1 | 8/2010 |
| WO | WO 2012/007913 A2 | 1/2012 |
| WO | WO 2014/042828 A2 | 3/2014 |
| WO | WO 2015/054529 A1 | 4/2015 |
| WO | WO 2016/057772 A1 | 4/2016 |
| WO | WO 2018/140869 | 8/2018 |

OTHER PUBLICATIONS

PCT/US2013/005626 International Preliminary Report on Patentability dated Aug. 18, 2014; 12 pages.
PCT/US2010/023911 International Search Report and Written Opinion dated May 14, 2010; 11 pages.
PCT/US2010/023911 International Preliminary Report on Patentability dated Aug. 16, 2011; 8 pages.
PCT/US2014/059957 International Search Report and Written Opinion dated Jan. 8, 2015; 11 pages.
PCT/US2014/059957 International Preliminary Report on Patentability dated Apr. 21, 2016; 9 pages.
PCT/US2015/054655 International Search Report and Written Opinion dated Feb. 12, 2016; 7 pages.
International Search Report and Written Opinion of PCT/US2018/015723, dated Apr. 24, 2018, 13 Pages.
Extended European Search Report of EP 15 849701.6 dated Feb. 8, 2018, 10 Pages.
EP Application No. 17206465.1 Extended Search Report dated Apr. 20, 2018; 13 pages.
EP Application No. 10741728.9 Extended Search Report dated Oct. 17, 2014; 7 pages.
EP Application No. 13837424.4 Extended Search Report dated May 9, 2016; 8 pages.
Singapore Application No. 11201601733V Written Opinion dated Apr. 17, 2017; 8 pages.
Written Opinion of Singapore Application No. 11201702395W, dated Nov. 24, 2017, 8 pages.

(56) References Cited

OTHER PUBLICATIONS

Abuoun et al. Cytolethal Distending Toxin (CDT)-Negative Campylobacter jejuni Strains and Anti-CDT Neutralizing Antibodies are Induced during Human Infection but Not during Colonization in Chickens. Infection and Immunity (2005). 73(5): 3053-3062.
Air et al. Mechanism of Antigenic Variation in an Individual Epitope on Influenza Virus N9 Neuraminidase. Journal of Virology (1990), 64(12):5797-5803.
Bourke, B. Campylobacter infection: small bowel and colon. Current Opinion in Gastroenterology. (2002). 18:4-9.
Bradesi et al., Novel Therapeutic Approaches in IBS, Current Opinion in Pharmacology, 2007, vol. 7(6), pp. 598-604.
Cambridge et al. Anti-neutrophil antibodies in inflammatory bowel disease: prevalence and diagnostic role. Gut (2013). 33:668-674.
Carey et al. A prospective evaluation of the pathogenesis of detrusor instability in woman, using electron microscopy and immunohistochemistry. BJU International (2000). 86:970-976.
Colman, PM. Effects of amino acid sequence changes on antibody-antigen interactions. Res Immunol (1994). 145(1):33-6.
Dib et al., Targets of Anti-Endothelial Cell Antibodies in Pulmonary Hypertension and Scleroderma, 2012, Eur. Respir. J., vol. 39, pp. 1405-1414.
Dunlop et al. Relative Importance of Enterochromaffin Cell Hyperplasia, Anxiety, and Depression in Postinfectious IBS. Gastroenterology (2003), 125:1651-1659.
EP Application No. 14851688.3 Extended Search Report dated Mar. 10, 2017; 10 pages.
Fox et al. Gastroenteritis in NF-kappaB-deficient mice is produced with wildtype Camplyobacter jejuni but not with C. jejuni lacking cytolethal distending toxin despite persistent colonization with both strains. Infection & Immunity (2004). 72(2):1116-25,.
Hickey et al. Campylobacter jejuni Cytolethal Distending Toxin Mediates Release of Interleukin-8 from Intestinal Epithelial Cells. Infection and Immunity (2000). 68(12):6535-6541.
Lembo et al. Use of serum biomarkers in a diagnostic test for irritable bowel syndrome. Alimentary Pharmacology & Therapeutics (2009). 29:834-842.
Mariuzza et al. The structural basis of antigen-antibody recognition. Annu Rev Biophys Biophys Chem (1987). 16:139-59, Abstract Only.
Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.
Morales et al. Effect of Rifaximin Treatment on Anti-Vinculin Antibodies in IBS with Diarrhea. Gastroenterology (2016). 150(4). Supplement 1. p. S-695.
Morales et al. Tu2056 Antibodies to Cytolethal Distending Toxin B and Auto-Antibodies to Human Vinculin are Elevated in IBS Subjects. Gastroenterology (2013). 144(5): Suppl. 1, p. S-914.
Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.
Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.
Nelson et al. Vinculin Activators Target Integrins from within the Cell to Increase Melanoma Sensitivity to Chemotherapy. Molecular Cancer Research (2011). 9(6):1-12.
Nemeth et al. Altered Cytoskeleton in Smooth Muscle of Aganglionic Bowel. Arch Pathol Lab Med (2002). 126:692-696.
Novak, K. A Serologic Test for Irritable Bowel Syndrome and Other News from ACG. Gastroenterology Press Highlights (2013); pp. 1-2. Retrieved from: <www.gastrojournal.org/pb/assets/raw/Health%20Advance/journals/ygast/November26_PressHighlight3.pdf> on Feb. 3, 2016.
Peng et al. a-Catenin Uses a Novel Mechanism to Activate Vinculin. The Journal of Biological Chemistry (2012). 287(10): 7728-7737.
Pimentel et al. A New Rat Model Links Two Complementary Theories in Irritable Bowel Syndrome. Digestive Diseases and Sciences (2007). 53(4):982-989.
Pimentel et al. Anti-vinculin antibodies: Multicenter validation of a diagnostic blood test for irritable bowel syndrome. The American Journal of Gastroenterology (2013). 108:1887; p. S571. Abstract Only.
Pimentel et al. Autoimmunity to vinculin in humans may be important in the pathophysiology of IBS. Gastroenterology (2014). 146(5); suppl 1, Su2020. Abstract Only.
Pimentel et al. Development and Validation of a Biomarker for Diarrhea-Predominant Irritable Bowel Syndrxome in Human Subjects. PLoS One (2015). 10(5): pp. 1-12.
Purdy et a. Characterisation of cytolethal distending toxin (CDT) mutants of Campylobacter jejuni. J. Med. Microbiol. (2000). 49: pp. 473-479.
Regent et al., Identification of Target Antigens of Anti-Endothelial Cell and Anti-Vascular Smooth Muscle Cell Antigodies in Patients with Giant Cell Arteritis: a Proteomic Approach, 2011, Arthritis Research & Therapy, 13: R107, 15 Pages.
Rezaie et al. Assessment of Anti-Vinculin and Anti-CdtB Antibodies in IBS Subtypes. Gastroenterology (2016).150(4). Supplement 1. p. S62.
Rezaie et al. Assessment of Anti-Vinculin and Anti-Cytolethal Distending Toxin B Antibodies in Subtypes of Irritable Bowel Syndrome, 2017, Digestive Diseases and Sciences, vol. 62(6), pp. 1480-1485.
Rolle et al. Structural basis of voiding dysfunction in megacystis microcolon intestinal hypoperistalsis syndrome. Journal of Pediatric Urology (2006). 2:277-284.
Spiller et al. Increased rectal mucosal enteroendocrine cells, T lymphocytes, and increased gut permeability following acute Campylobacter enteritis and inpost-dysenteric irritable bowel syndrome. Gut (2000). 47:804-811.
Suh et al. Patients with irritable bowel syndrome or constipation have an increased risk for ischaemic colitis. Alimentary Pharmacology & Therapeutics (2007). 25:681-692.
Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.
Trees et al. Genome Sequences of 228 Shiga Toxin-Producing *Escherichia coli* Isolates and 12 Isolates Representing Other Diarrheagenic *E. coli* Pathotypes. Genome Announc (2014). 2(4): 3 pages.
Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Su1424, Abstract Only.
Turkay et al. Noninvasive Methods in Evaluation of Inflammatory Bowel Disease: Where Do We Stand Now? An Update. Clinics (2010). 65(2):221-31.
Jee et al., ICC Density Predicts Bacterial Overgrowth in a Rat Model of Post-Infectious IBS, 2010, World J. Gastroenterol, vol. 16(29), pp. 3680-3686.
Weller et al., Complete Sequence of Human Vinculin and Assignment of the Gene to Chromosome 10, 1990, Proceedings of the National Academy of Sciences of the USA, vol. 87, pp. 5667-5671.
Pimentel, Evaluating a bacterial hypothesis in IBS using a modification of Koch's postulates: part 1, 2010, Am J Gastroenterol, vol. 105, pp. 718-721.
Riddle et al., Persisting Consequence of Intestinal Infection: Summary of the Seminar, 2014, Old Herborn University Seminar No. 7, pp. 125-137.
Villano et al., Systemic sclerosis sera affect fibrillin-1 deposition by dermal blood microvascular endothelial cells: therapeutic implications of cyclophosphamide, Arthritis Research & Therapy, 2013(15), pp. 1-12.
Beppu et al., Autoantibodies against vinculin in patients with chronic inflammatory demyelinating polyneuropathy, Journal of Neuroimmunology, 2015, pp. 9-15.
Suliman et al., Anti-Vinculin Antibodies: A Novel Biomarker in Systemic Sclerosis, and Its Association with Vascular Involvement,

(56) References Cited

OTHER PUBLICATIONS

Meeting: 2016 ACR/ARHP Annual Meeting, 2016, retrieved from: https://acrabstracts.org/abstract/anti-vinculinantibodies-a-novel-biomarker-in-systemic-sclerosis-and-its-association-with-vascular-involvement, Abstract.

Jayne, The diagnosis of vasculitis, Best Practice & Research Clinical Rheumatology, 2009, vol. 23(3), pp. 445-453.

Virandera et al., Antibodies to Cytolethal Distending Toxin B and Auto-Antibodies to Human Vinculin Are Elevated in IBS Subjects, Gastroenterology, 2013, vol. 144(5).

Supplementary European Search Report for EP 18744324 dated Oct. 21, 2020, 8 pages.

Sallam et al., Systematic review: pathophysiology and management of gastrointestinal dysmotility in systemic sclerosis (scleroderma), Alimentary Pharmacology & Therapeutics 23, 2006, pp. 691-712.

Savarino et al., Gastrointestinal motility disorder assessment in systemic sclerosis, Rheumatology, 2013, vol. 52, pp. 1095-1100.

Domsic et al., Gastrointestinal Manifestations of Systemic Sclerosis, Dig Dis Sci, 2008, vol. 53, 1163-1174.

Vasculitis Symptoms and Causes, Mayo Clinic, 2021, retrieved from the internet: https://www.mayoclinic.org/diseases-conditions/vasculitis/symptoms-causes/syc-20363435.

\* cited by examiner

FIG. 1

MKKIVFLILSFNVLFAALENYNTGTWNLQGSSAATESKWNVSIRQLITGANPMDVLAVQE
AGVLPSTAMMTPRQVQPVGVGIPIHEYIWNLGSVSRPSSVYIYYSRVDVGANRVNLAIVSR
VQADEVFVLPPPTVASRPIIGIRIGNDAFFNIHALASGGNDAGAIVAAVDMFFRNRPDINW
MILGDFNRESGALVTLLDPDLRARTRVVVPPSSTQTSGRTIDYAITGNSNTAALYNPPPIVAIL
ALEGLRTFLASDHFPVNFRRP (SEQ ID NO:1)

FIG. 2

| | |
|---|---|
| atgaaaaaaa tagtatttttt gattttaagt tttaatgtat tatttgccgc tttagaaaat | 60 |
| tacaacaccg gaacttggaa tttgcaaggc tcatcagctg caactgaaag caaatggaat | 120 |
| gttagtataa gacaactcat aaccggtgca aatcctatgg atgttttagc tgttcaagaa | 180 |
| gcgggggttt tacctagtac agctatgatg actcctagac aggtacaacc cgtgggcgtg | 240 |
| ggtattccta tacatgaata catatggaat ttaggctctg tatcaagacc tagctctgtt | 300 |
| tatatatatt attctagagt ggatgtagga gcaaatcgtg tgaatttagc tatcgttagc | 360 |
| agagtgcaag cggatgaagt ttttgtttta ccccctccaa cagttgcttc aagacctatt | 420 |
| ataggcatac gcataggcaa tgatgctttt ttcaatatac gcgctctagc aagtggggga | 480 |
| aatgacgcag gagccattgt cgctgctgtg gatatgtttt ttagaaatag acctgatatt | 540 |
| aattggatga ttttaggcga ttttaataga gaatcaggcg cctttagtaac cttgctagat | 600 |
| cctgacttaa gagcacgcac tcgcgtagtt gttccgcctt cttctacgca aacaagtgga | 660 |
| agaacgattg attatgctat cactggaaat tccaacactg cagctttata aacccacca | 720 |
| ccgatagttg cgatttttagc tttagaagga ttaagaacct ttttggcttc agatcatttt | 780 |
| cctgtaaatt ttagaagacc ttag | 804 |

(SEQ ID NO:2)

MKKIICLFLSFNLAFANLENFNVGTWNLQGSSAATESKWSVSVRQLVSGANPLDILMIQE
AGTLPRTATPTGRHVQQGGTPIDEYEWNLGTLSRPDRVFIYYSRVDVGANRVNLAIVSR
M
QAEEVIVLPPPTTVSRPIIGIRNGNDAFFNIHALANGGTDVGAIITAVDAHFANMPQVNW
MIAGDFNRDPSTITSTVDRELANRIRVVFPTSATQASGGTLDYAITGNSNRQQTYTPPLL
AAILMLASLRSHIVSDHFPVNFRKF (SEQ ID NO:5)

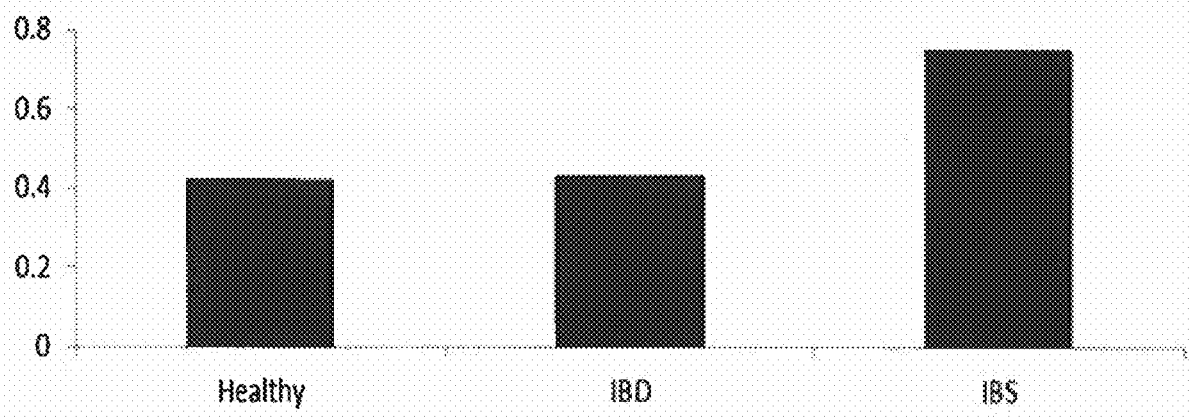

SEQUENCE LISTING

```
<160> NUMBER OF SEQ ID NOS: 12

<210> SEQ ID NO 1
<211> LENGTH: 267
<212> TYPE: PRT
<213> ORGANISM: Campylobacter coli

<400> SEQUENCE: 1

Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu
    50                  55                  60

Pro Ser Thr Ala Met Met Thr Pro Arg Gln Val Gln Pro Val Gly Val
65                  70                  75                  80

Gly Ile Pro Ile His Glu Tyr Ile Trp Asn Leu Gly Ser Val Ser Arg
                85                  90                  95

Pro Ser Ser Val Tyr Ile Tyr Tyr Ser Arg Val Asp Val Gly Ala Asn
            100                 105                 110

Arg Val Asn Leu Ala Ile Val Ser Arg Val Gln Ala Asp Glu Val Phe
        115                 120                 125

Val Leu Pro Pro Thr Val Ala Ser Arg Pro Ile Ile Gly Ile Arg
    130                 135                 140

Ile Gly Asn Asp Ala Phe Phe Asn Ile His Ala Leu Ala Ser Gly Gly
145                 150                 155                 160

Asn Asp Ala Gly Ala Ile Val Ala Ala Val Asp Met Phe Phe Arg Asn
                165                 170                 175

Arg Pro Asp Ile Asn Trp Met Ile Leu Gly Asp Phe Asn Arg Glu Ser
            180                 185                 190

Gly Ala Leu Val Thr Leu Leu Asp Pro Asp Leu Arg Ala Arg Thr Arg
        195                 200                 205

Val Val Val Pro Pro Ser Ser Thr Gln Thr Ser Gly Arg Thr Ile Asp
    210                 215                 220

Tyr Ala Ile Thr Gly Asn Ser Asn Thr Ala Ala Leu Tyr Asn Pro Pro
225                 230                 235                 240

Pro Ile Val Ala Ile Leu Ala Leu Glu Gly Leu Arg Thr Phe Leu Ala
                245                 250                 255
```

Ser Asp His Phe Pro Val Asn Phe Arg Arg Pro
            260                 265

<210> SEQ ID NO 2
<211> LENGTH: 804
<212> TYPE: DNA
<213> ORGANISM: Campylobacter coli

<400> SEQUENCE: 2

| | |
|---|---:|
| atgaaaaaaa tagtattttt gattttaagt tttaatgtat tatttgccgc tttagaaaat | 60 |
| tacaacaccg gaacttggaa tttgcaaggc tcatcagctg caactgaaag caatggaat | 120 |
| gttagtataa acaactcat aaccggtgca atcctatgg atgttttagc tgttcaagaa | 180 |
| gcggggtttt tacctagtac agctatgatg actcctagac aggtacaacc cgtgggcgtg | 240 |
| ggtattccta tacatgaata catatggaat ttaggctctg tatcaagacc tagctctgtt | 300 |
| tatatatatt attctagagt ggatgtagga gcaaatcgtg tgaatttagc tatcgttagc | 360 |
| agagtgcaag cggatgaagt tttgtttta ccccctccaa cagttgcttc aagacctat | 420 |
| ataggcatac gcataggcaa tgatgctttt ttcaatatac acgctctagc aagtggggga | 480 |
| aatgacgcag gagccattgt cgctgctgtg gatatgtttt ttagaaatag acctgatatt | 540 |
| aattggatga ttttaggcga ttttaataga gaatcaggcg ccttagtaac cttgctagat | 600 |
| cctgacttaa gagcacgcac tcgcgtagtt gttccgcctt cttctacgca aacaagtgga | 660 |
| agaacgattg attatgctat cactggaaat tccaacactg cagctttata caacccacca | 720 |
| ccgatagttg cgattttagc tttagaagga ttaagaaccct ttttggcttc agatcatttt | 780 |
| cctgtaaatt ttagaagacc ttag | 804 |

<210> SEQ ID NO 3
<211> LENGTH: 17
<212> TYPE: PRT
<213> ORGANISM: Campylobacter jejuni

<400> SEQUENCE: 3

Leu Asp Tyr Ala Ile Thr Gly Asn Ser Asn Arg Gln Gln Thr Tyr Thr
1               5                   10                  15

Pro

<210> SEQ ID NO 4
<211> LENGTH: 18
<212> TYPE: PRT
<213> ORGANISM: Campylobacter jejuni

<400> SEQUENCE: 4

Cys Leu Asp Tyr Ala Ile Thr Gly Asn Ser Asn Arg Gln Gln Thr Tyr
1               5                   10                  15

Thr Pro

<210> SEQ ID NO 5
<211> LENGTH: 265
<212> TYPE: PRT
<213> ORGANISM: Campylobacter jejuni

<400> SEQUENCE: 5

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
            35                  40                  45

Gly Ala Asn Pro Leu Asp Ile Leu Met Ile Gln Glu Ala Gly Thr Leu
 50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265

<210> SEQ ID NO 6
<211> LENGTH: 51
<212> TYPE: DNA
<213> ORGANISM: Campylobacter jejuni

<400> SEQUENCE: 6
cttgattatg caattacagg aaattcaaat agacaacaaa cctatactcc a        51

<210> SEQ ID NO 7
<211> LENGTH: 1066
<212> TYPE: PRT
<213> ORGANISM: Homo sapiens

<400> SEQUENCE: 7

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln

```
                85                  90                  95
Ser Asp Pro Tyr Ser Val Pro Ala Arg Asp Tyr Leu Ile Asp Gly Ser
                    100                 105                 110

Arg Gly Ile Leu Ser Gly Thr Ser Asp Leu Leu Thr Phe Asp Glu
            115                 120                 125

Ala Glu Val Arg Lys Ile Ile Arg Val Cys Lys Gly Ile Leu Glu Tyr
        130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
            195                 200                 205

Met Lys Ile Phe Val Thr Thr Lys Asn Ser Lys Asn Gln Gly Ile Glu
        210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
            500                 505                 510
```

```
Gly Val Gly Gln Ala Ala Ile Arg Gly Leu Val Ala Glu Gly His Arg
            515                 520                 525

Leu Ala Asn Val Met Met Gly Pro Tyr Arg Gln Asp Leu Leu Ala Lys
        530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Gly Asn Asp Ile Ile Ala Ala Ala Lys Arg Met Ala Leu
        915                 920                 925
```

Leu Met Ala Glu Met Ser Arg Leu Val Arg Gly Gly Ser Gly Thr Lys
930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
            965                 970                 975

Ile Arg Thr Asn Leu Leu Gln Val Cys Glu Arg Ile Pro Thr Ile Ser
            980                 985                 990

Thr Gln Leu Lys Ile Leu Ser Thr Val Lys Ala Thr Met Leu Gly Arg
            995                 1000                1005

Thr Asn Ile Ser Asp Glu Glu Ser Glu Gln Ala Thr Glu Met Leu
    1010                1015                1020

Val His Asn Ala Gln Asn Leu Met Gln Ser Val Lys Glu Thr Val
    1025                1030                1035

Arg Glu Ala Glu Ala Ala Ser Ile Lys Ile Arg Thr Asp Ala Gly
    1040                1045                1050

Phe Thr Leu Arg Trp Val Arg Lys Thr Pro Trp Tyr Gln
    1055                1060                1065

<210> SEQ ID NO 8
<211> LENGTH: 23
<212> TYPE: DNA
<213> ORGANISM: Artificial Sequence
<220> FEATURE:
<223> OTHER INFORMATION: synthetic construct

<400> SEQUENCE: 8
ggagattact gccctggctc cta                                          23

<210> SEQ ID NO 9
<211> LENGTH: 24
<212> TYPE: DNA
<213> ORGANISM: Artificial Sequence
<220> FEATURE:
<223> OTHER INFORMATION: synthetic construct

<400> SEQUENCE: 9
gactcatcgt actcctgctt gctg                                         24

<210> SEQ ID NO 10
<211> LENGTH: 20
<212> TYPE: DNA
<213> ORGANISM: Artificial Sequence
<220> FEATURE:
<223> OTHER INFORMATION: synthetic contruct

<400> SEQUENCE: 10
gccaagcagt gcacagataa                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic construct

<400> SEQUENCE: 11
tctttctaac ccagcgcagt                                              20

<210> SEQ ID NO 12
<211> LENGTH: 633
<212> TYPE: PRT

<213> ORGANISM: Shigella

<400> SEQUENCE: 12

Met His Asn Val Asn Thr Gln Ala Pro Thr Phe Leu Tyr Lys Ala
1               5                   10                  15

Thr Ser Pro Ser Ser Thr Glu Tyr Ser Glu Leu Lys Ser Lys Ile Ser
            20                  25                  30

Asp Ile His Ser Ser Gln Thr Ser Leu Lys Thr Pro Ala Ser Val Ser
                35                  40                  45

Glu Lys Glu Asn Phe Ala Thr Ser Phe Asn Gln Lys Cys Leu Asp Phe
    50                  55                  60

Leu Phe Ser Ser Ser Gly Lys Glu Asp Val Leu Arg Ser Ile Tyr Ser
65                  70                  75                  80

Asn Ser Met Asn Ala Tyr Ala Lys Ser Glu Ile Leu Glu Phe Ser Asn
                85                  90                  95

Val Leu Tyr Ser Leu Val His Gln Asn Gly Leu Asn Phe Glu Asn Glu
            100                 105                 110

Lys Gly Leu Gln Lys Ile Val Ala Gln Tyr Ser Glu Leu Ile Ile Lys
        115                 120                 125

Asp Lys Leu Ser Gln Asp Ser Ala Phe Gly Pro Trp Ser Ala Lys Asn
130                 135                 140

Lys Lys Leu His Gln Leu Arg Gln Asn Ile Glu His Arg Leu Ala Leu
145                 150                 155                 160

Leu Ala Gln Gln His Thr Ser Gly Glu Ala Leu Ser Leu Gly Gln Lys
                165                 170                 175

Leu Leu Asn Thr Glu Val Ser Ser Phe Ile Lys Asn Asn Ile Leu Ala
            180                 185                 190

Glu Leu Lys Leu Ser Asn Glu Thr Val Ser Ser Leu Lys Leu Asp Asp
        195                 200                 205

Leu Val Asp Ala Gln Ala Lys Leu Ala Phe Asp Ser Leu Arg Asn Gln
210                 215                 220

Arg Lys Asn Thr Ile Asp Ser Lys Gly Phe Gly Ile Gly Lys Leu Ser
225                 230                 235                 240

Arg Asp Leu Asn Thr Val Ala Val Phe Pro Glu Leu Leu Arg Lys Val
                245                 250                 255

Leu Asn Asp Ile Leu Glu Asp Ile Lys Asp Ser His Pro Ile Gln Asp
            260                 265                 270

Gly Leu Pro Thr Pro Pro Glu Asp Met Pro Asp Gly Gly Pro Thr Pro
        275                 280                 285

Gly Ala Asn Glu Lys Thr Ser Gln Pro Val Ile His Tyr His Ile Asn
    290                 295                 300

Asn Asp Asn Arg Thr Tyr Asp Asn Arg Val Phe Asp Asn Arg Val Tyr
305                 310                 315                 320

Asp Asn Ser Tyr His Glu Asn Pro Glu Asn Asp Ala Gln Ser Pro Thr
                325                 330                 335

Ser Gln Thr Asn Asp Leu Leu Ser Arg Asn Gly Asn Ser Leu Leu Asn
            340                 345                 350

Pro Gln Arg Ala Leu Val Gln Lys Val Thr Ser Val Leu Pro His Ser
        355                 360                 365

Ile Ser Asp Thr Val Gln Thr Phe Ala Asn Asn Ser Ala Leu Glu Lys
    370                 375                 380

Val Phe Asn His Thr Pro Asp Asn Ser Asp Gly Ile Gly Ser Asp Leu
385                 390                 395                 400

-continued

```
Leu Thr Thr Ser Ser Gln Glu Arg Ser Ala Asn Asn Ser Leu Ser Arg
                    405                 410                 415

Gly His Arg Pro Leu Asn Ile Gln Asn Ser Ser Thr Thr Pro Pro Leu
                420                 425                 430

His Pro Glu Gly Val Thr Ser Ser Asn Asp Asn Ser Ser Asp Thr Thr
            435                 440                 445

Lys Ser Ser Ala Ser Leu Ser His Arg Val Ala Ser Gln Ile Asn Lys
        450                 455                 460

Phe Asn Ser Asn Thr Asp Ser Lys Val Leu Gln Thr Asp Phe Leu Ser
465                 470                 475                 480

Arg Asn Gly Asp Thr Tyr Leu Thr Arg Glu Thr Ile Phe Glu Ala Ser
                485                 490                 495

Lys Lys Val Thr Asn Ser Leu Ser Asn Leu Ile Ser Leu Ile Gly Thr
                500                 505                 510

Lys Ser Gly Thr Gln Glu Arg Glu Leu Gln Glu Lys Ser Lys Asp Ile
            515                 520                 525

Thr Lys Ser Thr Thr Glu His Arg Ile Asn Asn Lys Leu Lys Val Thr
        530                 535                 540

Asp Ala Asn Ile Arg Asn Tyr Val Thr Glu Thr Asn Ala Asp Thr Ile
545                 550                 555                 560

Asp Lys Asn His Ala Ile Tyr Glu Lys Ala Lys Glu Val Ser Ser Ala
                565                 570                 575

Leu Ser Lys Val Leu Ser Lys Ile Asp Asp Thr Ser Ala Glu Leu Leu
                580                 585                 590

Thr Asp Asp Ile Ser Asp Leu Lys Asn Asn Asn Asp Ile Thr Ala Glu
            595                 600                 605

Asn Asn Asn Ile Tyr Lys Ala Ala Lys Asp Val Thr Thr Ser Leu Ser
        610                 615                 620

Lys Val Leu Lys Asn Ile Asn Lys Asp
625                 630
```

METHODS FOR DETECTING POST-INFECTIOUS IRRITABLE BOWEL SYNDROME

CROSS REFERENCE TO RELATED APPLICATIONS

This application is a continuation-in-part of U.S. application Ser. No. 16/152,806, filed Oct. 5, 2018, which is a continuation of U.S. application Ser. No. 14/878,416, filed Oct. 8, 2015, now issued as U.S. Pat. No. 10,132,814, which claims benefit of priority under 35 U.S.C. § 119(e) to U.S. provisional patent application No. 62/061,877, filed Oct. 9, 2014, and U.S. provisional patent application No. 62/085,825, filed Dec. 1, 2014, the entirety of which are hereby incorporated by reference; this application is also a continuation-in-part of U.S. application Ser. No. 16/594,935, filed Oct. 7, 2019, which is a continuation of U.S. application Ser. No. 15/922,604, filed Mar. 15, 2018, now issued as U.S. Pat. No. 10,466,254, which is a continuation of U.S. application Ser. No. 15/609,959, filed May 31, 2017, now issued as U.S. Pat. No. 9,952,223, which is a continuation of U.S. application Ser. No. 14/428,195, filed Mar. 13, 2015, now issued as U.S. Pat. No. 9,702,884, which is a National Phase of International Patent Application No. PCT/US2013/055626 filed Aug. 19, 2013, which designated the U.S. and that International Application was published under PCT Article 21(2) in English, which claims benefit of priority under 35 U.S.C. § 119(e) to U.S. provisional patent application No. 61/701,923 filed Sep. 17, 2012, and U.S. provisional patent application No. 61/762,632 filed Feb. 8, 2013, the entirety of which are hereby incorporated by reference; and this application is also a continuation-in-part of U.S. application Ser. No. 16/734,842, filed Jan. 6, 2020, which is a continuation of U.S. application Ser. No. 16/185,955, Filed Nov. 9, 2018, now issued as U.S. Pat. No. 10,527,621, which is a continuation of U.S. application Ser. No. 15/855,792, filed Dec. 27, 2017, now issued as U.S. Pat. No. 10,151,752, which is a continuation of U.S. application Ser. No. 14/793,523, now issued as U.S. Pat. No. 9,869,676, which is a continuation of U.S. application Ser. No. 13/148,252, filed Aug. 5, 2011, now issued as U.S. Pat. No. 9,110,081, which is a National Phase of International Application No. PCT/US2010/023911 filed Feb. 11, 2010, which designated the U.S. and that International Application was published under PCT Article 21(2) in English, which claims benefit of priority under 35 U.S.C. § 119(e) to U.S. provisional patent application No. 61/151,779 filed Feb. 11, 2009, and U.S. provisional application No. 61/286,250 filed Dec. 14, 2009, the entirety of which are hereby incorporated by reference.

REFERENCE TO A "SEQUENCE LISTING"

The sequence listing titled "SequenceListings-065472-000511US20", created on May 18, 2020, having 26 kb, and filed via EFS-Web with the instant application, is herein incorporated by reference as though fully set forth.

FIELD OF INVENTION

This invention relates to irritable bowel syndrome, inflammatory bowel disease, and Celiac disease, the diagnosis and treatments thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cytolethal distending toxin (CDT) is a bacterial protein toxin produced by several pathogenic bacteria. CDT is composed of three subunits, CdtA, CdtB and CdtC, which together form a ternary complex. CdtB is the active component, and CdtA and CdtC are involved in delivering CdtB into the cells. CDT controls host cells by CdtB-mediated limited DNA damage of the host cell chromosome, which triggers the response of the cell cycle checkpoint and results in G2 arrest in the cells. CDT also induces apoptotic cell death of lymphocytes, which may be relevant to onset or persistence of chronic infection by the producing bacteria. (Ohara et al., J. Biochem, 2004, Vol. 136, No. 4 409-413.) Additionally, the presence of CdtB is universal among bacteria that cause food poisoning (e.g., *Campylobacter* (e.g., *C. jejuni, C. coli*), *Escherichia coli* (e.g., enterotoxigenic *E. coli* (ETEC), enterohaemorrhagic *E. coli* (EHEC), enteropathogenic *E. coli* (EPEC)), *Salmonella, Shigella*, and *Clostridium difficile*).

Irritable bowel syndrome ("IBS") is a disorder characterized by, inter alia, cramping, abdominal pain, bloating, constipation, and diarrhea. IBS can cause a great deal of discomfort and distress. While many people can control their symptoms with diet, stress management, and medications, for some people IBS can be disabling. They may be unable to work, attend social events, or even travel short distances. As many as 20% of the adult population have symptoms of IBS; making it one of the most common disorders diagnosed by doctors.

In addition to irritable bowel syndrome, another phenomenon linked to IBS is non-ulcer dyspepsia (NUD). This is a condition whereby subjects experience discomfort in the upper abdominal area that cannot be explained by findings on an endoscopy such as an ulcer or irritation of the lining of stomach or intestine. This condition is another of the functional bowel conditions. There is a general recognition that very often there is an overlap between IBS and NUD to a degree that is more than just common occurrence (Talley et al., The association between non-ulcer dyspepsia and other gastrointestinal disorders. Scand J Gastroenterol 1985; 20:896-900). In addition, recent evidence suggests that acute gastroenteritis can precipitate IBS and NUD (Mearin et al., Dyspepsia and irritable bowel syndrome after a *Salmonella* and gastroenteritis outbreak: One year follow up cohort study. Gastroenterol 2005; 129:98-104.). This evidence suggests that the pathophysiology of IBS and NUD may be linked to this initial food poisoning insult. As such, it is likely that the same mechanisms are in play.

Accordingly, there exists a need for diagnosis, treatment, prevention and reduction of the likelihood of having or developing IBS as well as NUD. Heretofore, there has been no association between CDT and IBS or CDT and NUD. Based upon the inventors' findings, therapies and diagnostics based on the association between CDT and IBS as described herein can be beneficial for IBS subjects, to prevent or reduce a subject's likelihood of developing IBS and/or NUD.

Irritable bowel syndrome (IBS) is the most common functional gastrointestinal disorder. While the pathogenesis has historically focused on visceral hyperalgesia (1), recent work points to the pathophysiology of IBS being due to aberrations in gut flora. These hypotheses have emerged from two distinct areas of research. The first gut flora hypothesis is that small intestinal bacterial overgrowth (SIBO) may contribute to IBS and its symptoms. In a recent paper (2), Koch's postulates suggest that the evidence underpins this concept. This is further supported by recent phase III success of antibiotics in treating IBS (3) and culture studies of the proximal small bowel (Posserud and Pyleris studies). The other gut flora hypothesis is based on the development of IBS after an acute episode of gastroenteritis. There are now two meta-analyses, both of which reveal a similar finding that approximately 10% of subjects presenting with acute gastroenteritis will develop IBS long term (4, 5).

Many treatment methods of the prior art focuses on the relief of symptoms. Accordingly, there is a need in the art for additional methods of diagnosing and treating IBS, particularly treating the cause of IBS, as well as treating motility disorders of the gut and the bladder.

Irritable bowel syndrome (IBS) is the most commonly diagnosed condition in gastroenterology with reported prevalence rates of approximately 15% of the population. Over the last 30 years, the diagnosis of IBS has been based on clinical criteria. This is due to a poor understanding of the pathophysiology of this condition.

Two microbial concepts have emerged in the pathogenesis of IBS. The first suggests that IBS symptoms appear to be related to alterations in small bowel microbial flora. The evidence for this is based on breath testing, small bowel culture, small bowel flora deep sequencing, and the clinical response to the gut-specific antibiotic, rifaximin. The second microbial concept is that a subset of subjects develops IBS following an episode of acute gastroenteritis (AGE). Meta-analyses of classic outbreaks suggest that the rate of IBS developing after AGE is approximately 10%.

IBS is a condition that results in chronic changes in bowel function including diarrhea, constipation and alternating patterns, as well as abdominal symptoms including pain and bloating. Because the symptoms of IBS can overlap with organic diseases such as IBD and celiac disease, the diagnosis of IBS is often made after excluding organic diseases. In a recent multinational initiative, IBS experts agreed that these subjects suffer from significant changes in bowel habit and bloating as principal symptoms. In the absence of a clear pathophysiology of IBS, identification of subjects is based on a "diagnosis of exclusion" approach. This approach involves a great deal of expense and morbidity to patients with IBS, particularly those with D-IBS, including frequent body imaging, endoscopy and blood testing to rule out alternative organic explanations for their symptoms.

While the Rome criteria have been valuable in the standardization of IBS recruitment for clinical trials, these criteria still rely on a "diagnosis of exclusion" approach as they are non-specific. For example, the majority of subjects with Crohn's disease or ulcerative colitis satisfy the Rome Criteria. The Rome II Criteria were further helpful in defining IBS based on predominant bowel pattern such as diarrhea and constipation predominant forms. This approach led to drug pipelines for IBS treatment based on controlling symptoms in IBS. Prokinetics and secretagogues have been developed for C-IBS and anti-kinetics for D-IBS. However, these therapies are not based on causative mechanism of IBS and are instead based on symptom control. As a result, they can result in creating opposite symptoms.

While the diagnosis of celiac disease has been greatly enhanced by the measurement of serum tissue transglutaminase, there remains a need for biomarkers that distinguish IBS from IBD in the workup of chronic diarrhea. There remains a need in the art for methods, assays and systems to diagnose IBS and to distinguish IBS from other GI ailments such as IBD and celiac disease.

SUMMARY OF THE INVENTION

The following embodiments and aspects thereof are described and illustrated in conjunction with compositions and methods which are meant to be exemplary and illustrative, not limiting in scope.

The present invention provides for a method, comprising: obtaining a biological sample from a subject selected from the group consisting of: a subject in need of a diagnosis regarding irritable bowel syndrome (IBS), a subject in need of a diagnosis regarding a subset of IBS, a subject in need of a determination of a likelihood of having or developing IBS, a subject in need of a determination of a likelihood of having or developing a subset of IBS, a subject in need of a diagnosis regarding non-ulcer dyspepsia (NUD), a subject in need of a determination regarding small intestinal bacterial overgrowth (SIBO), a subject in need of a determination of a susceptibility to having SIBO, a subject who desires a prognosis of a response to antibiotic treatment for IBS, a subject who desires a prognosis of a response to antibiotic treatment to reduce the likelihood of having IBS and combinations thereof; detecting the presence or absence of cytolethal distending toxin (CDT) or one or more markers of CDT in the biological sample; and correlating the presence of CDT or one or more markers of CDT with a likely presence of IBS, a likely presence of a subset of IBS, a likelihood of having or developing IBS, a likelihood of having or developing a subset of IBS a likely presence of NUD, a likely presence of SIBO, a higher susceptibility to having SIBO, a higher likelihood of having a beneficial result from antibiotic treatment for IBS, and/or a higher likelihood of having a beneficial result from antibiotic treatment to reduce the likelihood of having IBS, or correlating an absence of CDT and an absence of one or more markers of CDT with a likely absence of IBS, a likely absence of the subset of IBS, a lower likelihood of having or developing IBS, a lower likelihood of having or developing the subset of IBS, a likely absence of NUD, a likely absence of SIBO, a lower susceptibility to having SIBO, a lower likelihood of having a beneficial result from antibiotic treatment for IBS, and/or a lower likelihood of having a beneficial result from antibiotic treatment to reduce the likelihood of having IBS.

In one embodiment, the method may further comprise identifying the subject in need of the diagnosis regarding IBS, the subject in need of the diagnosis regarding the subset of IBS, the subject in need of the determination of the likelihood of having or developing IBS, the subject in need of the determination of the likelihood of having or developing subset of IBS, the subject in need of the diagnosis regarding NUD, the subject in need of the determination regarding SIBO, the subject in need of the determination of the susceptibility to having SIBO, the subject who desires the prognosis of the response to antibiotic treatment for IBS, and/or the subject who desires the prognosis of the response to antibiotic treatment to reduce the likelihood of having IBS.

In another embodiment, the method may further comprise choosing an antibiotic therapy for the subject based on the likely presence of IBS, the likely presence of the subset of IBS, the likelihood of having or developing IBS, the likelihood of having or developing the subset of IBS, the likely presence of NUD, the likely presence of SIBO, the higher susceptibility to having SIBO, the higher likelihood of having the beneficial result from antibiotic treatment for IBS, and/or the higher likelihood of having the beneficial result from antibiotic treatment to reduce the likelihood of having IBS.

In one embodiment, the subset of IBS may be selected from the group consisting of constipation-predominant IBS, diarrhea-predominant IBS, mixed IBS, undetermined IBS, and antibiotic responsive IBS.

In a certain embodiment, the one or more markers of CDT may be an antibody capable of binding specifically to CDT, CdtA, CdtB, CdtC or a fragment thereof. In one embodiment, the CdtB may be CdtB of *Campylobacter jejuni*. In a certain embodiment, the CdtB of *Campylobacter jejuni* has an amino acid sequence at least 80% identical to SEQ ID NO:5.

In another embodiment, the antibody is capable of binding specifically to an epitope on 5 to 22 contiguous residues of SEQ ID NO:5. In a certain embodiment, the epitope may be on 17 contiguous residues as disclosed by SEQ ID NO:3. In another embodiment, the antibody may be capable of binding specifically to an epitope on SEQ ID NO:4.

In another embodiment, the CdtB may be CdtB of *Campylobacter coli* and has an amino acid sequence at least 80% identical to SEQ ID NO:1. In another embodiment, the CdtB may be CdtB of *Escherichia coli, Salmonella, Shigella*, or *Clostridium difficile*.

The present invention also provides for a method, comprising: providing a composition to elicit a specific immune response, comprising: an agent selected from the group consisting of a fragment of cytolethal distending toxin (CDT) incapable of causing irritable bowel syndrome (IBS), CdtA incapable of causing IBS, CdtB incapable of causing IBS, CdtC incapable of causing IBS, CDT mutein incapable of causing IBS, a fragment of CDT mutein incapable of causing IBS, CdtA mutein incapable of causing IBS, CdtB mutein incapable of causing IBS, CdtC mutein incapable of causing IBS, a bacterium comprising a mutated CDT gene rendering the bacterium incapable of causing IBS, and combinations thereof; and administering the composition to a subject in need thereof to elicit a specific immune response. In various embodiments, eliciting the specific immune response reduces the subject's likelihood of developing or having IBS, or reduces the subject's likelihood of developing or having non-ulcer dyspepsia (NUD).

In one embodiment, the bacterium may be *Campylobacter jejuni* 81-176 that failed to express a functional cytolethal distending toxin B (CdtB) due to an insertion mutation at the gene for CdtB. In a certain embodiment, the bacterium may be killed. In another embodiment, the bacterium may be attenuated.

The present invention also provides for a method, comprising: providing a cytolethal distending toxin (CDT) inhibitor and/or a CDT neutralizer to reduce the likelihood of developing or having irritable bowel syndrome (IBS) or to reduce the likelihood of developing or having non-ulcer dyspepsia (NUD); and administering the CDT inhibitor and/or the CDT neutralizer to a subject in need thereof.

In one embodiment, the CDT inhibitor and/or the CDT neutralizer may be an antibody capable of binding specifically to CDT or a subunit of CDT. In one embodiment, the subunit of CDT may be CdtB. In a certain embodiment, the CdtB may be CdtB of *Campylobacter jejuni*. In a certain embodiment, the CdtB of *Campylobacter jejuni* may have an amino acid sequence at least 80% identical to SEQ ID NO:5.

In another embodiment, the antibody binds specifically to an epitope on 5 to 22 contiguous residues of SEQ ID NO:5. In another embodiment, the epitope is on 17 contiguous residues as disclosed by SEQ ID NO:3.

In another embodiment, the antibody is capable of binding specifically to an epitope on SEQ ID NO:4.

In another embodiment, the CdtB may be CdtB of *Campylobacter coli* and may have an amino acid sequence at least 80% identical to SEQ ID NO:1. In another embodiment, the CdtB may be CdtB of *Escherichia coli, Salmonella, Shigella* or *Clostridium difficile*.

The present invention also provides a purified antibody that binds specifically to cytolethal distending toxin (CDT) a subunit of CDT and inhibits or neutralizes CDT or the subunit of CDT. In one embodiment, the subunit of CDT may be CdtB. In a certain embodiment, the CdtB may be CdtB of *Campylobacter jejuni*. In one embodiment, the CdtB of *Campylobacter jejuni* may have an amino acid sequence at least 80% identical to SEQ ID NO:5.

In another embodiment, the purified antibody binds specifically to an epitope on 5 to 22 contiguous residues of SEQ ID NO:5. In one embodiment, the epitope may be on 17 contiguous residues as disclosed by SEQ ID NO:3.

In another embodiment, the purified antibody binds specifically to an epitope on SEQ ID NO:4.

In another embodiment, the CdtB is CdtB of *Campylobacter coli* and has an amino acid sequence at least 80% identical to SEQ ID NO:1.

Various embodiments of the present invention provide for a method, comprising: providing a biological sample from a subject desiring diagnosis of a gastrointestinal motility disorder, bladder motility disorder, or fibromyalgia; detecting in the biological sample, a presence or a level of an anti-vinculin antibody; and determining a presence or likely presence of the gastrointestinal motility disorder, bladder motility disorder, or fibromyalgia if the presence of the anti-vinculin antibody is detected, if the level of the anti-vinculin antibody is higher than an established control level, or if the level of the anti-vinculin antibody is significantly higher than an established control level, or determining an absence or likely absence of the gastrointestinal motility disorder, bladder motility disorder, or fibromyalgia if an absence of the anti-vinculin antibody is detected, if the level of the anti-vinculin antibody is equal to or lower than an established control level, or if the level of the anti-vinculin antibody is not significantly higher than an established control level.

In various embodiments, the method can further comprise selecting a therapy for the gastrointestinal motility disorder, bladder motility disorder, or fibromyalgia if the presence or likely presence of the gastrointestinal motility disorder, bladder motility disorder, or fibromyalgia is determined.

In various embodiments, the therapy can be a course of antibiotic therapy. In various embodiments, the therapy can comprise an anti-vinculin antibody neutralizing agent or an anti-vinculin antibody inhibiting agent. In various embodiments, the therapy can comprise an agent to change vinculin from an inactive state to an active state. In various embodiments, the therapy can comprise a vinculin agonist. In various embodiments, the vinculin agonist can be a vinculin activating peptide. In various embodiments, the therapy can comprise a vinculin activator. In various embodiments, the vinculin activator can be talin, f-actin, a-catenin or a combination thereof.

In various embodiments, the method can further comprise administering the therapy.

Various embodiments of the present invention provide for a system, comprising: an isolated biological sample from a subject desiring diagnosis of a gastrointestinal motility disorder, bladder motility disorder, or fibromyalgia; and an assay for detecting in the biological sample, a presence of an anti-vinculin antibody.

In various embodiments, the assay can be an enzyme-linked immunosorbent assay (ELISA), wherein the ELISA comprises using vinculin, SEQ ID NO:7 or a fragment thereof as a substrate or reagent to bind the anti-vinculin antibody.

Various embodiments of the present invention provide for a method, comprising: providing a biological sample from a subject desiring diagnosis of a gastrointestinal motility disorder, bladder motility disorder, or fibromyalgia; detecting in the biological same, a presence or a level of an anti-vinculin antibody; and determining a presence or likely presence of irritable bowel syndrome (IBS) if the presence of the anti-vinculin antibody is detected, if the level of the anti-vinculin antibody is higher than an established control level, or if the level of the anti-vinculin antibody is significantly higher than an established control level, or determining an presence or likely presence of inflammatory bowel disease (IBD) if an absence of the anti-vinculin antibody is detected, if the level of the anti-vinculin antibody is equal to or lower than an established control level, or if the level of the anti-vinculin antibody is not significantly higher than an established control level.

In various embodiments, the method can further comprise selecting an IBS therapy if IBS is diagnosed, or selecting an IBD therapy if IBD is diagnosed. In various embodiments, the IBS therapy can be a course of antibiotic therapy. In various embodiments, the IBS therapy can comprise an anti-vinculin antibody neutralizing agent or an anti-vinculin antibody inhibiting agent. In various embodiments, the IBS therapy can comprise an agent to change vinculin from an inactive state to an active state. In various embodiments, the IBS therapy can comprise a vinculin agonist. In various embodiments, the vinculin agonist can be a vinculin activating peptide. In various embodiments, the IBS therapy can comprise a vinculin activator. In various embodiments, the vinculin activator can be talin, f-actin, a-catenin or a combination thereof.

In various embodiments, the method can further comprise administering the IBS therapy or the IBD therapy.

Various embodiments of the present invention provide for a system, comprising: an isolated biological sample from a subject desiring a diagnosis to distinguish between irritable bowel syndrome (IBS) and inflammatory bowel disease (IBD); and an assay for detecting in the biological sample, a presence of an anti-vinculin antibody.

In various embodiments, the assay can be an enzyme-linked immunosorbent assay (ELISA), wherein the ELISA comprises using vinculin, SEQ ID NO:7 or a fragment thereof as a substrate or reagent to bind the anti-vinculin antibody.

Various embodiments of the present invention provide for a method, comprising: providing an therapy agent selected from the group consisting of: an anti-vinculin antibody neutralizing agent, an anti-vinculin antibody inhibiting agent, an agent capable of changing vinculin from an inactive state to an active state, a vinculin agonist, a vinculin activator, and combinations thereof; and administering the therapy agent to a subject desiring treatment of a gastrointestinal motility disorder, bladder motility disorder, or fibromyalgia to treat the gastrointestinal motility disorder, bladder motility disorder, or fibromyalgia.

In various embodiments, the vinculin agonist can be a vinculin activating peptide. In various embodiments, the vinculin activator can be talin, f-actin, a-catenin or a combination thereof.

Various embodiments of the present invention provide for a method of distinguishing irritable bowel syndrome (IBS) from inflammatory bowel disease (IBD), celiac disease, or both, comprising: obtaining a biological sample from a subject desiring a diagnosis to distinguish IBS from IBD, celiac disease, or both; detecting in the biological sample, levels of anti-vinculin and anti-CdtB antibodies; and making a diagnosis of IBS if the level of anti-vinculin antibodies is higher than an established control level of anti-vinculin antibodies, the level of anti-CdtB antibodies is higher than an established control level of anti-CdtB antibodies, or both levels of anti-vinculin antibodies and anti-CdtB antibodies are higher than the established control levels of anti-vinculin antibodies and anti-CdtB antibodies, or making a diagnosis of IBD, suspicion of IBD, celiac disease or suspicion of celiac disease if the level of anti-vinculin antibodies is not higher than the established control level of anti-vinculin antibodies and the level of anti-CdtB antibodies is not higher than the established control level of anti-CdtB antibodies.

In various embodiments, the biological sample can be whole blood, serum, or plasma.

In various embodiments, detecting in the biological sample can comprise using enzyme-linked immunosorbent assay (ELISA). In various embodiments, detecting in the biological sample can comprise using immunohistochemistry, flow cytometry, fluorescence in situ hybridization (FISH), radioimmuno assays, or affinity purification.

In various embodiments, the anti-vinculin antibodies can be capable of binding specifically to an epitope on vinculin or SEQ ID NO:7.

In various embodiments, the anti-CdtB antibodies can be capable of binding specifically to an epitope on CdtB of *Campylobacter jejuni* or SEQ ID NO:5.

In certain embodiments, the diagnosis of IBS can be made if the level of anti-vinculin antibodies is higher than the established control level of anti-vinculin antibodies. In certain embodiments, the diagnosis of IBS can be made if the level of anti-CdtB antibodies is higher than the established control level of anti-CdtB antibodies. In various embodiments, the diagnosis of IBS can be made if both levels of anti-vinculin antibodies and anti-CdtB antibodies are higher than the established control levels of anti-vinculin antibodies and anti-CdtB antibodies.

In various embodiments, the established control level of anti-vinculin antibodies, anti-CdtB antibodies, or both can be an optical density measurement.

Various embodiments of the present invention provide for a method of selecting a treatment for irritable bowel syndrome (IBS), inflammatory bowel disease (IBD), or celiac disease, comprising: obtaining a biological sample from a subject desiring a diagnosis to distinguish IBS from IBD, celiac disease, or both; detecting in the biological sample, levels of anti-vinculin and anti-CdtB antibodies; making a diagnosis of IBS if the level of anti-vinculin antibodies is higher than an established control level of anti-vinculin antibodies, the level of anti-CdtB antibodies is higher than an established control level of anti-CdtB antibodies, or both levels of anti-vinculin antibodies and anti-CdtB antibodies are higher than the established control levels of anti-vinculin antibodies and anti-CdtB antibodies, or making a diagnosis of IBD, suspicion of IBD, celiac disease or suspicion of celiac disease if the level of anti-vinculin antibodies is not higher than the established control level of anti-vinculin antibodies and the level of anti-CdtB antibodies is not higher than the established control level of anti-CdtB antibodies; and selecting an IBS treatment if IBS is diagnosed, selecting an IBD treatment if IBD is diagnosed or suspected, or selecting a celiac treatment if celiac disease is diagnosed or suspected.

In various embodiments, the biological sample can be whole blood, serum, or plasma.

In various embodiments, detecting in the biological sample can comprise using enzyme-linked immunosorbent assay (ELISA). In various embodiments, detecting in the biological sample can comprise using immunohistochemistry, flow cytometry, fluorescence in situ hybridization (FISH), radioimmuno assays, or affinity purification.

In various embodiments, the anti-vinculin antibodies can be capable of binding specifically to an epitope on vinculin or SEQ ID NO:7.

In various embodiments, the anti-CdtB antibodies can be capable of binding specifically to an epitope on CdtB of *Campylobacter jejuni* or SEQ ID NO:5.

In various embodiments, the established control level of anti-vinculin antibodies, anti-CdtB antibodies, or both can be an optical density measurement.

In certain embodiments, the diagnosis of IBS can be made if the level of anti-vinculin antibodies is higher than the established control level of anti-vinculin antibodies. In certain embodiments, the diagnosis of IBS can be made if the level of anti-CdtB antibodies is higher than the established control level of anti-CdtB antibodies. In certain embodiments, the diagnosis of IBS can be made if both levels of anti-vinculin antibodies and anti-CdtB antibodies are higher than the established control levels of anti-vinculin antibodies and anti-CdtB antibodies.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts the amino acid sequence of CdtB of *Campylobacter coli* (SEQ ID NO:1) in accordance with an embodiment of the present invention.

FIG. 2 depicts the nucleic acid sequence of CdtB of *Campylobacter coli* (SEQ ID NO:2) in accordance with an embodiment of the present invention.

FIG. 23 depicts titer of antibodies that were measured in IBS, IBD and healthy controls. IBS subjects had the highest level of antibody in accordance with various embodiments of the present invention. The y axis is the optical density (OD) of the ELISA test.

DESCRIPTION OF THE INVENTION

Figures 3, 4:
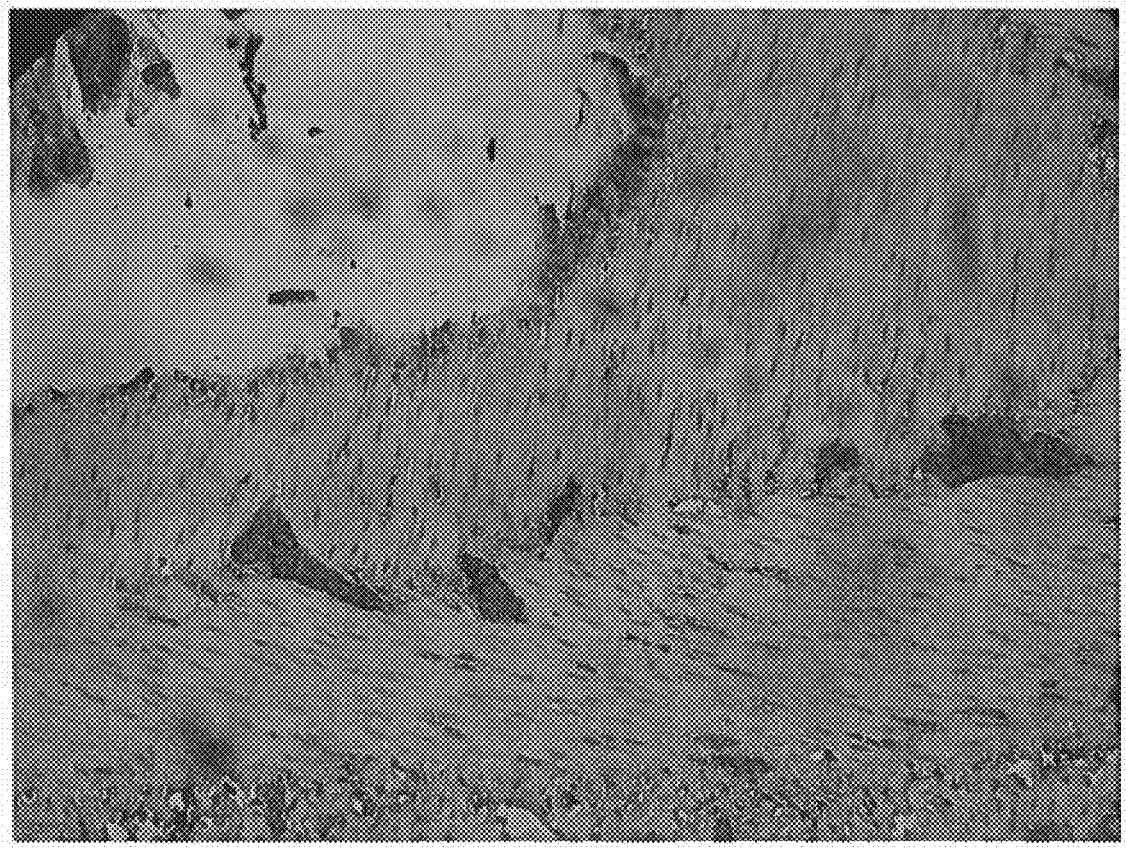
FIG. 3 depicts a nerve stained with antibodies against CdtB in accordance with an embodiment of the present invention.
FIG. 4 depicts the amino acid sequence of CdtB of *Campylobacter jejuni* subsp. *jejuni* 81-176 (SEQ ID NO:5) in accordance with an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ *ed., Revised*, J. Wiley & Sons (New York, N.Y. 2006); and Sambrook and Russel, *Molecular Cloning: A Laboratory Manual* $4^{th}$ *ed.*, Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* $2^{nd}$ *ed*. (Cold Spring Harbor Press, Cold Spring Harbor N.Y., 2013); Kohler and Milstein, (1976) Eur. J. Immunol. 6:511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334: 544-54 (1989); Tomlinson I. and Holliger P. (2000) Methods Enzymol, 326, 461-479; Holliger P. (2005) Nat. Biotechnol. September; 23(9): 1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

"Beneficial results" may include, but are in no way limited to, lessening or alleviating the severity of the disease condition, preventing the disease condition from worsening, slowing down the progression of the disease condition, preventing the development of the disease condition, reducing the likelihood of developing the disease condition, and curing the disease condition.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"CDT mutein" and "mutein of CDT" refer to a CDT molecule or a CDT subunit having one or more amino acids that have been mutated to alter its properties (e.g., inability to cause conditions or disease conditions described herein, capability to elicit a specific immune response and/or to serve as a vaccine). Mutations include substitution, deletion and/or insertion of one or more amino acids.

"Conditions" and "disease conditions," as used herein may include, but are in no way limited to any form of irritable bowel syndrome (e.g., diarrhea-predominant, constipation-predominant, mixed (constipation and diarrhea), and undetermined), altered bowel function, and irregular bowel pattern.

"Irregular bowel pattern" as used herein refers to a change in the consistency of stool form and/or a change in the frequency of bowel movements.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Treatment" and "treating," as used herein refer to both therapeutic treatment and prophylactic or preventative measures (e.g., to reduce the likelihood of having the condition or disease condition), wherein the object is to prevent or slow down (lessen) the targeted pathologic condition or disorder even if the treatment is ultimately unsuccessful. Those in need of treatment include those already with the condition or disorder as well as those prone to have the condition or disorder or those in whom the condition or disorder is to be prevented (e.g., reducing the likelihood of having the condition or disorder).

"Purified" antibody as used herein refers to an antibody which has been identified, separated and/or recovered from a component of its natural environment. For example, composition comprising an antibody as described herein will be purified from a cell culture or other synthetic environment to greater than 60%, 70%, 80%, 85%, 90%, 95%, 96%, 97%, 98%, or 99% by weight of the antibody.

"Significantly higher" as used herein relating to reference or control amounts refers to a statistically significant amount higher than the reference or control amount.

In a new post-infectious rat model designed to investigate the pathophysiology of irritable bowel syndrome (IBS), rats developed altered stool form 3 months after clearance of

*Campylobacter jejuni* infection. A common toxin among the numerous bacterial pathogens known to cause acute gastroenteritis and post-infectious IBS is cytolethal distending toxin (CDT). The inventors aimed to determine if CDT plays a role in the long term altered bowel function after gastroenteritis using a rat model of post-infectious IBS. The inventors found that CDT is important in the development of chronic altered bowel function in a rat model of post-infectious IBS. Rats exposed to a *Campylobacter* strain that was deficient in CDT had bowel patterns more consistent with normal rats.

Further, the inventors discovered that two distinct antibodies to the B subunit of the cytolethal distending toxin both appear to bind rat intestinal neuromuscular elements even in the absence of previous exposure to *C. jejuni*. This finding suggests that anti-CdtB antibodies may be reacting to a host protein or structure with sequence homology or structural similarity to CdtB. It also raises the possibility that molecular mimicry and aberrant host immune responses may mediate chronic GI sequelae (e.g., PI-IBS) of *C. jejuni* infection. As such, there may be a protein on nerves that is similar to CDT and the immune system is reacting to that protein after infection with *C. jejuni*. This can cause long term disturbance in bowel function. Thus, detecting the antibody in human bloodstream could allow for the diagnosis of IBS.

Various embodiments of the present invention are based on the findings that CDT is important in the development of chronic altered bowel function in a rat model of post-infectious IBS and that anti-CdtB antibodies may be reacting to a host protein with homology to CdtB.

Various embodiments of the present invention provide agents capable of inhibiting and/or neutralizing CDT ("CDT inhibitor" and "CDT neutralizer").

In various embodiments, the agent is a purified antibody that binds specifically to CDT and inhibits and/or neutralizes the activity of CDT. These antibodies are also useful for additional purposes, such as diagnosing a subject's likelihood of having IBS, as discussed below. The amino acid sequences of CDT are known in the art.

In one embodiment, the purified antibody specifically binds to an epitope on the receptor-binding domain of CDT.

In another embodiment, the purified antibody binds specifically to the CdtA subunit of CDT. In another embodiment, the purified antibody binds specifically to the CdtB subunit of CDT. In another embodiment, the purified antibody binds specifically to the CdtC subunit of CDT.

An example of a CdtB amino acid sequence is *Campylobacter jejuni* cytolethal distending toxin B, which has the amino acid sequence (SEQ ID NO: 5) as shown in FIG. 4.

Another example of a CdtB amino acid sequence is *Campylobacter coli* cytolethal distending toxin B, which has the amino acid sequence (SEQ ID NO:1) and nucleic acid sequence (SEQ ID NO:2), as shown in FIGS. 1 and 2, respectively.

Accordingly, in one embodiment, the purified antibody binds specifically to SEQ ID NO:5 (CdtB of *C. jejuni*). In various embodiments, the purified antibody binds specifically to an amino acid sequence at least 80%, 85%, 90%, 95%, 96%, 97%, 98%, or 99% identical to SEQ ID NO: 5.

In another embodiment, the purified antibody binds specifically to SEQ ID NO:1 (CdtB of *C. coli*). In various embodiments, the purified antibody binds specifically to an amino acid sequence at least 80%, 85%, 90%, 95%, 96%, 97%, 98%, or 99% identical to SEQ ID NO:1.

In another embodiment, the purified antibody binds specifically to a 17 residue peptide of CdtB (e.g., 17 residues of SEQ. ID NOs: 1 or 5). In one embodiment, the 17 residue peptide has the following sequence: LDYAITGNSNRQQTYTP (SEQ ID NO:3).

In other embodiments, the antibody binds specifically to a 17 residue peptide that has at least 80%, 85%, 90%, 95%, 96%, 97%, 98%, 99% or 100% homology with 17 contiguous residues of CdtB (e.g., 17 contiguous residues of SEQ. ID NOs: 1 or 5). In one embodiment, the 17 residues of CdtB have the following sequence: LDYAITGNSNRQQTYTP (SEQ ID NO:3).

In other embodiments, the antibody binds specifically to a polypeptide comprising 17 residues that have at least 80%, 85%, 90%, 95%, 96%, 97%, 98%, 99% or 100% homology with 17 contiguous residues of CdtB (e.g., 17 residues of SEQ. ID NOs: 1 or 5). In one embodiment, the 17 contiguous residues of CdtB have the following sequence: LDYAITGNSNRQQTYTP (SEQ ID NO:3).

In another embodiment, the purified antibody binds specifically to an 18 residue peptide having the following sequence: CLDYAITGNSNRQQTYTP (SEQ ID NO:4). The cysteine at the N-terminus was added to SEQ ID NO:3 for purposes of conjugation.

In other embodiments, the antibody binds specifically to a polypeptide comprising 18 residues that have at least 80%, 85%, 90%, 95%, 96%, 97%, 98%, 99% or 100% homology to CLDYAITGNSNRQQTYTP (SEQ ID NO:4).

In another embodiment, the purified antibody binds specifically to a 5, 6, 7, 8, 9, 10, 11, 12, 13, 14, 15, 16, 17, 18, 19, 20, 21, or 22 residue peptide that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). In another embodiment, the purified antibody binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). Contiguous residues of SEQ ID NO:1 include those beginning at any amino acid and ending at any amino acid of SEQ ID NO:1. Contiguous residues of SEQ ID NO:5 include those beginning at any amino acid and ending at any amino acid of SEQ ID NO:5.

In another embodiment, the purified antibody binds specifically to a 5, 6, 7, 8, 9, 10, 11, 12, 13, 14, 15, 16, or 17 residue peptide that has at least 80%, 85%, 90%, 95%, 96%, 97%, 98%, 99% or 100% homology with 5, 6, 7, 8, 9, 10, 11, 12, 13, 14, 15, 16, or 17 contiguous residues of LDYAITGNSNRQQTYTP (SEQ ID NO:3) (e.g., 5, 6, 7, 8, 9, 10, 11, 12, 13, 14, 15, 16, or 17 contiguous residues of SEQ ID NO:3). In another embodiment, the purified antibody binds specifically to a polypeptide comprising 5, 6, 7, 8, 9, 10, 11, 12, 13, 14, 15, 16, or 17 residues that has at least 80%, 85%, 90%, 95%, 96%, 97%, 98%, 99% or 100% homology with 5, 6, 7, 8, 9, 10, 11, 12, 13, 14, 15, 16, or 17 contiguous residues of SEQ ID NO:3 (e.g., 5, 6, 7, 8, 9, 10, 11, 12, 13, 14, 15, 16, or 17 contiguous residues of SEQ ID NO:3). Contiguous residues of SEQ ID NO: 3 include those beginning at any amino acid and ending at any amino acid of SEQ ID NO: 3.

In another embodiment, the purified antibody binds specifically to a 17 residue peptide encoded by the CdtB gene sequence. In particular embodiments, the purified antibody binds specifically to a 17 residue peptide encoded by SEQ ID NO: 2. In various embodiments, the purified antibody binds specifically to a 14, 15, 16, 17, 18, 19, 20, 21, or 22 residue peptide encoded by SEQ ID NO: 2. In various embodiments, the purified antibody binds specifically to a 14, 15, 16, 17, 18, 19, 20, 21, or 22 residue peptide that has at least 80%, 85%, 90%, 95%, 96%, 97%, 98%, 99% or 100% homology to 14, 15, 16, 17, 18, 19, 20, 21, or 22 contiguous residues encoded by SEQ ID NO: 2. In various embodiments, the purified antibody binds specifically to a polypeptide comprising 14, 15, 16, 17, 18, 19, 20, 21, or 22 residues that have at least 80%, 85%, 90%, 95%, 96%, 97%, 98%, 99% or 100% homology to 14, 15, 16, 17, 18, 19, 20, 21, or 22 contiguous residues encoded by SEQ ID NO: 2.

In another embodiment, the purified antibody binds specifically to a peptide encoded by the nucleic acid sequence having the following sequence: CTTGATTATGCAATTA-CAGGAAATTCAAATAGACAACAAACCTATACTCCA (SEQ ID NO:6), which encodes the 17 amino acid peptide of SEQ ID NO:3. In another embodiment, the purified antibody binds specifically to a polypeptide comprising a peptide encoded by SEQ ID NO:6.

In another embodiment, the purified antibody binds specifically to CdtB purified from *E. coli* overexpressing a near full-length CdtB ORF. (See Infection and Immunity, December 2000, p. 6535-6541, Vol. 68, No. 12, herein incorporated by reference in its entirety as though fully set forth.)

In another embodiment, the purified antibody binds specifically to CDT and inhibits the binding of CDT to its receptor.

In another embodiment, the purified antibody binds specifically to CDT and achieves at least 25%, 30%, 40%, or 50% neutralization; for example, of $10^4$ infectious units of bacteria or CDT in a 24 hour assay at a concentration of 1 μg antibody per milliliter.

One of skill in the art will be able to produce the antibodies described herein without undue experimentation in light of the disclosure herein, including the examples.

Methods of preparing monoclonal antibodies are known in the art. For example, monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include CDT or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) *Monoclonal Antibodies: Principles and Practice* Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In another embodiment the antibodies to an epitope for CDT as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. *Nature* 321:522-525; Riechmann et al. 1988. *Nature* 332:323-329; Presta. 1992. *Curr. Op. Struct. Biol.* 2:593-596). Humanization can be essentially performed following methods of Winter and co-workers (see, e.g., Jones et al. 1986. *Nature* 321:522-525; Riechmann et al. 1988. *Nature* 332:323-327; and Verhoeyen et al. 1988. *Science* 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In another embodiment the antibodies to an epitope of CDT as described herein or a fragment thereof are human antibodies. Human antibodies can also be produced using various techniques known in the art, including phage display libraries (Hoogenboom and Winter. 1991. *J Mol. Biol.* 227:381-388; Marks et al. 1991. *J Mol. Biol.* 222:581-597) or the preparation of human monoclonal antibodies (e.g., Cole et al. 1985. *Monoclonal Antibodies and Cancer Therapy* Liss; Boerner et al. 1991. *J. Immunol.* 147(1):86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. *Bio/Technology* 10:779-783; Lonberg et al. 1994. *Nature* 368:856-859; Morrison. 1994. *Nature* 368: 812-13; Fishwild et al. 1996. *Nature Biotechnology* 14:845-51; Neuberger. 1996. *Nature Biotechnology* 14:826; Lonberg and Huszar. 1995. *Intern. Rev. Immunol.* 13:65-93. U.S. Pat. No. 6,719,971 also provides guidance to methods of generating humanized antibodies.

To determine which monoclonal antibodies are CDT inhibitors or CDT neutralizers, the use of a screening assay can be performed. Screening assays are known in the art and can be performed without undue experimentation. (e.g., AbuOun et al., *Cytolethal Distending Toxin (CDT)-Negative Campylobacter jejuni Strains and Anti-CDT Neutralizing Antibodies Are Induced during Human Infection but Not during Colonization in Chickens*. Infect Immun. 2005 May; 73(5): 3053-3062.) For example, monoclonal antibodies may be tested for their capacities to neutralize the in vitro CDT activity from CDT-positive bacterial species (e.g., CDT-positive *C. jejuni* strains). Lysates from CDT-positive *C. jejuni* strains are pretreated with rabbit anti-*C. jejuni* antisera, and the CDT activity is tested for neutralization.

In other embodiments, the agent may be a competitive or noncompetitive inhibitor of a CDT receptor (e.g., a competitive or noncompetitive ligand for a CDT receptor). In various embodiments, the agent is also capable of covalent or noncovalent modification to CDT, its receptor, or a component of an effector in the pathway. In one embodiment, the agent is a CDT receptor antagonist to obviate G2 arrest in the cell (e.g., turns the cell back on).

In another embodiment, the agent may be an agent capable of inhibiting the CDT operon. In one embodiment, the agent may be a regulatory repressor protein capable of binding to the operator and preventing the transcription of the genes on the operon.

Another embodiment of the present invention provides a method of purifying CDT from a biological sample containing CDT, comprising providing an affinity matrix comprising an antibody that binds specifically to CDT bound to a solid support; contacting the biological sample with the affinity matrix, to produce an affinity matrix-CDT complex; separating the affinity matrix-CDT complex from the remainder of the biological sample; and releasing CDT from the affinity matrix.

Another embodiment of the present invention provides a method of treating IBS in a subject in need thereof, comprising providing a composition comprising a CDT inhibitor and/or CDT neutralizer, and administering the composition to the subject to treat the IBS. In one embodiment, the IBS is caused by CDT or resulted from an exposure to CDT; particularly, CDT in the intestines. In various embodiments, the CDT inhibitor and/or CDT neutralizer may be ones as described above.

Another embodiment of the present invention provides a method of preventing IBS or reducing the likelihood of developing IBS in a subject in need thereof, comprising providing a composition comprising a CDT inhibitor and/or CDT neutralizer and administering the composition to the subject to prevent IBS or to reduce the likelihood of developing IBS in the subject. In one embodiment, the IBS is caused by CDT or resulted from an exposure to CDT; particularly, CDT in the intestines. In various embodiments, the CDT inhibitor and/or CDT neutralizer may be a CDT inhibitor and/or CDT neutralizer as described above.

Another embodiment of the present invention provides for a composition to elicit a specific immune response in a subject; for example, a vaccine.

In one embodiment, the composition is useful to prevent IBS, to reduce the likelihood of developing or having IBS, and/or to treat IBS. In one embodiment, the composition comprises a fragment of CDT, CdtA, CdtB, CdtC, CDT mutein, CdtA mutein, CdtB mutein, CdtC mutein, or combinations thereof that will not cause IBS. Such muteins may be used to prevent CDT from causing IBS or to reduce the likelihood of CDT causing IBS. In another embodiment, the composition comprises heat killed, attenuated or inactivated bacteria that contain CDT or the CDT gene. In another embodiment, the composition comprises bacteria with a mutated CDT gene (e.g., a mutated *C. jejuni* strain). In a further embodiment, the composition may further comprise an adjuvant. Examples of adjuvants include but are not limited to inorganic adjuvants (e.g., aluminum salts (aluminum phosphate and aluminum hydroxide)), organic adjuvants, oil-based adjuvants, and virosomes.

One example of a CDT mutein and a CdtB mutein is *Campylobacter jejuni* 81-176 strain with an insertion mutation at CdtB. Thus, in a particular embodiment, the composition to stimulate a specific immune response in a subject comprises the *Campylobacter jejuni* 81-176 strain with an insertion mutation at CdtB.

In another embodiment, the composition comprises a quantity of a bacterial strain that failed to express CDT or a functional CDT due to a mutation at the gene for CDT (e.g., an insertion mutation at the gene for CdtB). In one embodiment, the composition comprises the *Campylobacter jejuni* 81-176 strain that failed to express an active or functional cytolethal distending toxin (CdtB) due to an insertion mutation at the gene for CdtB.

The present invention also provides a method to elicit a specific immune response in a subject. In one embodiment, the method prevents IBS or reduces a subject's likelihood of developing or having IBS. In another embodiment, the method prevents NUD or reduces a subject's likelihood of developing NUD. In one embodiment, the method comprises providing a composition to elicit a specific immune response as described above and administering the composition to the subject.

Administering the composition to the subject may be performed by any method known in the art, and particularly in vaccination therapy (e.g., injection, infusion). In another embodiment, the composition may be administered more than once; for example, "booster shot(s)" may be administered to the subject.

In another embodiment, the present invention provides a method for diagnosing IBS or determining a subject's likelihood of having IBS. In various embodiments, the IBS is post-infections IBS. In one embodiment, the method comprises detecting the presence or absence of CDT or one or more markers indicating a previous exposure to CDT ("CDT marker") in a subject in need thereof and correlating the presence of CDT or one or more CDT markers with a likely presence of IBS or correlating the absence of CDT or one or more CDT markers with a likely absence of IBS. Not all subjects with the presence of CDT or the presence of one or more markers of CDT will have or develop IBS; however, this method provides an indication on a likelihood of whether the subject has IBS or will develop IBS. A determination of a likely presence of IBS may be further correlated and/or confirmed by other diagnostic methods for IBS, or with symptoms of IBS known in the art. Further, a determination of a likely absence of IBS may also be further correlated and/or confirmed by other diagnostics methods for IBS or symptoms of IBS known in the art to rule out IBS.

In another embodiment, the present invention provides a method for diagnosing NUD or determining a subject's likelihood of having NUD. In various embodiments, the NUD is post-infections NUD. In one embodiment, the method comprises detecting the presence or absence of CDT or one or more markers indicating a previous exposure to CDT ("CDT marker") in a subject in need thereof and correlating the presence of CDT or one or more CDT markers with a likely presence of NUD or correlating the absence of CDT or one or more CDT markers with a likely absence of NUD. Not all subjects with the presence of CDT or the presence of one or more markers of CDT will have or develop NUD; however, this method provides an indication on a likelihood of whether the subject has NUD or will develop NUD. A determination of a likely presence of NUD may be further correlated and/or confirmed by other diagnostic methods for NUD, or with symptoms of NUD known the in the art. Further, a determination of a likely absence of NUD may also be further correlated and/or confirmed by other diagnostics methods for NUD or symptoms of IBS known in the art to rule out NUD.

In further embodiments, the above determinations may be used to direct the treatment for the subject. In one embodiment, a subject with the likely presence of IBS or a likelihood of having IBS may be treated with one or more therapies for IBS. In another embodiment, a subject with the likely presence of NUD may be treated with one or more therapies for NUD. One of ordinary skill in the art will be able to select an available treatment for IBS or NUD based on the diagnosis of IBS or NUD. For example, antibiotics such as rifaximin and neomycin can be used to treat IBS or NUD. Particularly, rifaximin can be used to treat diarrhea-predominant IBS, and a rifaximin/neomycin combination can be used to treat constipation-predominant IBS.

In various embodiments, the CDT markers may be antibodies to CDT or a CDT remnant. Methods of detecting CDT or the one or more CDT markers are known in the art and one of ordinary skill in the art will be able to detect CDT without undue experimentation. In one embodiment, the method comprises detecting the presence or absence of a subunit of CDT or one or more markers of a subunit of CDT. In one embodiment, the subunit is CdtA. In another embodiment the subunit of CDT is CdtB. In another embodiment, the subunit of CDT is CdtC. For example, detecting the presence of CDT, or detecting the presence of one or more CDT markers can be done by contacting a biological sample from the subject to one or more substrates capable of detecting the presence of CDT, or detecting the presence of the one or more CDT markers. In various embodiments, the one or more substrates are the antibodies to CDT, CdtA, CdtB, CdtC and fragments thereof as described herein.

In another embodiment, a method of detecting the presence of CDT, CdtA, CdtB, CdtC or a fragment thereof may be performed by providing a nucleic acid probe that hybridizes under stringent conditions to a nucleic acid (e.g., DNA or RNA) that encodes CDT, CdtA, CdtB, CdtC or a fragment thereof to isolate the nucleic acid that encodes CDT, CdtA, CdtB, CdtC or a fragment thereof from a biological sample from a subject. In various embodiments, the nucleic acid probes may be labeled (e.g., fluorescently labeled). The detection may further comprise amplifying the isolated nucleic acid that encodes CDT, CdtA, CdtB, CdtC or a fragment thereof. The presence of the isolated nucleic acid that encodes CDT, CdtA, CdtB, CdtC or a fragment thereof is correlated with a likelihood that the subject was exposed to CDT. As such, the exposure to CDT can indicate that the patient may have IBS.

In alternative embodiments, the results may be further correlated with further tests or symptoms to arrive at a diagnosis of IBS. An absence of the isolated nucleic acid that encodes CDT, CdtA, CdtB, CdtC or a fragment thereof is correlated with a lower likelihood that the subject was exposed to CDT; alternatively, additional tests may be performed on the subject (e.g., on biological samples from the subject) to further correlate or confirm the results to diagnose whether the subject has IBS. For instance, the subject may be tested for the presence or absence of one or more markers of CDT; for example, the presence or absence of anti-CDT antibodies, as discussed herein. The presence or absence of the anti-CDT antibodies can provide further correlation information for a practitioner to reach a diagnosis of whether the subject has IBS.

In various embodiments, the one or more markers of CDT is an antibody that binds specifically to CDT, CdtA, CdtB, CdtC or a fragment thereof. In one particular embodiment, the one or more markers of CDT is an antibody that binds specifically to CdtB or a fragment thereof. The antibody that binds specifically to CDT, CdtA, CdtB, CdtC or a fragment thereof may be one or more of the antibodies described herein. As such, in one embodiment, the method of diagnosing IBS or post-infectious IBS or determining a likely presence or absence of IBS or PI—IBS in a subject in need thereof, comprises detecting the presence or absence of an antibody that binds specifically to CDT, CdtA, CdtB, CdtC or a fragment thereof in the subject; and correlating the presence of the antibody with a likelihood of having IBS or PI-IBS, or correlating the absence of the antibody with a likelihood of not having IBS or PI-IBS. The determination of whether the subject has antibodies against CDT, CdtA, CdtB, CdtC or a fragment thereof is important for the determination of whether the patient may have IBS. In one embodiment, detecting the presence or absence of the antibody is performed on a biological sample obtained from the subject. In another embodiment, detecting the presence or absence of the antibody is performed on a blood sample obtained from the subject.

One of ordinary skill in the art will readily appreciate methods that can be used to detect the presence or absence of an antibody that binds specifically to CDT, CdtA, CdtB, CdtC or a fragment thereof. These methods include but are not limited to immunohistochemistry, flow cytometry, fluorescence in situ hybridization (FISH), radioimmuno assays, and affinity purification.

In one embodiment, detecting the presence or absence of an antibody that binds specifically to CDT, CdtA, CdtB, CdtC or a fragment thereof may be performed by contacting CDT, CdtA, CdtB, CdtC or a fragment thereof to a biological sample obtained from the subject to isolate the antibody that binds specifically to CDT, CdtA, CdtB, CdtC or a fragment thereof, wherein the isolation of the antibody that binds specifically to CDT, CdtA, CdtB, CdtC or a fragment thereof indicates the presence of the antibody and the lack of isolation of the antibody that binds specifically to CDT, CdtA, CdtB, CdtC or a fragment thereof indicates the lack of the antibody. In various embodiments, the fragment of CDT, CdtA, CdtB, CdtC may be the fragments as described herein (e.g., 17 residue peptide of CdtB). As an example, an affinity matrix comprising CDT, CdtA, CdtB, CdtC or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on the CDT, CdtA, CdtB, CdtC or the fragment thereof the labeled CDT, CdtA, CdtB, CdtC or the fragment thereof can be contacted with a biological sample to allow the antibody (if present) to bind specifically to the labeled CdtA, CdtB, CdtC or fragment thereof. In various embodiments, the labeled CdtA, CdtB, CdtC or fragment thereof can be separated out and analyzed for its binding to the antibody.

In another embodiment, a method of diagnosing IBS, detecting a likelihood of having IBS, or a method of determining the susceptibility of a subject to having IBS, comprises detecting the presence or absence of a host protein with homology to CDT or a subunit of CDT in a subject and correlating the presence of the host protein with a likely presence of IBS or a higher susceptibility to developing IBS or correlating the absence of the host protein with a likely absence of IBS or a lower susceptibility to developing IBS. In certain embodiments, the IBS is PI-IBS. Additional tests may be performed to further correlate or confirm the presence or absence of IBS or PI-IBS or to confirm the higher or lower susceptibility of developing IBS or PI-IBS. In one embodiment, the subunit of CDT is CdtA. In another embodiment the subunit of CDT is CdtB. In another embodiment, the subunit of CDT is CdtC. In one embodiment, the host protein has 100% homology with CDT. In another embodiment, the host protein has at least 80%, 85%, 90%, 95%, 96%, 97%, 98%, or 99% homology with CDT. In one embodiment, the host protein has 100% homology with a subunit of CDT. In another embodiment, the host protein has at least 80%, 85%, 90%, 95%, 96%, 97%, 98%, or 99% homology with the subunit of CDT. In a particular embodiment, the host protein has at least 80%, 85%, 90%, 95%, 96%, 97%, 98%, 99% or 100% homology with CdtB. In other embodiments, the host protein has at least 80%, 85%, 90%, 95%, 96%, 97%, 98%, 99% or 100% homology with 17 contiguous residues of CdtB. In other embodiments, the host protein has at least 80%, 85%, 90%, 95%, 96%, 97%, 98%, 99% or 100% homology with 14, 15, 16, 17, 18, 19, 20, 21 or 22 contiguous residues of CdtB. In various embodiments, the CdtB may be CdtB as disclosed by SEQ ID NO:1 or SEQ ID NO:5. In still other embodiments, the host protein has at least 80%, 85%, 90%, 95%, 96%, 97%, 98%, 99% or 100% homology with 10, 11, 12, 13, 14, 15, 16, or 17 contiguous residues of SEQ ID NO: 3. Methods of detecting the host protein known in the art and one of ordinary skill in the art will be able to detect the host protein without undue experimentation. For example, detecting the presence of the host protein can be done by contacting a biological sample from the subject to one or more substrates capable of detecting the presence of the host protein. In various embodiments, the one or more substrates are the antibodies that bind specifically to CDT, CdtA, CdtB, CdtC and fragments thereof as described herein.

Examples of biological samples include but are not limited to body fluids, whole blood, plasma, stool, intestinal fluids or aspirate, and stomach fluids or aspirate, serum, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method, the biological sample may be whole blood, blood plasma, blood serum, stool, intestinal fluid or aspirate or stomach fluid or aspirate.

In another embodiment, the present invention provides methods of determining whether a subject has small intestine bacterial overgrowth (SIBO) or whether a subject is susceptible to having SIBO. Without wishing to be bound by any particular theory, the inventors believe that an aspect of CDT is its cause of nerve damage to the gut. The nerve damage may cause impairment in the gut's ability to clear bacteria. The poor clearance of bacteria may result in SIBO, and the subject may develop IBS (e.g., experience symptoms of IBS). Thus, the method comprises detecting the presence or absence of CDT or one or more markers indicating a previous exposure to CDT ("CDT marker") in a subject in need thereof and correlating the presence of CDT or one or more CDT markers with a likely presence of SIBO or a higher susceptibility to having SIBO, or correlating the absence of CDT or one or more CDT markers with a likely absence of SIBO or a lower susceptibility to having SIBO. Not all subjects with the presence of CDT or the presence of one or more markers of CDT will have SIBO, however, this method provides an indication on a likelihood of whether the subject has SIBO or an indication on the susceptibility of the subject to having SIBO. A determination of a likely presence of SIBO or higher susceptibility to having SIBO may be further correlated and/or confirmed by other diagnostic methods for SIBO, or with symptoms of SIBO known the in the art. Further, a determination of a likely absence of SIBO or a lower susceptibility to having SIBO may also be further correlated and/or confirmed by other diagnostic methods for SIBO or symptoms of SIBO known in the art to rule out SIBO.

In another embodiment, the present invention provides a method of predicting a subject's response to antibiotic treatment for IBS, or antibiotic prophylaxis to prevent or reduce the likelihood of having IBS. The method comprises, detecting the presence of CDT, or detecting the presence of one or more CDT markers, and correlating the presence of CDT or the one or more CDT markers with a higher likelihood of responding to the antibiotic treatment, correlating the absence of CDT or the one or more CDT markers with a lower likelihood of responding to the antibiotic treatment. Responding to the antibiotic treatment refers to receiving beneficial results from the antibiotic treatment (e.g., symptoms of IBS are alleviated). Detecting the presence of CDT, or detecting the presence of one or more CDT markers can be done by methods known in the art or as described above. Examples of antibiotics used in the treatment for IBS, or antibiotic prophylaxis to prevent or reduce the likelihood of having IBS include but are not limited to non-absorbable antibiotics (e.g., rifaximin, neomycin).

In various embodiments, the present invention provides pharmaceutical compositions including a pharmaceutically acceptable excipient along with a therapeutically effective amount of a CDT inhibitor, CDT neutralizer, and/or a composition to elicit a specific immune response (CDT vaccine) as described above. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, parenteral, or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of an effective CDT inhibitor, CDT neutralizer, and/or a composition to stimulate a specific immune response (CDT vaccine) as described above can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to kits for practicing the methods of the present invention. Examples of kits include kits for diagnosing IBS or a likelihood of having IBS, preventing IBS, reducing the likelihood of developing IBS, treating IBS, determining the presence of SIBO, determining the subject's susceptibility to having SIBO, predicting a subject's response to antibiotic treatment for IBS, predicting a subject's response to antibiotic prophylaxis to prevent or reduce the likelihood of having IBS, and/or diagnosing NUD or a likelihood of having NUD. The kit is an assemblage of materials or components, including at least one of the anti-CDT antibodies, CDT inhibitors, CDT neutralizers, and/or a composition to elicit a specific immune response (CDT vaccine) as described above.

The exact nature of the components configured in the inventive kit depends on its intended purpose. For example, various embodiments are configured for the purposes of preventing IBS, reducing the likelihood of developing IBS, treating IBS, determining the presence of SIBO, determining the subject's susceptibility to having SIBO, predicting a subject's response to antibiotic treatment for IBS, predicting a subject's response to antibiotic prophylaxis to prevent or reduce the likelihood of having IBS, and/or diagnosing NUD or a likelihood of having NUD. In one embodiment, the kit is configured particularly for mammalian subjects. In another embodiment, the kit is configured particularly for human subjects. In further embodiments, the kit is configured for veterinary applications, for subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to prevent IBS, reduce the likelihood of developing IBS, treat IBS, determine the presence of SIBO, determine the subject's susceptibility to having SIBO, predict a subject's response to antibiotic treatment for IBS, predict a subject's response to antibiotic prophylaxis to prevent or reduce the likelihood of having IBS, and/or diagnose NUD or a likelihood of having NUD. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in IBS treatment or antibody treatment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a CDT inhibitor and/or CDT neutralizer, or a composition to elicit a specific immune response, an antibody to detect CDT or a fragment thereof as described above. The packaging material generally has an external label which indicates the contents and/or purpose of the kit and/or its components.

The inventors further discovered the cross reactivity of CdtB antibodies with endogenous factors in uninfected rat ileal tissue by immunohistochemistry, which led to the study of susceptibility to development of IBS via CdtB molecular mimicry as a mechanism in the development of bacterial overgrowth. In this study, we investigated the immune response associated with CdtB in animal and human systems by tracking antibodies that bind CdtB during acute infection and the development of CdtB-associated antibodies as a predictor of IBS in both rats and humans.

Antibodies to cdtB after acute gastroenteritis through molecular mimicry produce an autoantibody to vinculin in IBS. Detection of this antibody is predictive of IBS over IBD and healthy controls. In animals, we have shown that titers of anti-cdtB correlate with the degree of bacterial overgrowth, and without wishing to be bound by any particular theory, we believe that a neuropathy induced by these antibodies is a cause of SIBO.

We demonstrate for the first time that molecular mimicry through autoimmunity may have an important role in the pathophysiology of post-infectious IBS in both rats and humans. Antibodies to cytolethal distending toxin B subunit of C. jejuni cross react with elements of the enteric nervous system and specifically ICC and myenteric ganglia. This interaction appears to create a degree of cellular inflammation and perhaps through effects on gut motor activity, small intestinal bacterial overgrowth since greater antibody titers were predictive of greater abnormalities in small bowel flora. Furthermore, detection of these antibodies in the serum of humans and rats have important diagnostic value.

It has become clear that acute gastroenteritis is a cause of irritable bowel syndrome. From two recent meta-analyses, the incidence of IBS after an outbreak of bacterial gastroenteritis is approximately 10% (Thabane and Halvorsson studies). Two important outbreaks have been most studied including the Walkerton outbreak from Canada and the outbreak in Spain (Mearin et al.). Prior to these studies, investigators had suggested that post-infectious IBS was either a separate entity or a small subset of the total IBS population. However, a recent model using military and the known prospective data on post-infectious IBS combined with CDC data on the incidence of gastroenteritis in the US, now suggests that more than 9% of the entire US population would have IBS from this cause. While modeling can be difficult it at least suggests that acute gastroenteritis could be responsible for a large portion of IBS in the community and may be the major cause.

There have been a number of physiologic observations in subjects with IBS. These include demonstration of visceral hypersensitivity. While many suggest that visceral sensitivity is the basis for the Rome criteria in IBS, ironically, bloating is often noted as the most bothersome symptom in patient study. Based on this symptom, over a decade ago, studies began to suggest that small intestinal bacterial overgrowth (SIBO) may be a feature of IBS. While this concept was initially controversial, two recent large scale studies have confirmed an excess of coliform bacteria in the small intestine of IBS compared to healthy controls (Posserud) and even compared to subjects with other foregut disease (Pyleris). In fact, in subjects with diarrhea predominant IBS, 60% of subjects had culture proven SIBO (Pyleris).

Numerous animal models have been created to study post-infectious IBS. However, some of the more prominently published models have used pathogens that are an uncommon pathogen in IBS and the focus of these models has been the development of visceral hyperalgesia. The most common cause of bacterial gastroenteritis in the US is Campylobacter jejuni and thus, is likely the greatest contributor to the overall incidence of post-infectious IBS in the US. Using this pathogen, a recent rodent model has demonstrated development of altered bowel form, SIBO, reduced ICC and increased intrarectal lymphocytes. These findings mimic the findings in humans with IBS and post-infectious IBS.

While C. jejuni is a common cause of gastroenteritis and important cause of post-infectious IBS, multiple bacterial pathogens have been incriminated in the development of IBS. This suggests either a common host response to this infection or a common toxin. Cytolethal distending toxin is common to almost all bacterial causes of acute gastroenteritis. This toxin has three components (Cdt A, B and C). However, the active toxin is believed to be Cdt B based on in vitro study of effect on HeLa cells. In the rodent model described above, infection of rats with C. jejuni 81-176 with an insertion deletion of CdtB did not result in the full phenotype of post-infectious IBS. Although human studies suggested that the intensity of the acute gastroenteritis was important in the development of IBS, in two acute rodent infection studies, intestinal injury was only marginally altered by the presence or absence of intact CdtB. Thus, Cdt B appeared to have another role in vivo towards the development of IBS.

We demonstrate herein, using an immunohistochemical approach, that CdtB is producing an effect on the host through the production of autoantibodies. Antibodies to CdtB bind to the myenteric neurons and the interstitial cells of Cajal. These autoantibodies are detectable in both rats and humans with post-infectious IBS. In fact, the antibody has a significant diagnostic value in both identifying post-infectious IBS (even in contrast to Crohns and ulcerative colitis) and in predicting the consequence of a small bowel neuropathy (small intestinal bacterial overgrowth) in rats. These data suggest that IBS is an autoimmune disease.

Based on the current evidence, it now seems that post-infectious IBS could account for a majority of IBS in the US population and recent evidence supports that SIBO is common in IBS (Posserud and Pyleris) and may be due to neuromuscular disturbance of the small intestine. However, this study suggests a sequence of events leading to this disturbance that starts with exposure to a bacterial pathogen containing CdtB. The resulting immune response to CdtB produces antibodies that also recognize a host enteric nerve cytosolic protein. The resulting autoantibody and its titer appear to correlate with the degree of SIBO which might be an indirect measure of the neuronal impairment of the small bowel. The degree and presence of SIBO appears to determine the bowel disturbance in this model (the first rat model validation) and in humans (Target 1 and 2) studies.

In conclusion, while not wishing to be bound by any particular theory, we believe that acute gastroenteritis is a major cause of IBS. Herein, we demonstrate that the cytolethal distending toxin is instrumental in the development of IBS through the induction of an antibody and through molecular mimicry one that is autoimmune to an enteric nerve protein and predictive of SIBO. This study may be a major breakthrough in understanding the pathophysiology of IBS.

Accordingly, various embodiments of the present invention are based, at least in part, on these findings.

Diagnosis

Various embodiments provide for a method and a system of diagnosing a gastrointestinal motility disorder, bladder motility disorder, or fibromyalgia.

In various embodiments, the method comprises: providing a biological sample from a subject desiring diagnosis of the gastrointestinal motility disorder, bladder motility disorder, or fibromyalgia, detecting in the biological sample, a presence of anti-vinculin antibodies, and determining a presence or likely presence of the gastrointestinal motility disorder, bladder motility disorder, or fibromyalgia if the presence of anti-vinculin antibodies are detected, or determining an absence or likely absence of the gastrointestinal motility disorder, bladder motility disorder, or fibromyalgia if the absence of anti-vinculin antibodies are detected. In certain embodiments, the method further comprises analyzing the biological sample for the presence or absence of anti-vinculin antibodies.

In various embodiments, the method comprises: providing a biological sample from a subject desiring diagnosis of the gastrointestinal motility disorder, bladder motility disorder, or fibromyalgia, detecting in the biological sample, a level of anti-vinculin antibodies, and determining a presence or likely presence of the gastrointestinal motility disorder, bladder motility disorder, or fibromyalgia if the level of an anti-vinculin antibody is higher than an established control level, or determining the absence or likely absence of the gastrointestinal motility disorder, bladder motility disorder, or fibromyalgia if the level of an anti-vinculin antibody is equal or lower than the established control level. In various embodiments, the established control level is a level of anti-vinculin antibodies within two standard deviations of anti-vinculin antibody levels from subjects without the gastrointestinal motility disorder, bladder motility disorder, or fibromyalgia. In certain embodiments, the method further comprises analyzing the biological sample for a level of anti-vinculin antibodies.

In various embodiments, the method comprises: providing a biological sample from a subject desiring diagnosis of the gastrointestinal motility disorder, bladder motility disorder, or fibromyalgia, detecting in the biological sample, a level of anti-vinculin antibodies, and determining a presence or likely presence of the gastrointestinal motility disorder, bladder motility disorder, or fibromyalgia if the level of anti-vinculin antibodies is significantly higher than an established control level, or determining the absence or likely absence of the gastrointestinal motility disorder, bladder motility disorder, or fibromyalgia if the level of anti-vinculin antibodies is not significantly higher than the established control level. In various embodiments the established control level is a level of anti-vinculin antibodies from subjects without the gastrointestinal motility disorder, bladder motility disorder, or fibromyalgia. In certain embodiments, the method further comprises analyzing the biological sample for a level of anti-vinculin antibodies.

In various embodiments, the system comprises: an isolated biological sample from a subject desiring diagnosis of the gastrointestinal motility disorder, bladder motility disorder, or fibromyalgia, and an assay for detecting in the biological sample, a presence or level of an anti-vinculin antibody.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample, a second reagent (e.g., secondary antibody) to react with the anti-vinculin antibody, and a substrate. In various embodiments, the first reagent is vinculin or a fragment thereof, which will react with the anti-vinculin antibody if present in the biological sample. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of the gastrointestinal motility disorder, bladder motility disorder, or fibromyalgia if the presence of anti-vinculin antibodies is detected, or determining an absence or likely absence of the gastrointestinal motility disorder, bladder motility disorder, or fibromyalgia if the absence of anti-vinculin antibodies is detected. In various embodiments, the machine is a computer. In various embodiments, the computer comprises a display element for displaying whether there is a presence or absence of the gastrointestinal motility disorder, bladder motility disorder, or fibromyalgia.

In various embodiments, the system further comprises a machine for determining a presence or likely presence of the gastrointestinal motility disorder, bladder motility disorder, or fibromyalgia if the level of anti-vinculin antibodies is higher than an established control level, or determining an absence or likely absence of the gastrointestinal motility disorder, bladder motility disorder, or fibromyalgia if the level of anti-vinculin antibodies is equal or lower than the established control level. In various embodiments, the established control level is a level of anti-vinculin antibodies within two standard deviations of anti-vinculin antibody levels from subjects without the gastrointestinal motility disorder, bladder motility disorder, or fibromyalgia. In certain embodiments, the method further comprises analyzing the biological sample for a level of anti-vinculin antibodies.

In various embodiments, the system further comprises a machine for determining a presence or likely presence of the gastrointestinal motility disorder, bladder motility disorder, or fibromyalgia if the level of anti-vinculin antibodies is significantly higher than an established control level, or determining an absence or likely absence of the gastrointestinal motility disorder, bladder motility disorder, or fibromyalgia if the level of anti-vinculin antibodies is not significantly higher than the established control level. In various embodiments the established control level is a level of anti-vinculin antibodies from subjects without the gastrointestinal motility disorder, bladder motility disorder, or fibromyalgia. In certain embodiments, the method further comprises analyzing the biological sample for a level of anti-vinculin antibodies.

In various embodiments, the gastrointestinal motility disorder, bladder motility disorder, or fibromyalgia detected by the method or system is irritable bowel syndrome (IBS), constipation predominant IBS (C-IBS), diarrhea predominant IBS (D-IBS), alternating IBS (A-IBS) (more recently re-named as mixed (M-IBS)), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, interstitial cystitis, leaky gut syndrome, or fibromyalgia. Without being bound to any particular theory, we believe that since vinculin helps cells migrate and adhere to each other and epithelial cells have vinculin, impaired vinculin may allow the gut to be "leaky." In the case of the enteric nervous system, impaired vinculin may impair the enteric nerve network. In various embodiments, the gastrointestinal motility disorder is IBS. In various embodiments, the gastrointestinal motility disorder is GERD. In various embodiments, the gastrointestinal motility disorder is functional dyspepsia.

In certain embodiments, the subject desiring diagnosis of the gastrointestinal motility disorder, bladder motility disorder, or fibromyalgia in accordance to the methods and systems of the present invention may have one or more symptoms indicative of the gastrointestinal motility disorder, bladder motility disorder, or fibromyalgia; for example, bloating, diarrhea, constipation, abdominal pain, fatigue, fibromyalgia pain.

Various embodiments of the present invention provide for a method and a system of distinguishing between IBS and IBD.

The method can comprise providing a biological sample from a subject desiring a diagnosis to distinguish between IBS and IBD, detecting in the biological sample, a presence of anti-vinculin antibodies, and making a diagnosis of IBS if the presence of anti-vinculin antibodies is detected, or making a diagnosis of IBD if the absence of anti-vinculin antibodies is detected. In certain embodiments, the method further comprises analyzing the biological sample for the presence or absence of anti-vinculin antibodies. In certain embodiments, the method further comprises selecting an IBS treatment if IBS is diagnosed, or selecting an IBD treatment if IBD is diagnosed.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is higher than an established control level, or making a diagnosis of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is significantly higher than an established control level, or making a diagnosis of IBD if the level of anti-vinculin antibodies is not significantly higher than the established control level. In various embodiments the established control level is a level of anti-vinculin antibodies from subjects without IBS, IBD or both. In certain embodiments, the method further comprises analyzing the biological sample for a level of anti-vinculin antibodies.

In various embodiments, the system can comprise an isolated biological sample from a subject desiring distinguishing between IBS and IBD, and an assay for detecting in the biological sample, a presence of an anti-vinculin antibody or a level of anti-vinculin antibody to distinguish between IBS and IBD.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies is detected, or determining the presence or likely presence of IBD if the absence of anti-vinculin antibodies is detected. In various embodiments, the machine is a computer. In various embodiments, the computer comprises a display element for displaying whether the patient likely has IBS or IBD.

In various embodiments, the system further comprises a machine for determining a presence or likely presence of IBS if the level of anti-vinculin antibodies is higher than an established control level, or determining a presence or likely presence of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the system further comprises a machine for determining a presence or likely presence of IBS if the level of anti-vinculin antibodies is significantly higher than an established control level, or determining a presence or likely presence of IBD if the level of anti-vinculin antibodies is not significantly higher than the established control level. In various embodiments the established control level is a level of anti-vinculin antibodies from healthy subjects without IBS, IBD or both. In certain embodiments, the method further comprises analyzing the biological sample for a level of anti-vinculin antibodies.

In various embodiments, the machine is a computer. In various embodiments, the computer comprises a display element for displaying whether the patient likely has IBS or IBD.

In various embodiments, the anti-vinculin antibody detected in these methods or systems is an antibody that binds specifically to vinculin.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to SEQ ID NO:7.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 contiguous residues of SEQ ID NO:7.

Contiguous residues of vinculin or SEQ ID NO:7 include those beginning at any amino acid and ending at any amino acid of vinculin or SEQ ID NO:7.

Protein sequence of Vinculin (SEQ ID NO:7):

```
MPVFHTRTIESILEPVAQQISHLVIMHEEGEVDGKAIPDLTAPVAAVQAA
VSNLVRVGKETVQTTEDQILKRDMPPAFIKVENACTKLVQAAQMLQSDPY
SVPARDYLIDGSRGILSGTSDLLLTFDEAEVRKIIRVCKGILEYLTVAEV
VETMEDLVTYTKNLGPGMTKMAKMIDERQQELTHQEHRVMLVNSMNTVKE
LLPVLISAMKIFVTTKNSKNQGIEEALKNRNFTVEKMSAEINEIIRVLQL
TSWDEDAWASKDTEAMKRALASIDSKLNQAKGWLRDPSASPGDAGEQAIR
QILDEAGKVGELCAGKERREILGTCKMLGQMTDQVADLRARGQGSSPVAM
QKAQQVSQGLDVLTAKVENAARKLEAMTNSKQSIAKKIDAAQNWLADPNG
GPEGEEQIRGALAEARKIAELCDDPKERDDILRSLGEISALTSKLADLRR
QGKGDSPEARALAKQVATALQNLQTKTNRAVANSRPAKAAVHLEGKIEQA
QRWIDNPTVDDRGVGQAAIRGLVAEGHRLANVMMGPYRQDLLAKCDRVDQ
LTAQLADLAARGEGESPQARALASQLQDSLKDLKARMQEAMTQEVSDVFS
DTTTPIKLLAVAATAPPDAPNREEVFDERAANFENHSGKLGATAEKAAAV
GTANKSTVEGIQASVKTARELTPQVVSAARILLRNPGNQAAYEHFETMKN
QWIDNVEKMTGLVDEAIDTKSLLDASEEAIKKDLDKCKVAMANIQPQMLV
AGATSIARRANRILLVAKREVENSEDPKFREAVKAASDELSKTISPMVMD
AKAVAGNISDPGLQKSFLDSGYRILGAVAKVREAFQPQEPDFPPPPPDLE
QLRLTDELAPPKPPLPEGEVPPPRPPPPEEKDEEFPEQKAGEVINQPMMM
AARQLHDEARKWSSKGNDIIAAAKRMALLMAEMSRLVRGGSGTKRALIQC
AKDIAKASDEVTRLAKEVAKQCTDKRIRTNLLQVCERIPTISTQLKILST
VKATMLGRTNISDEESEQATEMLVHNAQNLMQSVKETVREAEAASIKIRT
DAGFTLRWVRKTPWYQ
```

In various embodiments, detecting the presence or absence of the antibody is performed on a biological sample obtained from the subject. In another embodiment, detecting the presence or absence of the antibody is performed on a blood, serum, or stool sample obtained from the subject. One of ordinary skill in the art will readily appreciate methods and systems that can be used to detect the presence or absence of an antibody that binds specifically to vinculin, SEQ ID NO:7 or a fragment thereof. These methods and systems include but are not limited to ELISA, immunohistochemistry, flow cytometry, fluorescence in situ hybridization (FISH), radioimmuno assays, and affinity purification.

In various embodiments, vinculin, SEQ ID NO:7 or a fragment thereof (as described above) is used as a substrate or reagent (e.g., collector, trap) to bind anti-vinculin antibodies (if present).

In certain embodiments, detecting the presence or absence of an antibody that binds specifically to vinculin, SEQ ID NO:7 or a fragment thereof may be performed by contacting vinculin, SEQ ID NO:7 or a fragment thereof to a biological sample obtained from the subject to isolate the antibody that binds specifically to vinculin, SEQ ID NO:7 or a fragment thereof, wherein the isolation of the antibody that binds specifically to vinculin, SEQ ID NO:7 or a fragment thereof indicates the presence of the antibody and the lack of isolation of the antibody that binds specifically to vinculin, SEQ ID NO:7 or a fragment thereof indicates the lack of the antibody. In various embodiments, the fragment of vinculin or SEQ ID NO:7 may be the fragments as described herein. As an example, an affinity matrix comprising vinculin, SEQ ID NO:7 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO:7 or a fragment thereof; the labeled vinculin, SEQ ID NO:7 or a fragment thereof can be contacted with a biological sample to allow the antibody (if present) to bind specifically to the labeled vinculin, SEQ ID NO:7 or a fragment thereof. In various embodiments, the labeled vinculin, SEQ ID NO:7 or a fragment thereof can be separated out and analyzed for its binding to the antibody.

Therapy

Various embodiments provide for a method of selecting a therapy for a gastrointestinal motility disorder, bladder motility disorder, or fibromyalgia for a subject in need thereof. In various embodiments, the method comprises: detecting the presence of anti-vinculin antibodies; and selecting a therapy to treat the gastrointestinal motility disorder, bladder motility disorder, or fibromyalgia. Selecting a therapy as used herein, includes but is not limited to selecting, choosing, prescribing, advising, recommending, instructing, or counseling the subject with respect to the treatment. In various embodiments, the method further comprises administering the therapy to treat the gastrointestinal motility disorder, bladder motility disorder, or fibromyalgia. In various embodiments, the therapy is a therapy as described herein. In various embodiments, the available therapy comprises administering a course of antibiotic therapy to treat the gastrointestinal motility disorder, bladder motility disorder, or fibromyalgia. In various embodiments, the therapy is an available therapy in the prior art.

In various embodiments, detecting the presence of anti-vinculin antibodies can be performed as described by the methods or systems of the present invention.

In various embodiments, the subject can be a subject presenting one or more symptoms of gastrointestinal motility disorder, bladder motility disorder, or fibromyalgia; for example, as discussed herein.

In various embodiments, the method comprises: detecting the presence of anti-vinculin antibodies; and selecting a course of antibiotic therapy to treat gastrointestinal motility disorder, bladder motility disorder, or fibromyalgia. In various embodiments, the method further comprises administering the course of antibiotic therapy treat the gastrointestinal motility disorder, bladder motility disorder, or fibromyalgia.

In various embodiments, the gastrointestinal motility disorder, bladder motility disorder, or fibromyalgia can be part of irritable bowel syndrome (IBS), C-IBS, D-IBS, A-IBS (also known as M-IBS), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, interstitial cystitis, leaky gut syndrome, or fibromyalgia. In various embodiments, the gastrointestinal motility disorder is IBS. In certain embodiments, the gastrointestinal motility disorder is GERD. In certain embodiments, the gastrointestinal motility disorder is functional dyspepsia.

Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paramomycin.

Various embodiments provide for methods for treating a gastrointestinal motility disorder, bladder motility disorder, or fibromyalgia. In various embodiments, the gastrointestinal motility disorder, bladder motility disorder, or fibromyalgia treated can be irritable bowel syndrome (IBS), C-IBS, D-IBS, A-IBS (also known as M-IBS), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, interstitial cystitis, leaky gut syndrome, or fibromyalgia. In various embodiments, the gastrointestinal motility disorder is IBS. In certain embodiments, the gastrointestinal motility disorder is GERD. In certain embodiments, the gastrointestinal motility disorder is functional dyspepsia.

In various embodiments, the method can comprise providing an anti-vinculin antibody neutralizing or inhibiting agent and administering the anti-vinculin antibody neutralizing or inhibiting agent to a subject in need thereof to neutralize or inhibit the anti-vinculin antibody.

In various embodiments, the anti-vinculin antibody neutralizing or inhibiting agent is a polypeptide capable of binding to the anti-vinculin antibody and neutralizing or inhibiting its function.

In various embodiments, the anti-vinculin antibody neutralizing or inhibiting agent is a polypeptide capable of binding to an antigen binding site of the anti-vinculin antibody. While not wishing to be bound by any particular theory, the inventors believe that these polypeptides can serves as a decoy to the anti-vinculin antibody. In various embodiments, the polypeptides are CDT pentapeptides as disclosed by Lucchese and Delfino (*Developing an anti-Campylobacter jejuni vaccine*. Immunopharmacology and Immunotoxicology, 2012; Early Online: 1-6), which is hereby incorporated by reference in its entirety as though fully set forth.

In various embodiments, the anti-vinculin antibody neutralizing or inhibiting agent is a small molecule capable of binding to the anti-vinculin antibody and neutralizing or inhibiting its function.

In various embodiments, the anti-vinculin antibody neutralizing or inhibiting agent is a small molecule capable of binding to an antigen binding site of the anti-vinculin antibody.

In various embodiments, the method can comprise providing an agent to change vinculin from an inactive state to an active state; and administering the agent to a subject in need thereof to treat the gastrointestinal motility disorder, bladder motility disorder, or fibromyalgia.

In various embodiments, the agent to change vinculin from an inactive state to an active state is a small molecule capable of activating vinculin.

In various embodiments, the method can comprise providing a vinculin agonist; and administering the vinculin agonist to a subject in need thereof to treat the gastrointestinal motility disorder, bladder motility disorder, or fibromyalgia. In certain embodiments, the vinculin agonist can be vinculin activating peptide (VAP) as disclosed by Nelson et al., *Vinculin Activators Target Integrins from Within the Cell to Increase Melanoma Sensitivity to Chemotherapy*, Mol Cancer Res June 2011 9; 712 (published online Apr. 1, 2011), which is hereby incorporated by reference in its entirety as though fully set forth. In various embodiments, the VAP can be residues 500-633 of invasin protein IpaA of *Shigella*.

The protein sequence of IpaA of *Shigella*:

```
                                              (SEQ ID NO: 12)
MHNVNNTQAP  TFLYKATSPS  STEYSELKSK  ISDIHSSQTS

LKTPASVSEK  ENFATSFNQK  CLDFLFSSSG  KEDVLRSIYS

NSMNAYAKSE  ILEFSNVLYS  LVHQNGLNFE  NEKGLQKIVA

QYSELIIKDK  LSQDSAFGPW  SAKNKKLHQL  RQNIEHRLAL

LAQQHTSGEA  LSLGQKLLNT  EVSSFIKNNI  LAELKLSNET

VSSLKLDDLV  DAQAKLAFDS  LRNQRKNTID  SKGFGIGKLS

RDLNTVAVFP  ELLRKVLNDI  LEDIKDSHPI  QDGLPTPPED

MPDGGPTPGA  NEKTSQPVIH  YHINNDNRTY  DNRVFDNRVY

DNSYHENPEN  DAQSPTSQTN  DLLSRNGNSL  LNPQRALVQK

VTSVLPHSIS  DTVQTFANNS  ALEKVFNHTP  DNSDGIGSDL

LTTSSQERSA  NNSLSRGHRP  LNIQNSSTTP  PLHPEGVTSS

NDNSSDTTKS  SASLSHRVAS  QINKFNSNTD  SKVLQTDFLS

RNGDTYLTRE  TIFEASKKVT  NSLSNLISLI  GTKSGTQERE

LQEKSKDITK  STTEHRINNK  LKVTDANIRN  YVTETNADTI

DKNHAIYEKA  KEVSSALSKV  LSKIDDTSAE  LLTDDISDLK

NNNDITAENN  NIYKAAKDVT  TSLSKVLKNI  NKD
```

In various embodiments, the method can comprise providing a vinculin activator; and administering the vinculin activator to a subject in need thereof to treat the gastrointestinal motility disorder, bladder motility disorder, or fibromyalgia. In certain embodiments, the vinculin activator can be talin, f-actin, a-catenin, or combinations thereof.

Various embodiments provide for a method of treating or inhibiting the progression of colon polyps or malignancy. It has been seen that there are less polyps in patients with IBS. As such, anti-vinculin antibodies or agents that block vinculin can decrease the progression of colon polyps or malignancy.

In various embodiments, the method can comprise providing an agent to change vinculin from an active state to an inactive state; and administering the agent to a subject in need thereof to treat or inhibit the progression of colon polyps or malignancy.

In various embodiments, the agent to change vinculin from an active state to an inactive state is a small molecule capable of inactivating vinculin.

In various embodiments, the method can comprise providing a vinculin antagonist; and administering the vinculin antagonist to a subject in need thereof to treat or inhibit the progression of colon polyps or malignancy.

In various embodiments, the method can comprise providing a vinculin inactivator; and administering the vinculin inactivator to a subject in need thereof to treat or inhibit the progression of colon polyps or malignancy.

In various embodiments, the method can comprise providing an anti-vinculin antibody capable of inhibiting the function of vinculin; and administering the anti-vinculin antibody to the subject to treat or inhibit the progression of colon polyps or malignancy.

In various embodiments, the present invention provides pharmaceutical compositions including a pharmaceutically acceptable excipient along with a therapeutically effective amount of the agents described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

A newly validated animal model of post-infectious IBS (PI-IBS) based on infection with *Campylobacter jejuni* suggests that AGE precipitates PI-IBS, leading to significant alterations in small bowel microbial colonization. Using this model, it was determined that the development of IBS-like phenotypes in these animals was dependent on a specific toxin, cytolethal distending toxin B (CdtB). Significantly, the development of IBS-like phenotypes in this animal model was mitigated in the absence of CdtB. In a subsequent series of experiments, we found that, through molecular mimicry, host antibodies to CdtB react with the host protein vinculin in the neuromuscular apparatus of the gut. The presence of circulating antibodies to CdtB and vinculin in the animal model is associated with the development of altered gut microbial populations and changes in the gut neuromuscular apparatus, including significant reductions in the numbers of interstitial cells of Cajal (ICC) in the deep muscular plexus.

Based on these new pathophysiologic mechanisms underlying IBS, we assessed the prevalence of anti-CdtB and anti-vinculin antibodies and CdtB in a large cohort of IBS patients and non-IBS controls to validate biomarkers for IBS based on detection of circulating antibodies to vinculin and CdtB in humans.

Described herein, we describe a biomarker for D-IBS based on, without wishing to being bound by any specific theory, a pathophysiologic mechanism of post-infectious IBS and the subsequent development of autoantibodies to vinculin in the host. The test appears specific not only for diagnosing D-IBS but in the workup of chronic diarrhea, can differentiate D-IBS subjects from those with IBD.

While the rate of developing IBS after a single acute gastroenteritis is approximately 10%, military deployment data and mathematical modeling suggest that PI-IBS could account for a large portion of IBS in the US. PI-IBS occurs primarily, though not exclusively, after bacterial infections such as *Campylobacter jejuni, Salmonella, E. coli* and *Shigella*. One toxin commonly produced by all four of these organisms is cytolethal distending toxin, a heterotrimeric complex of three subunits, CdtA, CdtB, and CdtC, of which CdtB is the active subunit.

A validated animal model developed using *C. jejuni* 81-176 has been shown to exhibit an IBS-like phenotype. Significantly, these rats exhibit changes in stool form, small intestinal bacterial overgrowth (SIBO) and the increased rectal intra-epithelial lymphocytes characteristic of humans with IBS. In this model the effects appeared to be due to changes in gut neuroanatomy, with a notable reduction in interstitial cells of Cajal. Further, rats infected with a mutant *C. jejuni* strain lacking CdtB exhibited a significantly mitigated IBS-like phenotype compared to those infected with wild-type *C. jejuni*, suggesting that CdtB was important in the development of IBS in this model. Through a series of immunologic experiments in this model, it was determined that CdtB appeared not to simply be acting through direct toxicity but rather through the cross-reaction of antibodies to CdtB with the host protein vinculin. Levels of circulating antibodies to CdtB and vinculin correlated with the development and levels of SIBO in these animals.

Vinculin is a 117-kDa cytoplasmic actin-binding protein that is a key component of both focal adhesions and adherens junctions, forming the link between integrins or cadherins respectively and the actin cytoskeleton. Furthermore, vinculin appears important in neuronal cell motility and contractility and cardiac formation, as evidenced by the neural tube, myocardial and endocardial defects in vinculin knockout mice, as well as stress-induced cardiomyopathy in heterozygous mutants. In a recently published study, Cdt from *Helicobacter pullorum* has been shown to target vinculin in intestinal epithelial cells, triggering an atypical delocalization of vinculin from focal adhesions coupled with decreased cellular adherence. Another study demonstrated that vinculin is used by the IpA toxin of *Shigella* to achieve cell entry.

Based on the pathophysiologic observations in this animal model, we hypothesized that exposure to CdtB led to detectable immunity to CdtB and autoimmunity to vinculin based on molecular mimicry. In this study, we evaluate whether levels of these antibodies serve as a biomarker for D-IBS in humans for the first time using a large number of IBS and non-IBS patients. We observe that plasma antibodies to vinculin and CdtB were elevated in D-IBS compared to healthy controls, subjects with celiac disease, and subjects with IBD such that the biomarkers appeared to be able to distinguish D-IBS from all non-IBS. Based on ideal cutoff titers, the test has a high specificity for identifying D-IBS compared to IBD. Since tTG is a robust test for celiac disease, in the workup of chronic diarrhea, a real unmet need is a biomarker that could reliably distinguish IBS from IBD. Interestingly anti-CdtB, but not anti-vinculin, was high in celiac disease as well. Another significant unmet need for celiac disease is a test that readily distinguishes functional symptoms from ongoing gluten exposure. Studies suggest that after gluten exposure, IBS is the second most common cause of non-responsive celiac disease, and therefore, a test that could distinguish between these causes of symptoms would be useful clinically.

Based on these results, circulating anti-CdtB and anti-vinculin antibodies are biomarkers for D-IBS and offer some unique perspectives on the pathophysiology of PI-IBS. While not wishing to be bound by any particular theory, first, these are biomarkers based on a mechanism for the development of IBS which may involve alterations to the enteric nervous system and gut motility. Secondly, they represent the first opportunity to make IBS a diagnosis of inclusion rather than a "diagnosis of exclusion". Since not all D-IBS subjects test positive for these biomarkers, it is also possible that these antibodies identify a subgroup of IBS for which a mechanism and therapies could be developed. Finally, it suggests that IBS may have an organic basis. As a biomarker, measurements of anti-vinculin and anti-CdtB antibodies could help to identify D-IBS without excessive investigation and may help to target investigations in those where the test is negative.

While the test has a lower specificity for identifying D-IBS compared to celiac disease, concomitant testing with anti-tTG should compensate for this.

In conclusion, this study validates the presence of anti-vinculin and anti-CdtB as blood based biomarkers that separate D-IBS from IBD and healthy controls using a large scale prospective multicenter trial. Anti-vinculin and anti-CdtB antibodies also appear part of the pathophysiology of post-infectious IBS and may identify a subgroup of D-IBS for directed therapies. Most importantly, this appears to be an important step in determining organic bases for IBS.

Thus, various embodiments of the invention are based, at least in part, on these additional findings.

Distinguishing IBS from IBD and Celiac Disease

Various embodiments of the present invention provide for methods, assays and systems of distinguishing IBS from IBD and Celiac disease.

The method can comprise providing a biological sample from a subject desiring a diagnosis to distinguish IBS from IBD and Celiac disease, detecting in the biological sample, a presence of anti-vinculin antibodies, and making a diagnosis of IBS if the presence of anti-vinculin antibodies is detected, or making a diagnosis of IBD, suspicion of IBD, Celiac disease or suspicion of Celiac disease if there is an absence of anti-vinculin antibodies. In certain embodiments, the method further comprises analyzing the biological sample for the presence or absence of anti-vinculin antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

In various embodiments, the method can comprise providing a biological sample from a subject desiring a diagnosis to distinguish IBS from IBD and Celiac disease, detecting in the biological sample, a level of anti-vinculin antibodies, and making a diagnosis of IBS if the level of anti-vinculin antibodies is higher than an established control level, or making a diagnosis of IBD, suspicion of IBD, Celiac disease, or suspicion of Celiac disease if the level of anti-vinculin antibodies is equal or lower than the established control level. In various embodiments, the established control level is a level of anti-vinculin antibodies within two standard deviations of anti-vinculin antibody levels from healthy subjects without IBS, IBD, Celiac disease or combinations thereof. In certain embodiments, the method further comprises analyzing the biological sample for a level of anti-vinculin antibodies.

In various embodiments, the method can comprise providing a biological sample from a subject desiring a diagnosis to distinguish IBS from IBD and Celiac disease, detecting in the biological sample, a level of anti-vinculin antibodies, and making a diagnosis of IBS if the level of anti-vinculin antibodies is significantly higher than an established control level, or making a diagnosis of IBD, suspicion of IBD, Celiac disease or suspicion of Celiac disease if the level of anti-vinculin antibodies is not significantly higher than the established control level. In various embodiments, the established control level is a level of anti-vinculin antibodies from subjects without IBS, IBD, Celiac disease or combinations thereof. In certain embodiments, the method further comprises analyzing the biological sample for a level of anti-vinculin antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

The method can comprise providing a biological sample from a subject desiring a diagnosis to distinguish IBS from IBD and Celiac disease, detecting in the biological sample, a presence of anti-CdtB antibodies, and making a diagnosis of IBS if the presence of anti-CdtB antibodies is detected, or making a diagnosis of IBD, suspicion of IBD, Celiac disease or suspicion of Celiac disease if there is an absence of anti-CdtB antibodies. In certain embodiments, the method further comprises analyzing the biological sample for the presence or absence of anti-CdtB antibodies. In certain embodiments, the method further comprises selecting an IBS treatment if IBS is diagnosed, selecting an IBD treatment if IBD is diagnosed or suspected, or selecting a Celiac treatment if Celiac disease is diagnosed or suspected.

In various embodiments, the method can comprise providing a biological sample from a subject desiring a diagnosis to distinguish IBS from IBD and Celiac disease, detecting in the biological sample, a level of anti-CdtB antibodies, and making a diagnosis of IBS if the level of anti-CdtB antibodies is higher than an established control level, or making a diagnosis of IBD, suspicion of IBD, Celiac disease or suspicion of Celiac disease if the level of anti-CdtB antibodies is equal or lower than the established control level. In various embodiments, the established control level is a level of anti-CdtB antibodies within two standard deviations of anti-CdtB antibody levels from healthy subjects without IBS, IBD, Celiac disease or combinations thereof. In certain embodiments, the method further comprises analyzing the biological sample for a level of anti-CdtB antibodies. In certain embodiments, the method further comprises selecting an IBS treatment if IBS is diagnosed, selecting an IBD treatment if IBD is diagnosed or suspected, or selecting a Celiac disease treatment of Celiac disease is diagnosed or suspected.

In various embodiments, the method can comprise providing a biological sample from a subject desiring a diagnosis to distinguish IBS from IBD and Celiac disease, detecting in the biological sample, a level of anti-CdtB antibodies, and making a diagnosis of IBS if the level of anti-CdtB antibodies is significantly higher than an established control level, or making a diagnosis of IBD, suspicion of IBD, Celiac disease or suspicion of Celiac disease if the level of anti-CdtB antibodies is not significantly higher than the established control level. In various embodiments the established control level is a level of anti-CdtB antibodies from subjects without IBS, IBD, Celiac disease or combinations thereof. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish IBS from IBD and Celiac disease, detecting in the biological sample, a presence of anti-vinculin and anti-CdtB antibodies, and making a diagnosis of IBS if the presence of anti-vinculin and anti-CdtB antibodies are detected, or making a diagnosis of IBD, suspicion of IBD, Celiac disease or suspicion of Celiac disease if there are an absence of anti-vinculin and anti-CdtB antibodies. In certain embodiments, the method further comprises analyzing the biological sample for the presence or absence of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac treatment if Celiac disease is diagnosed or suspected.

In various embodiments, the method can comprise providing a biological sample from a subject desiring a diagnosis to distinguish IBS from IBD and Celiac disease, detecting in the biological sample, a level of anti-vinculin and anti-CdtB antibodies, and making a diagnosis of IBS if the levels of anti-vinculin and anti-CdtB antibodies are higher than an established control level, or making a diagnosis of IBD, suspicion of IBD, Celiac disease or suspicion of Celiac disease if the levels of anti-vinculin and anti-CdtB antibodies are equal or lower than the established control levels. In various embodiments, the established control levels are levels of anti-vinculin and anti-CdtB antibodies within two standard deviations of anti-vinculin and anti-CdtB antibody levels from healthy subjects without IBS, IBD, Celiac disease or combinations thereof. In certain embodiments, the method further comprises analyzing the biological sample levels of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac disease treatment if Celiac disease is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the level of anti-vinculin and anti-CdtB antibodies is significantly higher than an established control level, or making a diagnosis of IBD, suspicion of IBD, Celiac disease or suspicion of Celiac disease if the level of anti-vinculin and anti-CdtB antibodies is not significantly higher than the established control levels. In various embodiments the established control levels are levels of anti-vinculin and anti-CdtB antibodies from subjects without IBS, IBD, Celiac disease or combinations thereof. In certain embodiments, the method further comprises analyzing the biological sample for levels of anti-vinculin and anti-CdtB antibodies. In certain embodiments, the method further comprises selecting an IBS treatment if IBS is diagnosed, selecting an IBD treatment if IBD is diagnosed or suspected, or selecting a Celiac disease treatment if Celiac disease is diagnosed or suspected.

In various embodiments, the system can comprise an isolated biological sample from a subject desiring distinguishing IBS from IBD and Celiac disease, and an assay for detecting in the biological sample, a presence of an anti-vinculin antibody or a level of anti-vinculin antibody to distinguish IBS from IBD and Celiac disease.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, if a diagnosis or suspicion of IBD is made, it can be further correlated with IBD symptoms to further confirm IBD. In other embodiments, additional IBD testing can be done to further confirm IBD.

In various embodiments, if a diagnosis or suspicion of Celiac disease is made, it can be further correlated with Celiac disease symptoms to further confirm Celiac disease. In other embodiments, additional celiac disease testing can be done to further confirm Celiac disease; for example, measurement of serum tissue transglutaminase.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies, anti-CdtB antibodies or both is detected, or determining the presence or likely presence of IBD or Celiac disease if there is an absence of anti-vinculin antibodies, anti-CdtB antibodies or both. In various embodiments, the machine is a computer. In various embodiments, the computer comprises a display element for displaying whether the patient likely has IBS, IBD or Celiac disease.

In various embodiments, the system further comprises a machine for determining a presence or likely presence of IBS if the level of anti-vinculin antibodies, anti-CdtB antibodies, or both is higher than an established control level(s), or determining a presence or likely presence of IBD if the level of anti-vinculin antibodies, anti-CdtB antibodies, or both is equal or lower than the established control level(s). In various embodiments, the established control level is a level of anti-vinculin antibodies, anti-CdtB antibodies, or both within two standard deviations of the level of anti-vinculin antibodies, anti-CdtB antibodies, or both from healthy subjects without IBS, IBD, Celiac disease or combinations thereof. In certain embodiments, the method further comprises analyzing the biological sample for a level of anti-vinculin antibodies.

In various embodiments, the system further comprises a machine for determining a presence or likely presence of IBS if the level of anti-vinculin antibodies, anti-CdtB antibodies, or both is significantly higher than an established control level, or determining a presence or likely presence of IBD if the level of anti-vinculin antibodies, anti-CdtB antibodies, or both is not significantly higher than the established control level. In various embodiments the established control level is a level of anti-vinculin antibodies, anti-CdtB antibodies, or both from healthy subjects without IBS, IBD, Celiac disease or combinations thereof. In certain embodiments, the method further comprises analyzing the biological sample for a level of anti-vinculin antibodies, anti-CdtB antibodies, or both.

In various embodiments, the machine is a computer. In various embodiments, the computer comprises a display element for displaying whether the patient likely has IBS, IBD or Celiac disease.

Various embodiments provide for treating IBS in a subject who may have IBS, IBD or Celiac disease. The method comprises providing an IBS therapy and administering the IBS therapy to a subject diagnosed with IBS using the methods of the present invention. That is, the subject has been diagnosed with IBS via the detection of the presence of anti-vinculin and anti-CdtB antibodies in accordance with the methods of the present invention as discussed herein.

In various embodiments, the IBS therapy is a therapy as described herein. In various embodiments, the IBS therapy comprises administering a course of antibiotic therapy to treat IBS. In various embodiments, the IBS therapy is an available therapy in the prior art. In various embodiments, the IBS therapy is a course of antibiotic therapy as described herein.

In various embodiments, the IBS treated can be C-IBS, D-IBS, A-IBS (also known as M-IBS), or post-infectious irritable bowel syndrome (PI-IBS). In particular embodiments, the IBS is D-IBS.

Distinguishing Between IBS and IBD

Various embodiments of the present invention provide for methods, assays and systems of distinguishing between IBS and IBD.

The method can comprise providing a biological sample from a subject desiring a diagnosis to distinguish between IBS and IBD, detecting in the biological sample, a presence of anti-vinculin antibodies, and making a diagnosis of IBS if the presence of anti-vinculin antibodies is detected, or making a diagnosis of IBD or suspicion of IBD if there is an absence of anti-vinculin antibodies. In certain embodiments, the method further comprises analyzing the biological sample for the presence or absence of anti-vinculin antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is higher than an established control level, or making a diagnosis of IBD or suspicion of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is significantly higher than an established control level, or making a diagnosis of IBD or suspicion of IBD if the level of anti-vinculin antibodies is not significantly higher than the established control level. In various embodiments, the established control level is a level of anti-vinculin antibodies from subjects without IBS, IBD or both. In certain embodiments, the method further comprises analyzing the biological sample for a level of anti-vinculin antibodies. In certain embodiments, the method further comprises selecting an IBS treatment if IBS is diagnosed, or selecting an IBD treatment if IBD is diagnosed or suspected.

The method can comprise providing a biological sample from a subject desiring a diagnosis to distinguish between IBS and IBD, detecting in the biological sample, a presence of anti-CdtB antibodies, and making a diagnosis of IBS if the presence of anti-CdtB antibodies is detected, or making a diagnosis of IBD or suspicion of IBD if there is an absence of anti-CdtB antibodies. In certain embodiments, the method further comprises analyzing the biological sample for the presence or absence of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-CdtB antibodies, and making a diagnosis of IBS if the level of anti-CdtB antibodies is higher than an established control level, or making a diagnosis of IBD or suspicion of IBD if the level of anti-CdtB antibodies is equal or lower than the established control level. In various embodiments, the established control level is a level of anti-CdtB antibodies within two standard deviations of anti-CdtB antibody levels from healthy subjects without IBS, IBD or both. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-CdtB antibodies, and making a diagnosis of IBS if the level of anti-CdtB antibodies is significantly higher than an established control level, or making a diagnosis of IBD or suspicion of IBD if the level of anti-CdtB antibodies is not significantly higher than the established control level. In various embodiments the established control level is a level of anti-CdtB antibodies from subjects without IBS, IBD or both. In certain embodiments, the method further comprises analyzing the biological sample for a level of anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a presence of anti-vinculin and anti-CdtB antibodies, and making a diagnosis of IBS if the presence of anti-vinculin and anti-CdtB antibodies is detected, or making a diagnosis of IBD or suspicion of IBD if there are an absence of anti-vinculin and anti-CdtB antibodies. In certain embodiments, the method further comprises analyzing the biological sample for the presence or absence of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the levels of anti-vinculin and anti-CdtB antibodies are higher than an established control level, or making a diagnosis of IBD or suspicion of IBD if the levels of anti-vinculin and anti-CdtB antibodies are equal or lower than the established control levels. In various embodiments, the established control levels are levels of anti-vinculin and anti-CdtB antibodies within two standard deviations of anti-vinculin and anti-CdtB antibody levels from healthy subjects without IBS, IBD or both. In certain embodiments, the method further comprises analyzing the biological sample levels of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the method can comprise providing a biological sample from a subject desiring a diagnosis to distinguish between IBS and IBD, detecting in the biological sample, a level of anti-vinculin and anti-CdtB antibodies, and making a diagnosis of IBS if the level of anti-vinculin and anti-CdtB antibodies is significantly higher than an established control level, or making a diagnosis of IBD or suspicion of IBD if the level of anti-vinculin and anti-CdtB antibodies is not significantly higher than the established control levels. In various embodiments the established control levels are levels of anti-vinculin and anti-CdtB antibodies from subjects without IBS, IBD or both. In certain embodiments, the method further comprises analyzing the biological sample for levels of anti-vinculin and anti-CdtB antibodies. In certain embodiments, the method further comprises selecting an IBS treatment if IBS is diagnosed, or selecting an IBD treatment if IBD is diagnosed or suspected.

In various embodiments, the system can comprise an isolated biological sample from a subject desiring distinguishing between IBS and IBD, and an assay for detecting in the biological sample, a presence of an anti-vinculin antibody or a level of anti-vinculin antibody to distinguish between IBS and IBD.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, if a diagnosis or suspicion of IBD is made, it can be further correlated with IBD symptoms to further confirm IBD. In other embodiments, additional IBD testing can be done to further confirm IBD.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies, anti-CdtB antibodies or both is detected, or determining the presence or likely presence of IBD if there is an absence of anti-vinculin antibodies, anti-CdtB antibodies or both. In various embodiments, the machine is a computer. In various embodiments, the computer comprises a display element for displaying whether the patient likely has IBS or IBD.

In various embodiments, the system further comprises a machine for determining a presence or likely presence of IBS if the level of anti-vinculin antibodies, anti-CdtB antibodies, or both is higher than an established control level(s), or determining a presence or likely presence of IBD if the level of anti-vinculin antibodies, anti-CdtB antibodies, or both is equal or lower than the established control level(s). In various embodiments, the established control level is a level of anti-vinculin antibodies, anti-CdtB antibodies, or both within two standard deviations of the level of anti-vinculin antibodies, anti-CdtB antibodies, or both from healthy subjects without IBS, IBD or both. In certain embodiments, the method further comprises analyzing the biological sample for a level of anti-vinculin antibodies.

In various embodiments, the system further comprises a machine for determining a presence or likely presence of IBS if the level of anti-vinculin antibodies, anti-CdtB antibodies, or both is significantly higher than an established control level, or determining a presence or likely presence of IBD if the level of anti-vinculin antibodies, anti-CdtB antibodies, or both is not significantly higher than the established control level. In various embodiments the established control level is a level of anti-vinculin antibodies, anti-CdtB antibodies, or both from healthy subjects without IBS, IBD or both. In certain embodiments, the method further comprises analyzing the biological sample for a level of anti-vinculin antibodies, anti-CdtB antibodies, or both.

In various embodiments, the machine is a computer. In various embodiments, the computer comprises a display element for displaying whether the patient likely has IBS or IBD.

Diagnosis of IBS

Various embodiments provide for methods, assays and systems of diagnosing or identifying IBS in a subject.

In various embodiments, the method comprises: providing a biological sample from a subject desiring diagnosis of IBS, detecting in the biological sample, a presence of anti-vinculin and anti-CdtB antibodies, and determining a presence or likely presence of IBS if the presence of anti-vinculin and anti-CdtB antibodies are detected, or determining an absence or likely absence of IBS if the absence of anti-vinculin and anti-CdtB antibodies are detected. In certain embodiments, the method further comprises analyzing the biological sample for the presence or absence of anti-vinculin and anti-CdtB antibodies.

In various embodiments, the method comprises: providing a biological sample from a subject desiring diagnosis of IBS, detecting in the biological sample, a level of anti-vinculin and anti-CdtB antibodies, and determining a presence or likely presence of IBS if the level of an anti-vinculin and anti-CdtB antibody is higher than an established control level, or determining the absence or likely absence of IBS if the level of anti-vinculin and anti-CdtB antibody is equal or lower than the established control level. In various embodiments, the established control level is a level of anti-vinculin and anti-CdtB antibodies within two standard deviations of anti-vinculin and anti-CdtB antibody levels from subjects without IBS. In certain embodiments, the method further comprises analyzing the biological sample for a level of anti-vinculin and anti-CdtB antibodies.

In various embodiments, the method comprises: providing a biological sample from a subject desiring diagnosis of IBS, detecting in the biological sample, a level of anti-vinculin and anti-CdtB antibodies, and determining a presence or likely presence of IBS if the level of anti-CdtB antibodies is significantly higher than an established control level, or determining the absence or likely absence of IBS if the level of anti-vinculin and anti-CdtB antibodies is not significantly higher than the established control level. In various embodiments the established control level is a level of anti-vinculin and anti-CdtB antibodies from subjects without IBS. In certain embodiments, the method further comprises analyzing the biological sample for a level of anti-vinculin and anti-CdtB antibodies.

In various embodiments, the method comprises: providing a biological sample from a subject desiring diagnosis of IBS, detecting in the biological sample, a presence of anti-vinculin antibodies, and determining a presence or likely presence of IBS if the presence of anti-vinculin antibodies is detected, or determining an absence or likely absence of IBS if there is an absence of anti-vinculin antibodies. In certain embodiments, the method further comprises analyzing the biological sample for the presence or absence of anti-vinculin antibodies.

In various embodiments, the method comprises: providing a biological sample from a subject desiring diagnosis of IBS, detecting in the biological sample, a level of anti-vinculin antibodies, and determining a presence or likely presence of IBS if the level of an anti-vinculin antibody is higher than an established control level, or determining the absence or likely absence of IBS if the level of an anti-vinculin antibody is equal or lower than the established control level. In various embodiments, the established control level is a level of anti-vinculin antibodies within two standard deviations of anti-vinculin antibody levels from subjects without IBS. In certain embodiments, the method further comprises analyzing the biological sample for a level of anti-vinculin antibodies.

In various embodiments, the method comprises: providing a biological sample from a subject desiring diagnosis of IBS, detecting in the biological sample, a level of anti-vinculin antibodies, and determining a presence or likely presence of IBS if the level of anti-vinculin antibodies is significantly higher than an established control level, or determining the absence or likely absence of IBS if the level of anti-vinculin antibodies is not significantly higher than the established control level. In various embodiments the established control level is a level of anti-vinculin antibodies from subjects without IBS. In certain embodiments, the method further comprises analyzing the biological sample for a level of anti-vinculin antibodies.

In various embodiments, the method comprises: providing a biological sample from a subject desiring diagnosis of IBS, detecting in the biological sample, a presence of anti-CdtB antibodies, and determining a presence or likely presence of IBS if the presence of anti-CdtB antibodies are detected, or determining an absence or likely absence of IBS if there is an absence of anti-CdtB antibodies. In certain embodiments, the method further comprises analyzing the biological sample for the presence or absence of anti-CdtB antibodies.

In various embodiments, the method comprises: providing a biological sample from a subject desiring diagnosis of IBS, detecting in the biological sample, a level of anti-CdtB antibodies, and determining a presence or likely presence of IBS if the level of an anti-CdtB antibody is higher than an established control level, or determining the absence or likely absence of IBS if the level of an anti-CdtB antibody is equal or lower than the established control level. In various embodiments, the established control level is a level of anti-CdtB antibodies within two standard deviations of anti-CdtB antibody levels from subjects without IBS. In certain embodiments, the method further comprises analyzing the biological sample for a level of anti-CdtB antibodies.

In various embodiments, the method comprises: providing a biological sample from a subject desiring diagnosis of IBS, detecting in the biological sample, a level of anti-CdtB antibodies, and determining a presence or likely presence of IBS if the level of anti-CdtB antibodies is significantly higher than an established control level, or determining the absence or likely absence of IBS if the level of anti-CdtB antibodies is not significantly higher than the established control level. In various embodiments the established control level is a level of anti-CdtB antibodies from subjects without IBS. In certain embodiments, the method further comprises analyzing the biological sample for a level of anti-CdtB antibodies.

Not all subjects with the presence of anti-vinculin antibodies and/or anti-CdtB antibodies will have or develop IBS; however, these methods provide an indication on a likelihood of whether the subject has IBS or will develop IBS. A determination of a likely presence of IBS may be further correlated and/or confirmed by other diagnostic methods for IBS, or with symptoms of IBS known in the art. Further, a determination of a likely absence of IBS may also be further correlated and/or confirmed by other diagnostics methods for IBS or symptoms of IBS known in the art to rule out IBS.

In various embodiments, the IBS can be C-IBS, D-IBS, A-IBS (also known as M-IBS), or post-infectious irritable bowel syndrome (PI-IBS). In particular embodiments, the IBS is D-IBS.

In various embodiments, the system comprises: an isolated biological sample from a subject desiring diagnosis of IBS, and an assay for detecting in the biological sample, a presence or level of anti-vinculin and anti-CdtB antibodies.

In various embodiments, the system comprises: an isolated biological sample from a subject desiring diagnosis of IBS, and an assay for detecting in the biological sample, a presence or level of an anti-vinculin antibody.

In various embodiments, the system comprises: an isolated biological sample from a subject desiring diagnosis of IBS, and an assay for detecting in the biological sample, a presence or level of an anti-CdtB antibody.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample, a second reagent (e.g., secondary antibody) to react with the anti-vinculin antibody, and a substrate. In various embodiments, the first reagent is vinculin or a fragment thereof, which will react with the anti-vinculin antibody if present in the biological sample. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies is detected, or determining an absence or likely absence of IBS if the absence of anti-vinculin antibodies is detected. In various embodiments, the machine is a computer. In various embodiments, the computer comprises a display element for displaying whether there is a presence or absence of IBS.

In various embodiments, the system further comprises a machine for determining a presence or likely presence of IBS if the level of anti-vinculin antibodies is higher than an established control level, or determining an absence or likely absence of the IBS if the level of anti-vinculin antibodies is equal or lower than the established control level. In various embodiments, the established control level is a level of anti-vinculin antibodies within two standard deviations of anti-vinculin antibody levels from subjects without IBS. In certain embodiments, the method further comprises analyzing the biological sample for a level of anti-vinculin antibodies.

In various embodiments, the system further comprises a machine for determining a presence or likely presence of IBS if the level of anti-vinculin antibodies is significantly higher than an established control level, or determining an absence or likely absence of IBS if the level of anti-vinculin antibodies is not significantly higher than the established control level. In various embodiments the established control level is a level of anti-vinculin antibodies from subjects without IBS. In certain embodiments, the method further comprises analyzing the biological sample for a level of anti-vinculin antibodies.

In various embodiments, the assay comprises a first reagent to react with the biological sample, a second reagent (e.g., secondary antibody) to react with the anti-CdtB antibody, and a substrate. In various embodiments, the first reagent is CdtB or a fragment thereof, which will react with the anti-CdtB antibody if present in the biological sample. In various embodiments, the second reagent comprises a label to produce a signal to indicate the presence of the anti-CdtB antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-CdtB antibody. In various embodiments, the first reagent comprises a label to produce a signal to indicate the presence of the anti-CdtB antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-CdtB antibodies is detected, or determining an absence or likely absence of IBS if the absence of anti-CdtB antibodies is detected. In various embodiments, the machine is a computer. In various embodiments, the computer comprises a display element for displaying whether there is a presence or absence of IBS.

In various embodiments, the system further comprises a machine for determining a presence or likely presence of IBS if the level of anti-CdtB antibodies is higher than an established control level, or determining an absence or likely absence of the IBS if the level of anti-CdtB antibodies is equal or lower than the established control level. In various embodiments, the established control level is a level of anti-CdtB antibodies within two standard deviations of anti-CdtB antibody levels from subjects without IBS. In certain embodiments, the method further comprises analyzing the biological sample for a level of anti-CdtB antibodies.

In various embodiments, the system further comprises a machine for determining a presence or likely presence of IBS if the level of anti-CdtB antibodies is significantly higher than an established control level, or determining an absence or likely absence of IBS if the level of anti-CdtB antibodies is not significantly higher than the established control level. In various embodiments the established control level is a level of anti-CdtB antibodies from subjects without IBS. In certain embodiments, the method further comprises analyzing the biological sample for a level of anti-CdtB antibodies.

In various embodiments, the assay comprises assays (e.g., as described above) for the detection of the levels of anti-vinculin antibodies and anti-CdtB antibodies.

In various embodiments, the determining the presence or level of anti-vinculin antibodies and/or anti-CdtB antibodies comprises adding vinculin or a fragment thereof as discussed herein and/or CdtB or a fragment thereof as discussed herein to a biological sample from a subject desiring a determination regarding IBS, wherein anti-vinculin and/or anti-CdtB antibodies (if present in the biological sample) specifically binds to the vinculin or the fragment thereof and/or the CdtB or the fragment thereof in the biological sample; measuring the levels the anti-vinculin antibodies and the anti-CdtB antibodies in the biological sample; and identifying that the subject has IBS if the levels of the anti-vinculin antibodies is higher than the levels of the anti-CdtB antibodies.

In various embodiments, the assay comprises adding vinculin or a fragment thereof as discussed herein and/or CdtB or a fragment thereof as discussed herein to a biological sample from a subject desiring a determination regarding IBS, wherein anti-vinculin and/or anti-CdtB antibodies (if present in the biological sample) specifically binds to the vinculin or the fragment thereof and/or the CdtB or the fragment thereof in the biological sample; measuring the levels the anti-vinculin antibodies and the anti-CdtB antibodies in the biological sample; and identifying that the subject has IBS if the levels of the anti-vinculin antibodies is higher than the levels of the anti-CdtB antibodies.

Selecting Treatments and Treatments

Various embodiments provide for a method of selecting a therapy for IBS for a subject in need thereof.

In various embodiments, the method comprises: detecting the presence of anti-vinculin antibodies and anti-CdtB antibodies in a subject who desires a diagnosis to distinguish IBS from IBD, Celiac Disease or both; and selecting a therapy to treat IBS.

In various embodiments, the method comprises: detecting the presence of anti-vinculin antibodies in a subject who desires a diagnosis to distinguish IBS from IBD, Celiac Disease or both; and selecting a therapy to treat IBS.

In various embodiments, the method comprises: detecting the presence of anti-CdtB antibodies in a subject who desires a diagnosis to distinguish IBS from IBD, Celiac Disease or both; and selecting a therapy to treat IBS.

Selecting a therapy as used herein, includes but is not limited to selecting, choosing, prescribing, advising, recommending, instructing, or counseling the subject with respect to the treatment.

In various embodiments, the method further comprises administering the therapy to treat IBS. In various embodiments, the therapy is a therapy as described herein. In various embodiments, the available therapy comprises administering a course of antibiotic therapy to treat IBS. In various embodiments, the therapy is an available therapy in the prior art.

In various embodiments, the method comprises: detecting the presence of anti-vinculin antibodies and anti-CdtB antibodies; and selecting a course of antibiotic therapy to treat IBS. In various embodiments, the method further comprises administering the course of antibiotic therapy treat IBS.

In various embodiments, the method comprises: detecting the presence of anti-vinculin antibodies; and selecting a course of antibiotic therapy to treat IBS. In various embodiments, the method further comprises administering the course of antibiotic therapy treat IBS.

In various embodiments, the method comprises: detecting the presence of anti-CdtB antibodies; and selecting a course of antibiotic therapy to treat IBS. In various embodiments, the method further comprises administering the course of antibiotic therapy treat IBS.

In various embodiments, detecting the presence of anti-vinculin antibodies, anti-CdtB antibodies or both can be performed as described by the methods or systems of the present invention.

In various embodiments, the subject can be a subject presenting one or more symptoms of IBS; for example, as discussed herein.

Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paramomycin.

In various embodiments, the IBS treated can be C-IBS, D-IBS, A-IBS (also known as M-IBS), or post-infectious irritable bowel syndrome (PI-IBS). In particular embodiments, the IBS is D-IBS.

Various embodiments provide for treating IBS in a subject. The method comprises providing an IBS therapy and administering the IBS therapy to a subject diagnosed with IBS using the methods of the present invention. That is, the subject has been diagnosed with IBS via the detection of the presence of anti-vinculin and anti-CdtB antibodies in accordance with the methods of the present invention as discussed herein.

In various embodiments, the IBS therapy is a therapy as described herein. In various embodiments, the IBS therapy comprises administering a course of antibiotic therapy to treat IBS. In various embodiments, the IBS therapy is an available therapy in the prior art. In various embodiments, the IBS therapy is a course of antibiotic therapy as described herein.

In various embodiments, the IBS treated can be C-IBS, D-IBS, A-IBS (also known as M-IBS), or post-infectious irritable bowel syndrome (PI-IBS). In particular embodiments, the IBS is D-IBS.

Optical Density as a Measurement of Antibody Levels

In certain embodiments, optical density (OD) is used to measure the level of anti-vinculin antibodies and/or anti-CDT antibodies. For example, the optical density serves as the established control level in various embodiments. In certain embodiments, when the OD of anti-vinculin antibodies ($OD_V$) is greater than 1.62, 1.86 or 2.23 the subject is determined to have IBS. In various embodiments, when the OD of anti-vinculin antibodies ($OD_V$) is greater than 1.00, 1.25, 1.50, 1.75, 2.00, 2.25, 2.50 2.75 the subject is determined to have IBS. In certain embodiments, these OD numbers are based on a dilution of the biological sample of 1:32 and antigen concentration of 1.2 ug/ml.

In certain embodiments, when the OD of anti-CDT antibodies ($OD_{CDT}$) is greater than 2.48 or 2.79, the subject is determined to have IBS. In various embodiments, when the OD of anti-CDT antibodies ($OD_{CDT}$) is greater than 2.00, 2.25, 2.50, 2.75, 3.00, the subject is determined to have IBS. In certain embodiments, these OD numbers are based on a dilution of the biological sample of 1:512 and antigen concentration of 1.2 ug/ml.

In other embodiments, the $OD_V$ and the $OD_{CDT}$ cutoff points can be determined based on different dilutions of the biological sample and the antigens and are included within the embodiments of the present invention.

In further embodiments, the above determinations may be used to direct the treatment for the subject. In one embodiment, a subject with the likely presence of IBS or a likelihood of having IBS may be treated with one or more therapies for IBS.

One of ordinary skill in the art will be able to select an available treatment for IBS based on the diagnosis of IBS.

For example, antibiotics such as rifaximin and neomycin can be used to treat IBS. Particularly, rifaximin can be used to treat diarrhea-predominant IBS, and a rifaximin/neomycin combination can be used to treat constipation-predominant IBS.

Anti-Vinculin Antibodies

In various embodiments, the anti-vinculin antibody detected in these methods or systems is an antibody that binds specifically to vinculin.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to SEQ ID NO:7.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of SEQ ID NO:7.

Contiguous residues of vinculin or SEQ ID NO:7 include those beginning at any amino acid and ending at any amino acid of vinculin or SEQ ID NO:7.

Protein sequence of Vinculin (SEQ ID NO:7):

MPVFHTRTIESILEPVAQQISHLVIMHEEGEVDGKAIPDLTAPVAAVQAA

VSNLVRVGKETVQTTEDQILKRDMPPAFIKVENACTKLVQAAQMLQSDPY

SVPARDYLIDGSRGILSGTSDLLLTFDEAEVRKIIRVCKGILEYLTVAEV

VETMEDLVTYTKNLGPGMTKMAKMIDERQQELTHQEHRVMLVNSMNTVKE

LLPVLISAMKIFVTTKNSKNQGIEEALKNRNFTVEKMSAEINEIIRVLQL

TSWDEDAWASKDTEAMKRALASIDSKLNQAKGWLRDPSASPGDAGEQAIR

QILDEAGKVGELCAGKERREILGTCKMLGQMTDQVADLRARGQGSSPVAM

QKAQQVSQGLDVLTAKVENAARKLEAMTNSKQSIAKKIDAAQNWLADPNG

GPEGEEQIRGALAEARKIAELCDDPKERDDILRSLGEISALTSKLADLRR

QGKGDSPEARALAKQVATALQNLQTKTNRAVANSRPAKAAVHLEGKIEQA

QRWIDNPTVDDRGVGQAAIRGLVAEGHRLANVMMGPYRQDLLAKCDRVDQ

-continued

LTAQLADLAARGEGESPQARALASQLQDSLKDLKARMQEAMTQEVSDVFS

DTTTPIKLLAVAATAPPDAPNREEVFDERAANFENHSGKLGATAEKAAAV

GTANKSTVEGIQASVKTARELTPQVVSAARILLRNPGNQAAYEHFETMKN

QWIDNVEKMTGLVDEAIDTKSLLDASEEAIKKDLDKCKVAMANIQPQMLV

AGATSIARRANRILLVAKREVENSEDPKFREAVKAASDELSKTISPMVMD

AKAVAGNISDPGLQKSFLDSGYRILGAVAKVREAFQPQEPDFPPPPPDLE

QLRLTDELAPPKPPLPEGEVPPPRPPPPEEKDEEFPEQKAGEVINQPMMM

AARQLHDEARKWSSKGNDIIAAAKRMALLMAEMSRLVRGGSGTKRALIQC

AKDIAKASDEVTRLAKEVAKQCTDKRIRTNLLQVCERIPTISTQLKILST

VKATMLGRTNISDEESEQATEMLVHNAQNLMQSVKETVREAEAASIKIRT

DAGFTLRWVRKTPWYQ

In various embodiments, detecting the presence or absence of the antibody is performed on a biological sample obtained from the subject. In another embodiment, detecting the presence or absence of the antibody is performed on a blood, serum, or stool sample obtained from the subject. One of ordinary skill in the art will readily appreciate methods and systems that can be used to detect the presence or absence of an antibody that binds specifically to vinculin, SEQ ID NO: 7 or a fragment thereof. These methods and systems include but are not limited to ELISA, immunohistochemistry, flow cytometry, fluorescence in situ hybridization (FISH), radioimmuno assays, and affinity purification.

In various embodiments, vinculin, SEQ ID NO: 7 or a fragment thereof (as described above) is used as a substrate or reagent (e.g., collector, trap) to bind anti-vinculin antibodies (if present).

In certain embodiments, detecting the presence or absence of an antibody that binds specifically to vinculin, SEQ ID NO: 7 or a fragment thereof may be performed by contacting vinculin, SEQ ID NO: 7 or a fragment thereof to a biological sample obtained from the subject to isolate the antibody that binds specifically to vinculin, SEQ ID NO: 7 or a fragment thereof, wherein the isolation of the antibody that binds specifically to vinculin, SEQ ID NO: 7 or a fragment thereof indicates the presence of the antibody and the lack of isolation of the antibody that binds specifically to vinculin, SEQ ID NO: 7 or a fragment thereof indicates the lack of the antibody. In various embodiments, the fragment of vinculin or SEQ ID NO: 7 may be the fragments as described herein. As an example, an affinity matrix comprising vinculin, SEQ ID NO: 7 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO: 7 or a fragment thereof; the labeled vinculin, SEQ ID NO: 7 or a fragment thereof can be contacted with a biological sample to allow the antibody (if present) to bind specifically to the labeled vinculin, SEQ ID NO: 7 or a fragment thereof. In various embodiments, the labeled vinculin, SEQ ID NO: 7 or a fragment thereof can be separated out and analyzed for its binding to the antibody.

Anti-CdtB Antibodies

In various embodiments, the anti-CdtB antibody is an antibody that binds specifically to CdtB subunit of CDT. An example of a CdtB amino acid sequence is *Campylobacter jejuni* cytolethal distending toxin B, which has the amino acid sequence (SEQ ID NO: 5). Another example of a CdtB amino acid sequence is *Campylobacter coli* cytolethal distending toxin B, which has the amino acid sequence (SEQ ID NO:1) and nucleic acid sequence (SEQ ID NO:2).

```
SEQ ID NO: 5:
MKKIICLFLSFNLAFANLENFNVGTWNLQGSSAATESKWSVSVRQLVSGANPLDILMIQEAGTLP

RTATPTGRHVQQGGTPIDEYEWNLGTLSRPDRVFIYYSRVDVGANRVNLAIVSRMQAEEVIVLPP

PTTVSRPIIGIRNGNDAFFNIHALANGGTDVGAIITAVDAHFANMPQVNWMIAGDFNRDPSTITST

VDRELANRIRVVFPTSATQASGGTLDYAITGNSNRQQTYTPPLLAAILMLASLRSHIVSDHFPVNF

RKF

SEQ ID NO: 1:
MKKIVFLILSFNVLFAALENYNTGTWNLQGSSAATESKWNVSIRQLITGANPMDVLAVQEAGVL

PSTAMMTPRQVQPVGVGIPIHEYIWNLGSVSRPSSVYIYYSRVDVGANRVNLAIVSRVQADEVFV

LPPPTVASRPIIGIRIGNDAFFNIHALASGGNDAGAIVAAVDMFFRNRPDINWMILGDFNRESGAL

VTLLDPDLRARTRVVVPPSSTQTSGRTIDYAITGNSNTAALYNPPPIVAILALEGLRTFLASDHFPV

NFRRP

SEQ ID NO: 2:
atgaaaaaaa tagtattttt gattttaagt tttaatgtat tatttgccgc tttagaaaat      60
tacaacaccg gaacttggaa tttgcaaggc tcatcagctg caactgaaag caaatggaat     120
gttagtataa gacaactcat aaccggtgca aatcctatgg atgttttagc tgttcaagaa     180 gcggggggttt tacctagtac agctatgatg actcctagac aggtacaacc cgtgggcgtg     240
ggtattccta tacatgaata catatggaat ttaggctctg tatcaagacc tagctctgtt     300
```

-continued

```
tatatatatt attctagagt ggatgtagga gcaaatcgtg tgaatttagc tatcgttagc    360
agagtgcaag cggatgaagt ttttgtttta cccctccaa cagttgcttc aagacctatt    420
ataggcatac gcataggcaa tgatgctttt ttcaatatac acgctctagc aagtggggga    480
aatgacgcag gagccattgt cgctgctgtg gatatgtttt ttagaaatag acctgatatt    540
aattggatga ttttaggcga ttttaataga gaatcaggcg ccttagtaac cttgctagat    600
cctgacttaa gagcacgcac tcgcgtagtt gttccgcctt cttctacgca aacaagtgga    660
agaacgattg attatgctat cactggaaat tccaacactg cagctttata caacccacca    720
ccgatagttg cgattttagc tttagaagga ttaagaacct ttttggcttc agatcatttt    780
cctgtaaatt ttagaagacc ttag                                          804
```

Accordingly, in various embodiments, the antibody binds specifically to SEQ ID NO:5 (CdtB of *C. jejuni*). In various embodiments, the anti-CdtB antibody is an antibody that binds specifically to an amino acid sequence at least 80%, 85%, 90%, 95%, 96%, 97%, 98%, or 99% identical to SEQ ID NO: 5.

In another embodiment, the anti-CdtB antibody is an antibody that binds specifically to SEQ ID NO:1 (CdtB of *C. coli*). In various embodiments, the anti-CdtB antibody is an antibody that binds specifically to an amino acid sequence at least 80%, 85%, 90%, 95%, 96%, 97%, 98%, or 99% identical to SEQ ID NO:1.

In another embodiment, the anti-CdtB antibody is an antibody that binds specifically to a 17 residue peptide of CdtB (e.g., 17 residues of SEQ. ID NOs: 1 or 5). In one embodiment, the 17 residue peptide has the following sequence: LDYAITGNSNRQQTYTP (SEQ ID NO:3).

In other embodiments, the anti-CdtB antibody is an antibody that binds specifically to a 17 residue peptide that has at least 80%, 85%, 90%, 95%, 96%, 97%, 98%, 99% or 100% homology with 17 contiguous residues of CdtB (e.g., 17 contiguous residues of SEQ. ID NOs: 1 or 5). In one embodiment, the 17 residues of CdtB have the following sequence: LDYAITGNSNRQQTYTP (SEQ ID NO:3).

In other embodiments, the anti-CdtB antibody is an antibody that binds specifically to a polypeptide comprising 17 residues that have at least 80%, 85%, 90%, 95%, 96%, 97%, 98%, 99% or 100% homology with 17 contiguous residues of CdtB (e.g., 17 residues of SEQ. ID NOs: 1 or 5). In one embodiment, the 17 contiguous residues of CdtB have the following sequence: LDYAITGNSNRQQTYTP (SEQ ID NO:3).

In another embodiment, the anti-CdtB antibody is an antibody that antibody binds specifically to an 18 residue peptide having the following sequence: CLDYAITGNSNRQQTYTP (SEQ ID NO:4). The cysteine at the N-terminus was added to SEQ ID NO:3 for purposes of conjugation.

In other embodiments, the anti-CdtB antibody is an antibody that binds specifically to a polypeptide comprising 18 residues that have at least 80%, 85%, 90%, 95%, 96%, 97%, 98%, 99% or 100% homology to CLDYAITGNSNRQQTYTP (SEQ ID NO:4).

In another embodiment, the anti-CdtB antibody is an antibody that binds specifically to a 5, 6, 7, 8, 9, 10, 11, 12, 13, 14, 15, 16, 17, 18, 19, 20, 21, or 22 residue peptide that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). In another embodiment, the anti-CdtB antibody is an antibody that binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). Contiguous residues of SEQ ID NO:1 include those beginning at any amino acid and ending at any amino acid of SEQ ID NO:1. Contiguous residues of SEQ ID NO:5 include those beginning at any amino acid and ending at any amino acid of SEQ ID NO:5.

In another embodiment, the anti-CdtB antibody is an antibody that antibody binds specifically to a 5, 6, 7, 8, 9, 10, 11, 12, 13, 14, 15, 16, or 17 residue peptide that has at least 80%, 85%, 90%, 95%, 96%, 97%, 98%, 99% or 100% homology with 5, 6, 7, 8, 9, 10, 11, 12, 13, 14, 15, 16, or 17 contiguous residues of LDYAITGNSNRQQTYTP (SEQ ID NO:3) (e.g., 5, 6, 7, 8, 9, 10, 11, 12, 13, 14, 15, 16, or 17 contiguous residues of SEQ ID NO:3). In another embodiment, the purified antibody binds specifically to a polypeptide comprising 5, 6, 7, 8, 9, 10, 11, 12, 13, 14, 15, 16, or 17 residues that has at least 80%, 85%, 90%, 95%, 96%, 97%, 98%, 99% or 100% homology with 5, 6, 7, 8, 9, 10, 11, 12, 13, 14, 15, 16, or 17 contiguous residues of SEQ ID NO:3 (e.g., 5, 6, 7, 8, 9, 10, 11, 12, 13, 14, 15, 16, or 17 contiguous residues of SEQ ID NO:3). Contiguous residues of SEQ ID NO: 3 include those beginning at any amino acid and ending at any amino acid of SEQ ID NO: 3.

In another embodiment, the anti-CdtB antibody is an antibody that binds specifically to a 17 residue peptide encoded by the CdtB gene sequence. In particular embodiments, the anti-CdtB antibody is an antibody that binds specifically to a 17 residue peptide encoded by SEQ ID NO: 2. In various embodiments, the anti-CdtB antibody is an antibody that binds specifically to a 14, 15, 16, 17, 18, 19, 20, 21, or 22 residue peptide encoded by SEQ ID NO: 2. In various embodiments, the purified antibody binds specifically to a 14, 15, 16, 17, 18, 19, 20, 21, or 22 residue peptide that has at least 80%, 85%, 90%, 95%, 96%, 97%, 98%, 99% or 100% homology to 14, 15, 16, 17, 18, 19, 20, 21, or 22 contiguous residues encoded by SEQ ID NO: 2. In various embodiments, the anti-CdtB antibody is an antibody that binds specifically to a polypeptide comprising 14, 15, 16, 17, 18, 19, 20, 21, or 22 residues that have at least 80%, 85%, 90%, 95%, 96%, 97%, 98%, 99% or 100% homology to 14, 15, 16, 17, 18, 19, 20, 21, or 22 contiguous residues encoded by SEQ ID NO:2.

In another embodiment, the anti-CdtB antibody is an antibody that binds specifically to a peptide encoded by the nucleic acid sequence having the following sequence: CTT-GATTATGCAATTACAGGAAATTCAAATA-GACAACAAACCTATACTCCA (SEQ ID NO:6), which encodes the 17 amino acid peptide of SEQ ID NO:3. In another embodiment, the anti-CdtB antibody is an antibody that binds specifically to a polypeptide comprising a peptide encoded by SEQ ID NO:6.

In another embodiment, the anti-CdtB antibody is an antibody that binds specifically to CdtB purified from *E. coli* overexpressing a near full-length CdtB ORF. (See Infection and Immunity, December 2000, p. 6535-6541, Vol. 68, No. 12, herein incorporated by reference in its entirety as though fully set forth.)

In various embodiments, when determining the presence or level of anti-vinculin antibodies, vinculin protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration. In various embodiments, an about 1:32 dilution of the biological sample (e.g., plasma) is used in the determination of the presence or level of anti-vinculin antibodies. In other embodiments, an about 1:8, 1:10, 1:12; 1:16, 1:20, 1:24, 1:30, 1:36, 1:48, or 1:64 dilution of the biological sample (e.g., plasma) is used in the determination of the presence or level of anti-vinculin antibodies. In other embodiments, an about 1:8 to 1:64 dilution of the biological sample (e.g., plasma) is used in the determination of the presence or level of anti-vinculin antibodies.

In various embodiments, when determining the presence or level of anti-CdtB antibodies, CdtB protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration. In various embodiments, a 1:512 dilution of the biological sample (e.g., plasma) is used in the determination of the presence or level of anti-CdtB antibodies. In other embodiments, an about 1:128, 1:256, 1:768, or 1:1024 dilution of the biological sample (e.g., plasma) is used in the determination of the presence or level of anti-CdtB antibodies. In other embodiments, an about 1:100, 1:150, 1:200, 1:250, 1:300, 1:350, 1:400, 1:500, 1:550; 1:600, 1:650, 1:700, 1:750, 1:800, 1:850, 1:900, 1:950, or 1:1000 dilution of the biological sample (e.g., plasma) is used in the determination of the presence or level of anti-CdtB antibodies. In other embodiments, an about 1:100-1:1000 dilution of the biological sample (e.g., plasma) is used in the determination of the presence or level of anti-CdtB antibodies.

Antigens are immobilized for about 8, 9, 10, 11, 12, 13, 14, 15, 16, 17, 18, 19 or 20 hours (e.g., overnight, >16 hours) at about 4° C. onto high-binding plates (e.g., 96-well plates) in Borate Buffered Saline (BBS) at a pH of 8.2. Wells are alternately coated with antigen or left uncoated in BBS to allow determination of non-specific binding of plasma. Wells are blocked with about 3% bovine serum albumin in 1×PBS for about 1 hour at about room temperature. Coated and uncoated wells are then incubated with a 1:512 dilution of plasma for CdtB and a 1:32 dilution of plasma for vinculin for about 1 hour at room temperature. Antibodies to CdtB and vinculin are used as positive controls. This was followed by about 1 hour incubation with HRP conjugated secondary antibodies. Each step is followed by a series of washes using 0.05% PBS-Tween 20. Finally, a 3,3',5,5'-Tetramethylbenzidine (TMB) substrate solution is used for visualization and immediately read on a plate reader (e.g., BioTek Synergy HT; Winooski, Vt.). The optical densities (OD) are read for about 90 minutes at 370 nm and used to compare levels of anti-CdtB or anti-vinculin. Raw OD values were used for the data analysis.

Types of IBS

In various embodiments, the IBS detected by the methods, assays or systems is constipation predominant IBS (C-IBS), diarrhea predominant IBS (D-IBS), alternating IBS (A-IBS) (more recently re-named as mixed (M-IBS)), or post-infectious irritable bowel syndrome (PI-IBS). In various embodiments, the IBS is D-IBS.

In certain embodiments, the subject desiring diagnosis of IBS in accordance to the methods, assays, and systems of the present invention may have one or more symptoms indicative of IBS. Examples of IBS symptoms include but are not limited to diarrhea, constipation, bloating, and abdominal pain.

Biological Samples

Examples of biological samples include but are not limited to body fluids, whole blood, plasma, stool, intestinal fluids or aspirate, and stomach fluids or aspirate, serum, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method, the biological sample may be whole blood, blood plasma, blood serum, stool, intestinal fluid or aspirate or stomach fluid or aspirate. In various embodiments, the biological sample may be whole blood. In various embodiments, the biological sample may be serum. In various embodiments, the biological sample may be plasma.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Adult male Sprague-Dawley rats were gavaged with either *Campylobacter jejuni* 81-176 (C+) or a CDT-knockout (CDT−) strain of *Campylobacter*. The CDT− strain was a *Campylobacter jejuni* 81-176 strain that failed to express cytolethal distending toxin (CdtB) due to an insertion mutation at the gene for CdtB. After gavage, rats were followed with daily stool culture for *Campylobacter* until 2 consecutive negative cultures were seen. Once cleared of colonization, rats were housed in identical conditions for 3 months (post-infectious). At the end of 3 months, fresh stool was collected by anal stimulation and used to evaluate both the appearance (on a modified Bristol score) and stool weight before and after being placed in an oven overnight. The percentage dry stool weights were calculated. Both groups were compared for stool dry weight, variability in dry weight by day and stool consistency and variability.

Both groups of rats (C+ and CDT−) demonstrated equal colonization of the rat as evidenced by positive and prolonged detection in stool after gavage. Three months after loss of *Campylobacter*, the average stool dry weights for all three days were similar between groups (Table 1). However, the variability in stool form and weight was significantly different between groups. The rats exposed to wild type Campylobacter had a substantial variability in stool weight and also had altered stool consistency. The rats exposed to CDT− Campylobacter had stool form and variability identical to that of healthy control rats.

TABLE 1

Comparison of stool percentage dry weights and consistency

|  | Control | C+ | CDT− |
|---|---|---|---|
| Average % of stool dry weight | 63.7 ± 3.2 | 60.1 ± 6.8 | 61.0 ± 6.3 |
| Daily variability of Dry Weight | 4.9 ± 3.8 | 8.4 ± 6.4 | 4.9 ± 5.5* |
| Average Stool Consistency (Based on Bristol Stool Scale) | 1.0 | 1.5 ± 0.4 | 1.2 ± 0.3** |
| Daily Variability of Stool Consistency | N/A | 0.51 ± 0.38 | 0.30 ± 0.34*** |

*P value = 0.004 when compared to C+
**P value = 0.000025 when compared to C+
***P value = 0.006 when compared to C+

Male Sprague-Dawley rats were gavaged with $10^8$ cfu of either wildtype or cdtB mutant *C. jejuni* 81-176. Rats were evaluated at 2 and 4 days post-infection, and at 3 months after infection had cleared (including rats with or without long term sequelae of chronic altered bowel function in the post-infectious period). Control rats were gavaged with vehicle alone. At time of euthanasia, laparotomy was performed and ileal tissue (5 cm proximal to ileocecal valve) was stained with two different antibodies against CdtB: One was raised against CdtB purified from *E. coli* overexpressing a near full-length cdtB ORF; the second antibody was derived from rabbits inoculated with an 18 residue peptide (CLDYAITGNSNRQQTYTP (SEQ ID NO:4)), which consist of a cysteine added on the N-terminus of SEQ ID NO:3 for conjugation. Pre-immune rabbit serum was used as a control.

During acute infection, CdtB staining was prominent at the epithelial surface of the mucosa. Interestingly, both types of anti-CdtB specific antibodies stained intestinal neural elements, including ICC and myenteric ganglia. This widespread staining of neural elements was seen not only in rats exposed to wildtype *C. jejuni*, but also in rats exposed to cdtB mutants and rats never exposed to *C. jejuni*. Exposure to rabbit pre-immune sera produced no obvious staining of any rat ileal tissue.

Plasmids and Construction of Insertion-Deletion Mutants

The *Campylobacter* aphA-3 cassette (Labigne-Roussel et al., 1988. Gene disruption and replacement as a feasible approach for mutagenesis of *Campylobacter jejuni*. J. Bacteriol. 170:1704-1708), which confers kanamycin resistance, was amplified by PCR from plasmid pRY107. The CdtB ORF sequence was cleaved in the middle by a restriction enzyme and the aphA-3 cassette (Yao et al., 1993. Construction of new *Campylobacter* cloning vectors and a new mutational cat cassette. Gene 130:127-130) was cloned into that site to disrupt the cdtB sequence and prevent the expression of a functional CdtB. This plasmid was then electroporated into strain 81-176. Double crossover homologous recombinants, which were kanamycin resistant, were identified and underwent further PCR analysis to verify disruption of the CdtB ORF.

Example 2

Methods

Healthy control subjects, IBS subjects and subjects with inflammatory bowel disease (IBD) were recruited and serum was collected. The ELISA was prepared by coating 96 well plates with recombinant cdtB and human vinculin. After coating, a calibration curve was made for cdtB and vinculin using purified commercial anti-cdtB and anti-human-vinculin. Serum from healthy controls, IBS and IBD subjects was added to the wells and examined. The wells were incubated for 60 minutes prior to washing and application of secondary antibodies.

Anti-CdtB Antibodies

To determine the role of CdtB in the development of IBS, two antibodies were developed to CdtB from *C. jejuni* 81-176. The first was through immunization of rabbits with an 18 amino acid residue identified as highly antigenic (haAB) through protein modeling (AnaSpec, San Jose, Calif.). The second was developed through immunization of rabbits with the near full length CdtB peptide (wAb). To confirm the selectivity of rabbit serum to CdtB, lysates of *C. jejuni* 81-176, were run on western gel with and without blocking with CdtB protein to verify a 28 kDa band. With this validation, the wAb was used through the remaining experiments.

Acute *C. jejuni* Exposure and CdtB in Rats Acutely Infected with *C. jejuni*

To determine the role of CdtB in our animal model, we examined ileal tissue in rats acutely infected with *C. jejuni*. Rats were gavaged with $10^8$ cfu/mL of *C. jejuni* 81-176. On day 2, rats were euthanized and sections of ileum were resected, fixed in 10% formalin (VWR, Radnor, Pa.), and sections prepared for immunohistochemistry. As a comparison, ileum from rats naïve to *C. jejuni* were similarly prepared. To these sections wAb and preimmune rabbit serum (negative control) were applied to contiguous sections.

Anti-CdtB Antibody Tracking in Human Ileum

Based on finding activity of wAb to mucosa and neural elements of both *C. jejuni* infected and control rats, the study was repeated using human ileum sections. Humans who underwent ileocecectomy for colon malignancy were identified and a portion of the ileum was mounted and sections were incubated with wAb and preimmune serum using immunohistochemistry to determine if there was support for molecular mimicry.

Identification of Enteric Neuronal Protein Responsible for Molecular Mimicry

Since the enteric nervous system and in particular ganglia and enteric neuron was a site of localization for antibodies to CdtB (wAb), enteric neuronal stem cell lysates were obtained. Lysates were run on western gel with and without blocking with CdtB protein using wAb and haAB to identify a potential protein to which wAb was adhering. This was identified at 117 kDa and subsequently immunoprecipitation using wAb applied to beads was used to draw down the protein of interest. This was done by binding—proteins to beads then binding from lysates of $2.5 \times 10^8$ enteric neuronal stem cells through. Effluent was run on a gel and the band again identifying a protein at 117 kDa. This band was cut and mass spectroscopy was used to analyze the protein content.

After the identification of the protein of interest, confocal microscopy was used to determine the co-localization of antibodies to this protein in the tissue in comparison to tissue affinity with CdtB wAb in both rats and humans.

Detection of Antibodies to CdtB and Vinculin in Rats Exposed to *C. jejuni*

In our validated animal model of post-infectious IBS, male Sprague-Dawley rats exposed to *C. jejuni* 81-176 develop small intestinal bacterial overgrowth based on total bacterial counts by qPCR. This phenotype is augmented by repeated exposure to *C. jejuni*. In this experiment, 3 groups of rats are compared. The first group includes control rats that have never been exposed to *C. jejuni* (n=20). In the second group of rats, the animals were gavaged with vehicle as juveniles and 2 months later received a gavage of $10^8$ cfu/mL of *C. jejuni* 81-176 as adults (J−/A+) (n=50). The third group of animals were gavaged with $10^8$ cfu/mL of *C. jejuni* 81-176 as juveniles and re-expose by gavage with $10^8$ cfu/mL of *C. jejuni* 81-176 two months later as adults (J+/A+) (n=50). After the adult exposure, *C. jejuni* clearance from stool culture was achieved by 30 days. Rats were then euthanized 90 days after clearance of *C. jejuni* to guarantee they were truly post-infectious as previously reported. During dissection, sections of duodenum, jejunum and ileum were formalin fixed and resected for histology and luminal bacterial quantitation was done by qPCR as previous reported. At time of euthanasia, intra-cardiac puncture was used to collect blood and serum was separated and stored.

ELISA Methodology

Antigens (whole CdtB or vinculin (Novo, Short Hills, N.J.)) were bound to 96 well plates under humidified conditions overnight at 4° C. using 100 µl/well 0.125 µg/ml protein in BBS (Pierce). Wells were washed with 0.05% PBS-T and blocked with 120 µl/well of 0.5% BSA/PBS for 1 hour at room temperature in the humidified box. Samples (rat serum, human serum) as well as controls: wAB, vinculin Ab (Santa Cruz, Santa Cruz, Calif.) were added at a 1:100 dilution in 0.5% BSA/PBS for 2 hrs at room temperature in humidified box. Secondary antibody, human, rat or goat IgG conjugated with HRP (Jackson ImmunoResearch, West Grove, Pa.) was added 100 µl/well, 1:1000 dilution in 0.5% BSA/PBS for 30 min at room temperature in humidified box. The plates were washed with 0.05% PBS-T before adding 100 µl/well of substrate solution (Jackson ImmunoResearch, West Grove, Pa.) and read in plate reader after application of rat or human serum as indicated below (BioTek Synergy HT)

ELISA in Rats with and without *Campylobacter* Infection and Overgrowth

Serum from each of the 3 groups of rats was assayed: uninfected, single *campylobacter* exposure as adult, and immature and adult double infected. The resulting OD was compared between the 3 groups as well as rats segregated with and without small intestinal bacterial overgrowth (defined as >2 SD above the mean) as previously published. Finally, a correlation curve was created comparing the level of serum antibody to the degree of bacteria in the ileum.

ELISA in Humans with IBS

Three groups of humans were used to evaluate the titer of anti-CdtB and anti-vinculin antibodies. The first group was a group of healthy controls. Healthy control subjects were defined as subjects, who on questionnaire, reported no altered bowel function, no bloating and no abdominal pain (each less than 10 mm on a 100 mm VAS scale for the specific symptom). The second group was a group of diarrhea predominant IBS subjects based on Rome III criteria. The third group was composed of 10 subjects with Crohn's disease and 10 subjects with ulcerative colitis. ELISA was set up similar to the rat study. Titers of anti-CdtB and anti-vinculin were compared between the 3 groups. In addition, correlation was conducted between anti-CdtB and anti-vinculin. Finally, two unrelated proteins, c-kit and latrophillin were used in ELISA to determine control for non-specific binding in humans with IBS.

Immunofluorescence, Confocal Imaging of Anti-cdtB Antibody, Neural Markers and Vinculin Since there was evidence of neuronal binding by wAb, particularly the perigangliar regions and the deep muscular plexus interstitial cells of Cajal (DMP-ICC) in immunohistochemistry, colocalization experiments were undertaken comparing localization of wAb to anti-c-kit (R&D Systems, Minneapolis, Minn.), S-100 (neuronal) (Pierce Biotechnology, Rockford, Ill.) and PGP 9.5 (ganglia) (Pierce Biotechnology, Rockford, Ill.) and anti-vinculin (Santa Cruz, Santa Cruz, Calif.) all raised in goat. Confocal microscopic images were taken of contiguous sections of ileum from rats and humans for comparison.

Briefly, slides of acutely *C. Jejuni* infected and uninfected rat ileum and were deparaffinized and washed in sequentially in xylenes and ethanol before antigen retrieval and serum blocking. Primary antibodies were added (1:200 wAb raised in rabbit plus 1:100 c-kit, S100, PGP 9.5, or vinculin antibodies raised in goat) and incubated at room temperature in humidified conditions. Slides treated with primary antibody were washed in PBS and incubated with 1:30 DAPI (Invitrogen, Grand Island, N.Y.) and secondary antibodies: Alexa red 568 anti-goat (Invitrogen, Grand Island, N.Y.) for c-kit, S100, PGP 9.5 or vinculin antibodies (1:300) and Alexa green 488 anti-rabbit (Invitrogen, Grand Island, N.Y.) for wAB (1:300). After incubation in dark, humidified conditions, Prolong Gold (Invitrogen, Grand Island, N.Y.) was added and section covered with glass for viewing under Confocal Microscopy (Leica TCS SP5x microscope, Leica SCN400 F digital slide scanner.)

Gene Expression of Vinculin in Rats with and without SIBO

Rat ileal tissue RNA was extracted (Qiagen) from 3 months post *C. jejuni* infected and control uninfected animals and converted to cDNA by iScript reverse transcription (Bio Rad, Hercules, Calif.). Quantitative PCR was performed with primers specific to rat vinculin and normalized to gene expression of beta actin.

| Primers | | |
|---|---|---|
| beta actin[1] | FW: GGAGATTACTGCCCTGGCTCCTA (SEQ ID NO: 8) REV: GACTCATCGTACTCCTGCTTGCTG (SEQ ID NO: 9) | Amp: 150 bp |
| Vinculin[2] | FW: GCCAAGCAGTGCACAGATAA (SEQ ID NO: 10) REV: TCTTTCTAACCCAGCGCAGT (SEQ ID NO: 11) | Amp: 273 bp |

[1]Reference: Qian-Qian Liang et al., (2010) Herb Formula "Fufangqishe-Pill" Prevents Upright Posture-Induced Intervertebral Disc Degeneration at the Lumbar in Rats. J Pharmacol Sci 113: 23 - 31)
[2]Reference: Zhang et al., Proteome Science 2010 8: 12 (doi: 10,1186/1477-5956-8-12)

Statistical Analysis

The comparison of anti-CdtB and anti-vinculin levels between groups was compared by the non-parametric Mann-Whitney U test. Correlation curves between bacteria counts and antibody titers were compared by Pearson correlation. Pearson correlation was also used to compared anti-CdtB and anti-vinculin in humans. In the determination of a positive and negative ELISA a Chi-square was performed. For the comparison of ELISA to the colony counts of small bowel flora, a Pearson rank correlation was used. Finally, thresholds for anti-CdtB (>2.0 OD) and anti-vinculin (>1.2

OD) as a method of diagnosing IBS compared to controls and subjects with inflammatory bowel disease. Test characteristics such as sensitivity and specificity were determined based on these thresholds. Differences between groups was determined to be significant if P<0.05 and data are expressed as mean±SD.

Results 19 healthy controls, 20 IBD subjects and 42 IBS subjects participated in the study. Demographics were similar between groups. For the detection of anti-cdtB, an Optical density of ≥2.0 was set as positive and for the detection of anti-human vinculin antibodies an OD was set at ≥1.2. Based on these cutoffs, using either anti-vinculin or anti-cdtB was successful in diagnosing IBS over IBD or health controls (Table 2a). Since anti-cdtB is anti-vinculin, it would be expected that titers of serum anti-cdtB in all subjects would correspond to anti-human vinculin and this was found to be true (R=0.58, P<0.001).

TABLE 2a

|  | IBS vs all others | | IBS vs Health | | IBS vs IBD | |
| --- | --- | --- | --- | --- | --- | --- |
|  | Sensitivity | Specificity | Sensitivity | Specificity | Sensitivity | Specificity |
| Anti-vinculin | 58.6 | 94.1 | 58.6 | 87.5 | 58.6 | 100 |

Validation of Anti-CdtB Antibodies

Figure 5:
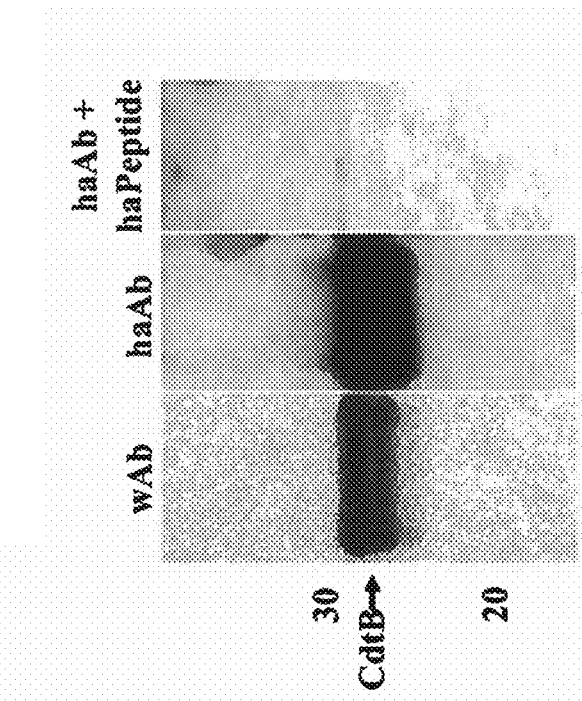
FIG. 5 depicts Western blot of protein vs. antibody in accordance with various embodiments of the present invention.
Figure 7:
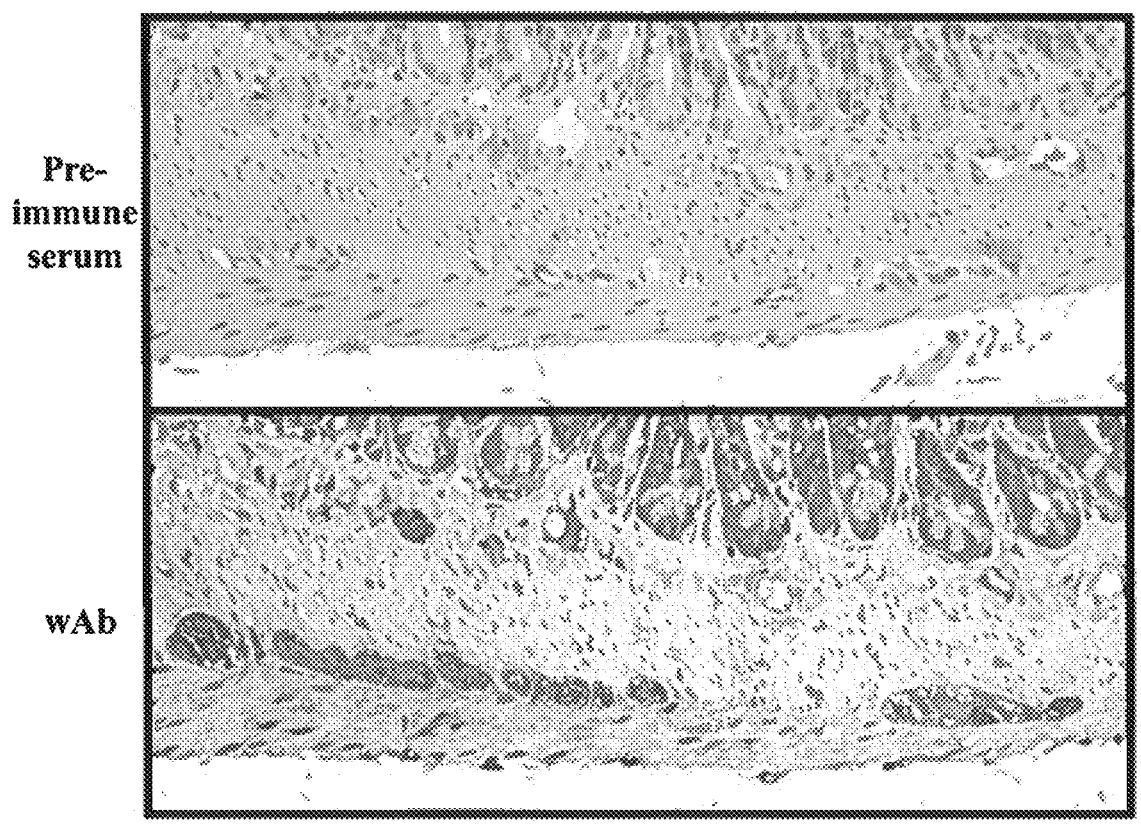
FIG. 7 depicts immunohistochemistry of samples from acute rats, day 2 in accordance with various embodiments of the present invention.

In order to validate the anti-CdtB antibodies, western blots were prepared with purified CdtB. Using both antibodies generated to whole CdtB (wAb) (FIG. 5a) and antibody to the highly antigenic 18 residue sequence of CdtB (haAb) (FIG. 5b) both recognized the CdtB as an active band at 27 kDa (the molecular weight of CdtB). Rabbit preimmune serum did not recognize CdtB and blocking the haAb with the peptide resulted in no visible band (FIG. 5c).

Figure 6:
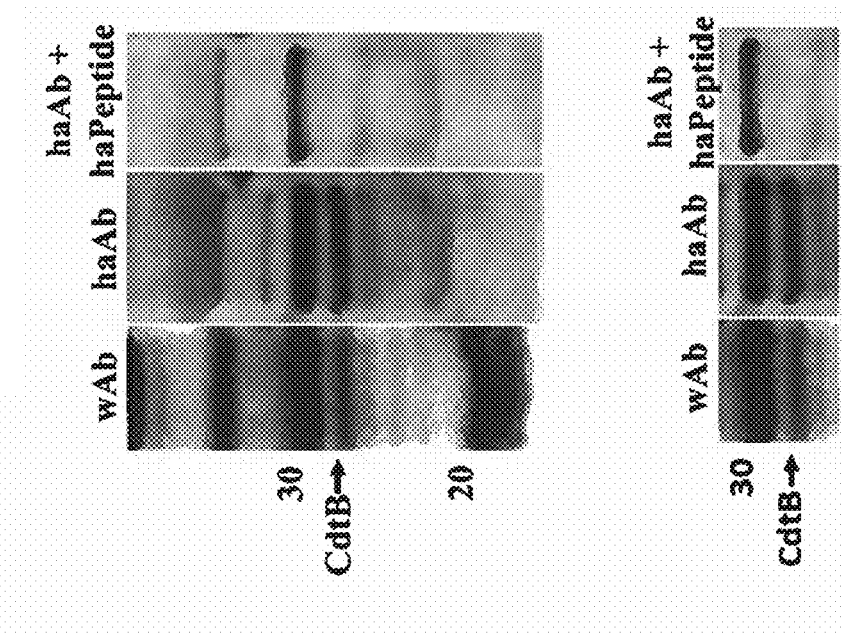
FIG. 6 depicts Western blot of C. lysates vs. antibody in accordance with various embodiments of the present invention.

To validate that the antibody recognized CdtB in *C. jejuni*, another western blot was prepared and run with a lysate of *C. jejuni* 81-176. This demonstrated that wAb (FIG. 6a) and haAb (FIG. 6b) recognized the CdtB as an active band at 27 kDa (the molecular weight of CdtB). Blocking the haAb with peptide eliminated detection of a band at 27 kDa (FIG. 6c).

wAb in Rats Exposed and Unexposed to *C. jejuni*

Figure 8:
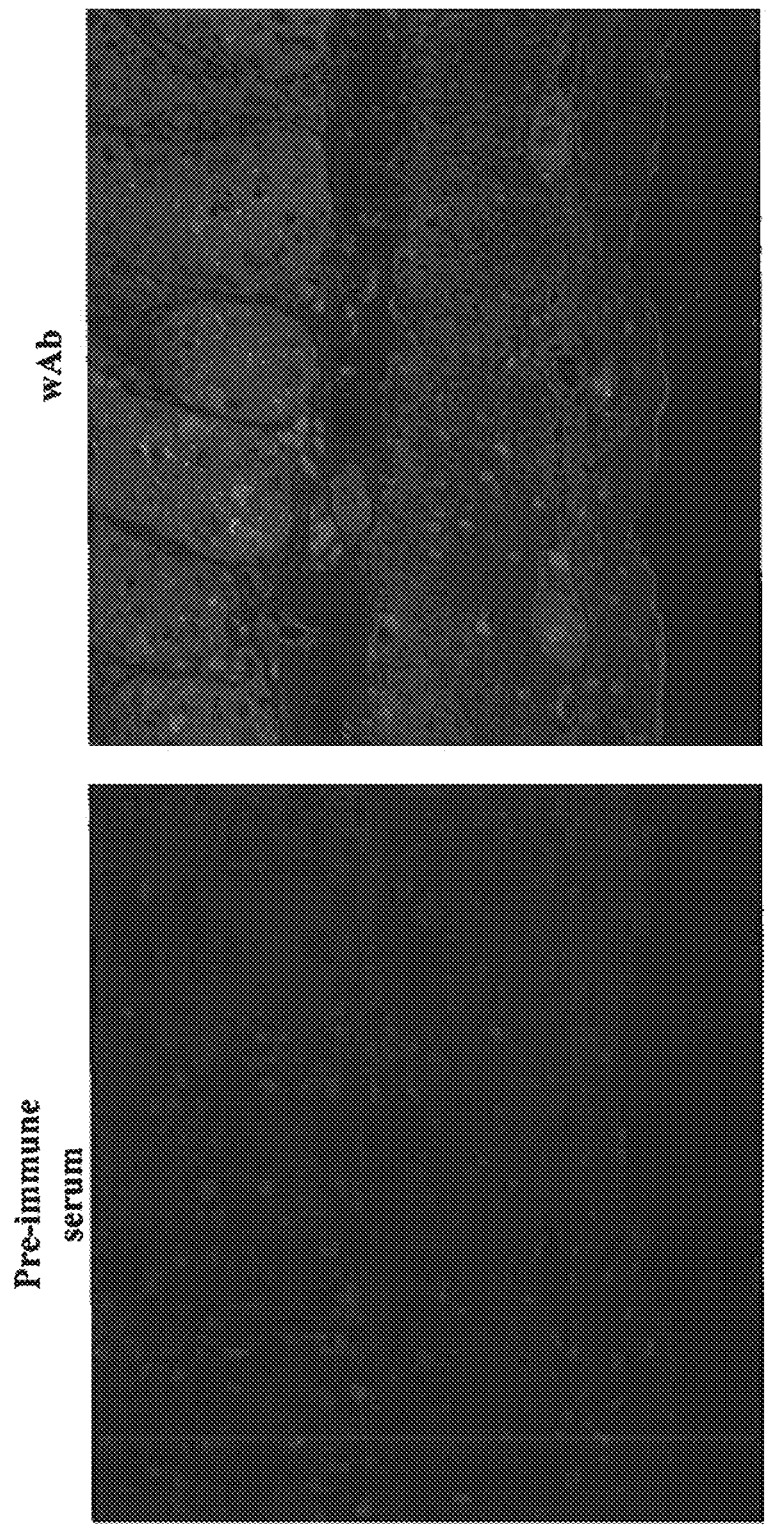
FIG. 8 depicts confocal imaging of sample from acute rats, day 2; preimmune vs. *Campylobacter jejuni* in accordance with various embodiments of the present invention.
Figure 9:
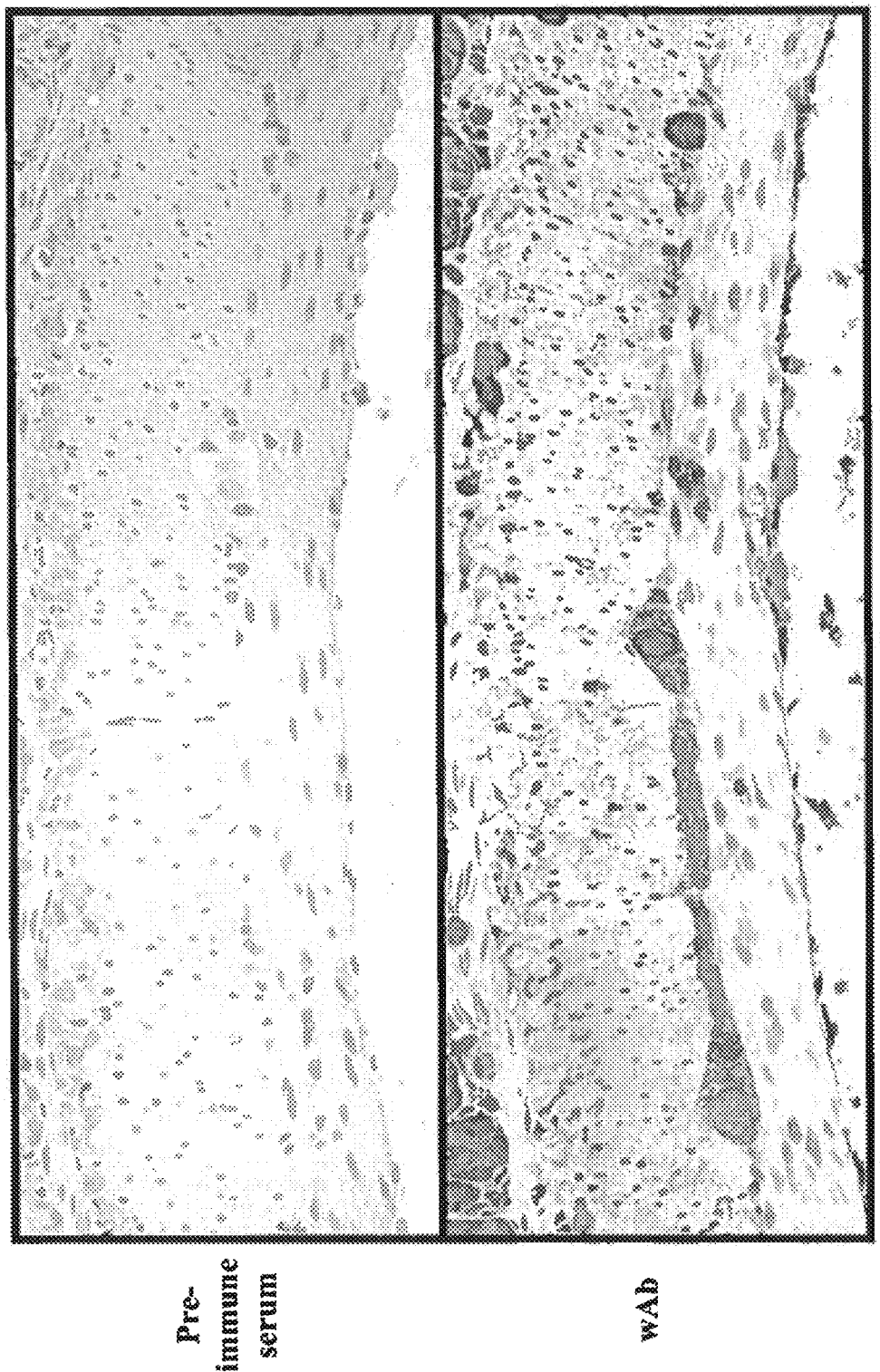
FIG. 9 depicts immunohistochemistry of control sample in accordance with various embodiments of the present invention.
Figure 10:
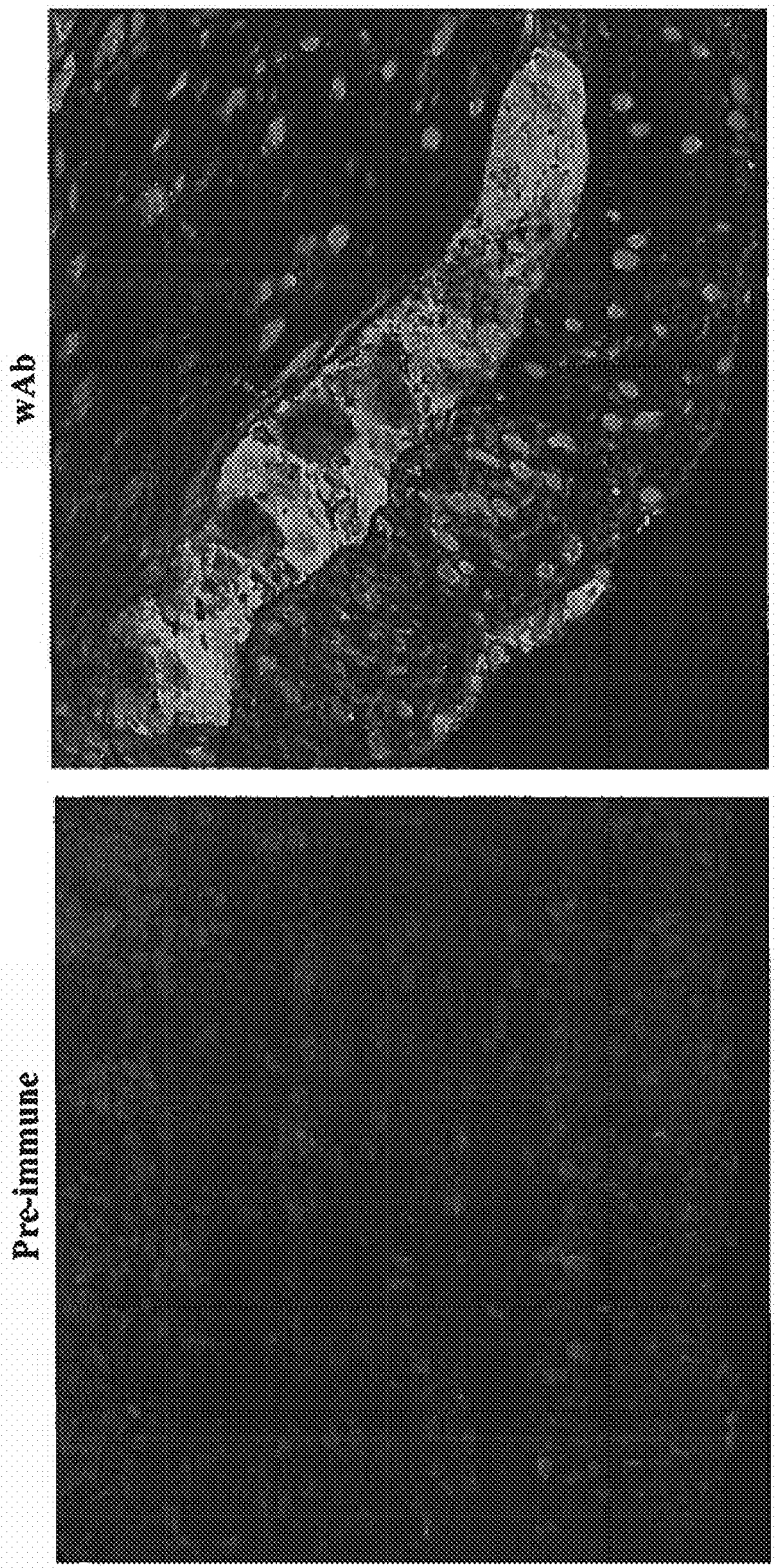
FIG. 10 depicts confocal imaging of control sample; preimmune vs. *Campylobacter jejuni* in accordance with various embodiments of the present invention.

Two groups of rats were compared in this study using immunostaining. In FIGS. 3a and b, rat ileum was examined 2 days after gavage with live *C. jejuni* 81-176. Pre-immune serum produced no staining. Rats exposed to *C. jejuni* 81-176 with active infection demonstrated extensive staining for wAb which included mucosal surface and crypts. Deep tissue components most identified were the myenteric ganglia, interstitial cells of Cajal and other neural structures. Identical localization was seen with the immunofluorescent technique (FIGS. 8a and b). However, the same pattern was seen with both immunohistochemistry (FIGS. 9a and b) and immunofluorescence (FIGS. 10a and b) for rats that were never exposed to *C. jejuni*. This suggested the antibody to CdtB was cross reacting with a native rat protein most prominently located in the area of gut neural elements suggesting molecular mimicry.

Immunohistochemical Localization of Anti-CdtB in Human Ileum

Figure 11:
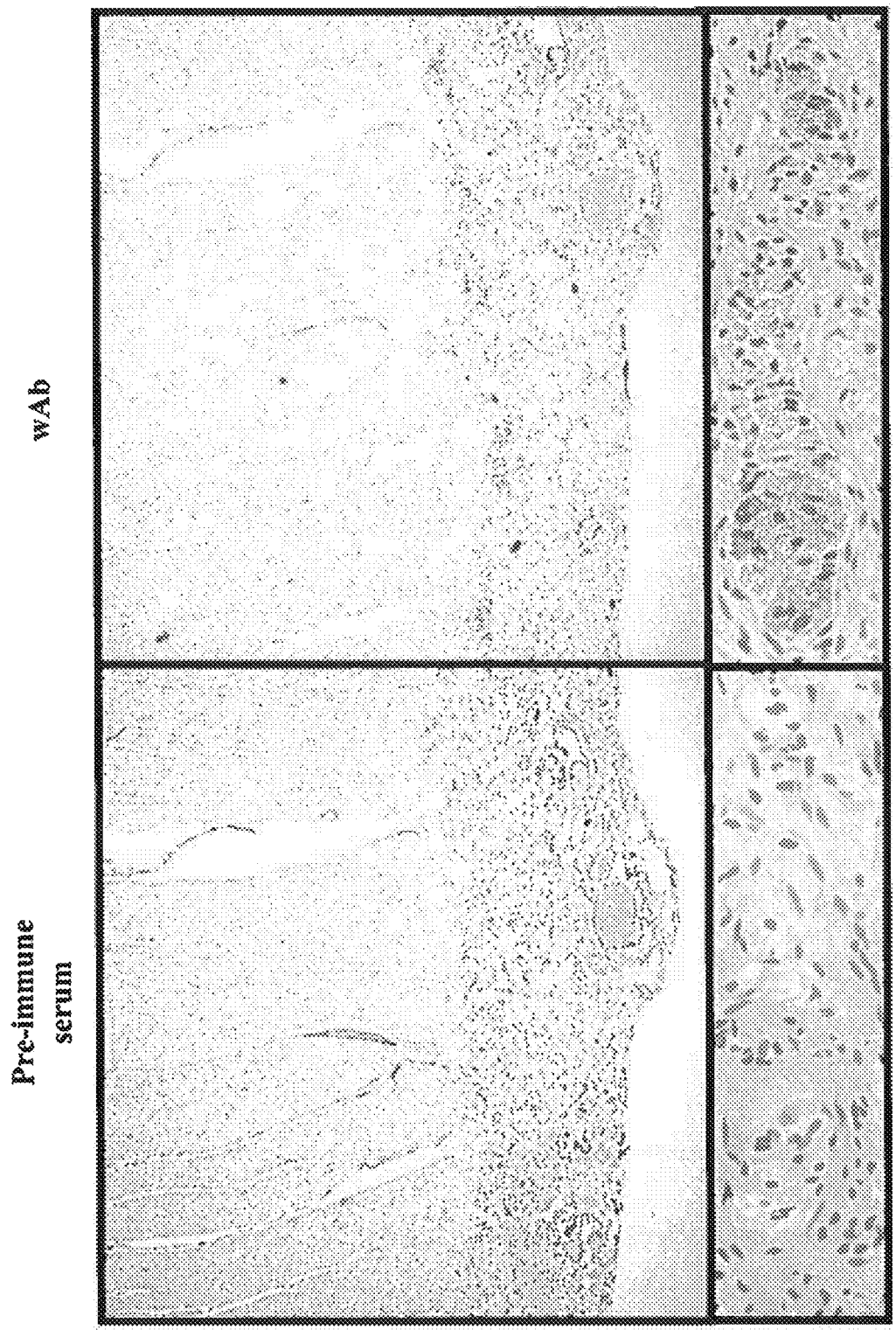
FIG. 11 depicts immunohistochemistry of human samples in accordance with various embodiments of the present invention.

Using human full thickness ileal tissue on immunohistochemistry, wAb again appeared to localize to the neural elements of the myenteric plexus (FIGS. 11a and b). Since these subjects were not IBS subject, the antibody to CdtB was assumed to be binding to a native protein.

Colocalization of Anti-CdtB with Other Neural Markers.

Figure 12:
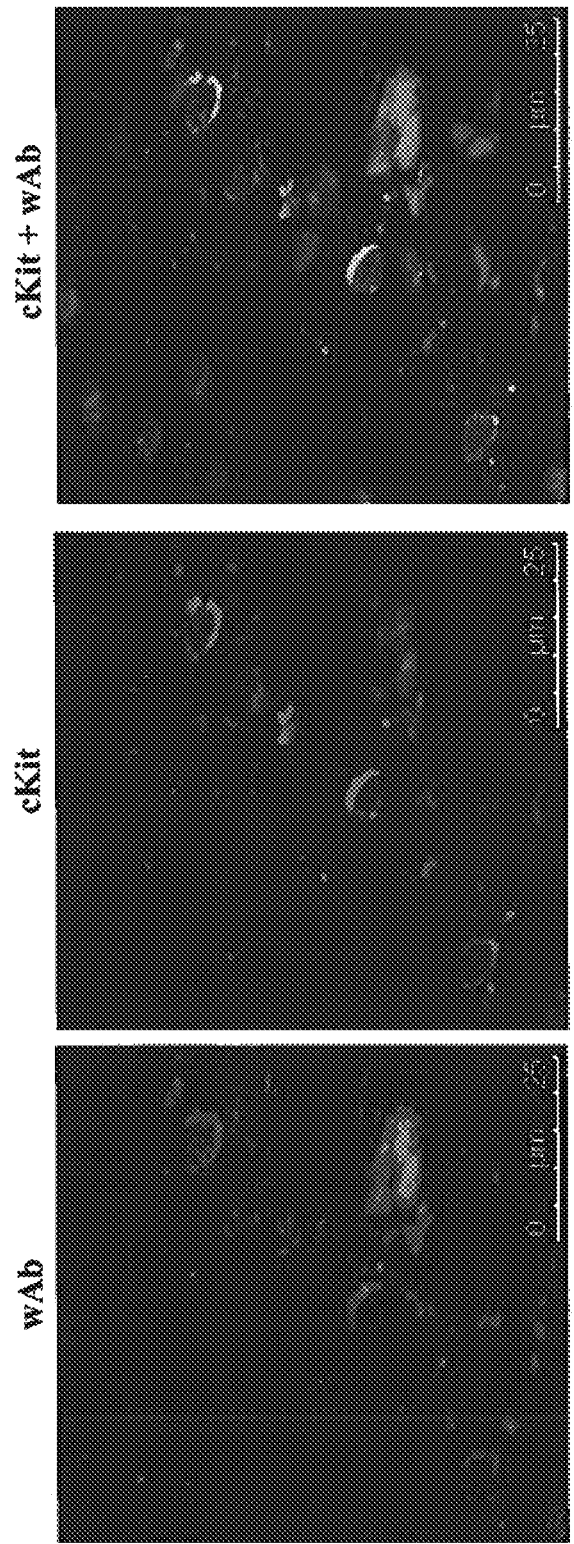
FIG. 12 depicts confocal imaging of control sample, ckit, and colocolization in accordance with various embodiments of the present invention.
Figure 13:
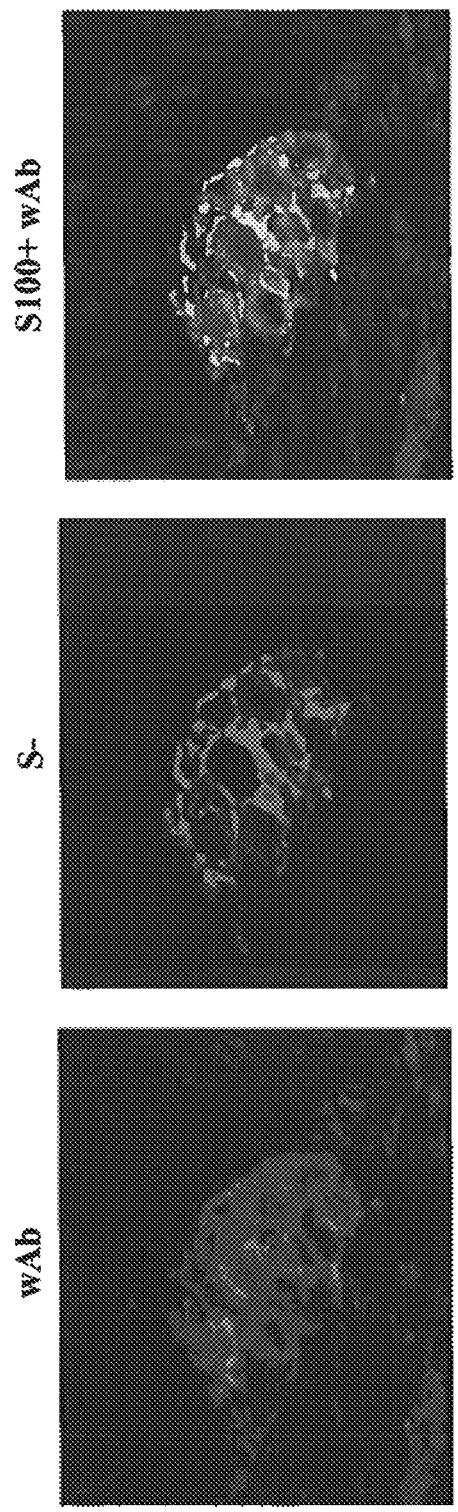
FIG. 13 depicts confocal imaging of control sample, s100, and colocolization in accordance with various embodiments of the present invention.

To demonstrate the specificity for mimicry to components of the enteric nervous system, 3 antibody markers (S-100 for enteric neurons, PGP 9.5 for ganglia and anti-c-kit for ICC) were compared to the wAb anti-CdtB antibody. From studies in all groups of rats including control rats, anti-CdtB co-localized both to ICC (with c-kit) (FIGS. 12a-c), neurons (FIGS. 13a-c) (with S-100). While co-localized, the staining for c-kit is a cell membrane stain and S-100 a nuclear stain. The anti-CdtB wAb appeared localized to the cytosolic component of the enteric neuronal cells (both ICC and neurons).

Validating Molecular Mimicry in Humans

Figure 14:
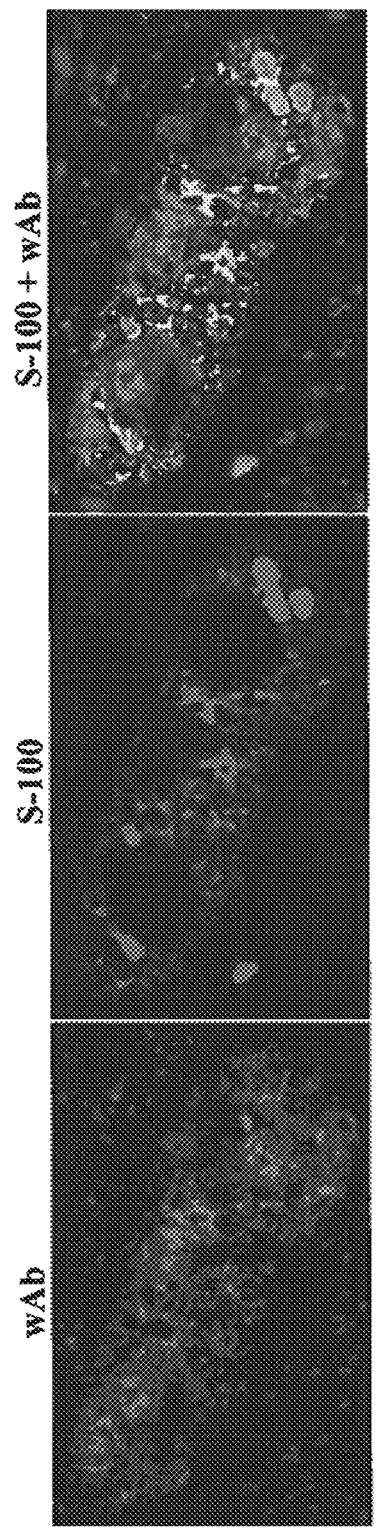
FIG. 14 depicts confocal imaging of human, S100, and colocolization in accordance with various embodiments of the present invention.
Figure 15:
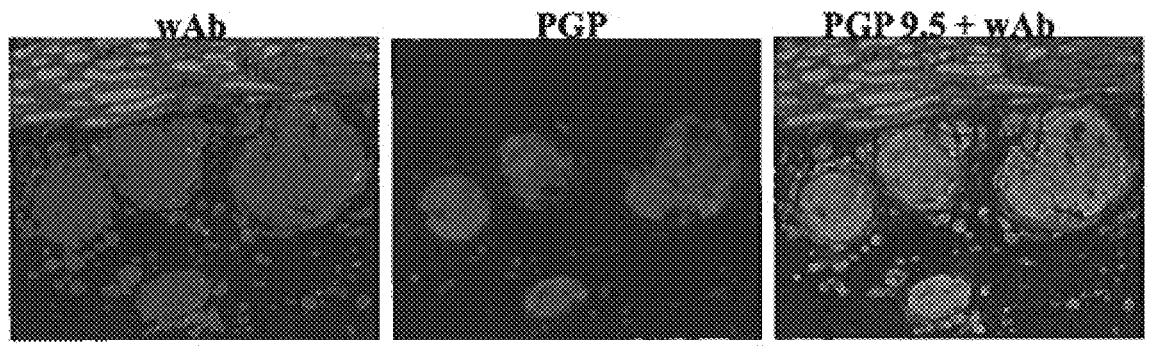
FIG. 15 depicts confocal imaging of human, PGP 9.5, and colocolization in accordance with various embodiments of the present invention.

To evaluate the potential for anti-CdtB wAb to demonstrate molecular mimicry in human small bowel, full thickness sections of ileum from right hemicolectomy specimens were mounted and stained as in the rats above. Similar to rats, colocalization was seen in with c-kit, S-100 (FIGS. 14a-c) and PGP 9.5 (FIGS. 15a-c).

Molecular Mimicry towards a Cytosolic Protein of Enteric Neurons

Figure 16:
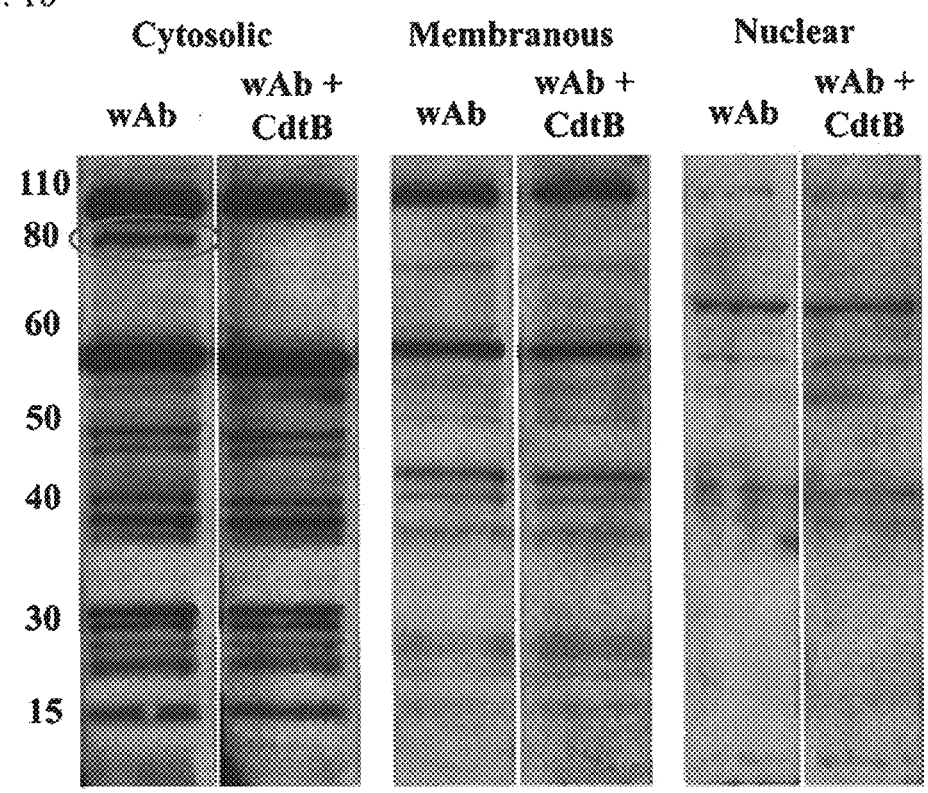
FIG. 16 depicts Western blot of fractionation & block in accordance with various embodiments of the present invention.
Figure 17:
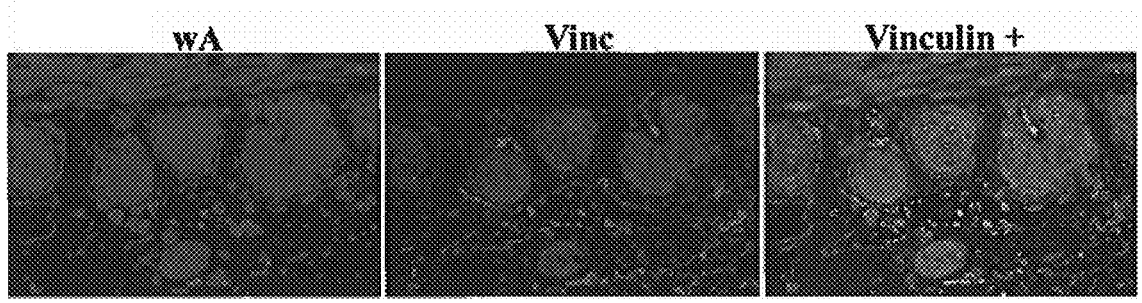
FIG. 17 depicts confocal imaging of human, vinculin, and colocolization in accordance with various embodiments of the present invention.

Using lysates of enteric neuronal stem cells, wAb anti-CdtB antibodies demonstrate a band at 117 kDa (FIGS. 16a and c). In fractionating the lysates, the 117 kDa band was located in the cytosolic fraction of the lysate (FIG. 16a). Blocking experiments using whole CdtB to block the antibody blocks binding to this 117 kDa protein (FIG. 16a). Mass spectroscopy identified the protein candidate in this band as vinculin. In the human tissue, confocal microscopy demonstrates colocalization of vinculin and wAb (FIGS. 17a-c).

Demonstration of Anti-CdtB In Vivo in Rat Model of IBS

Figure 18:
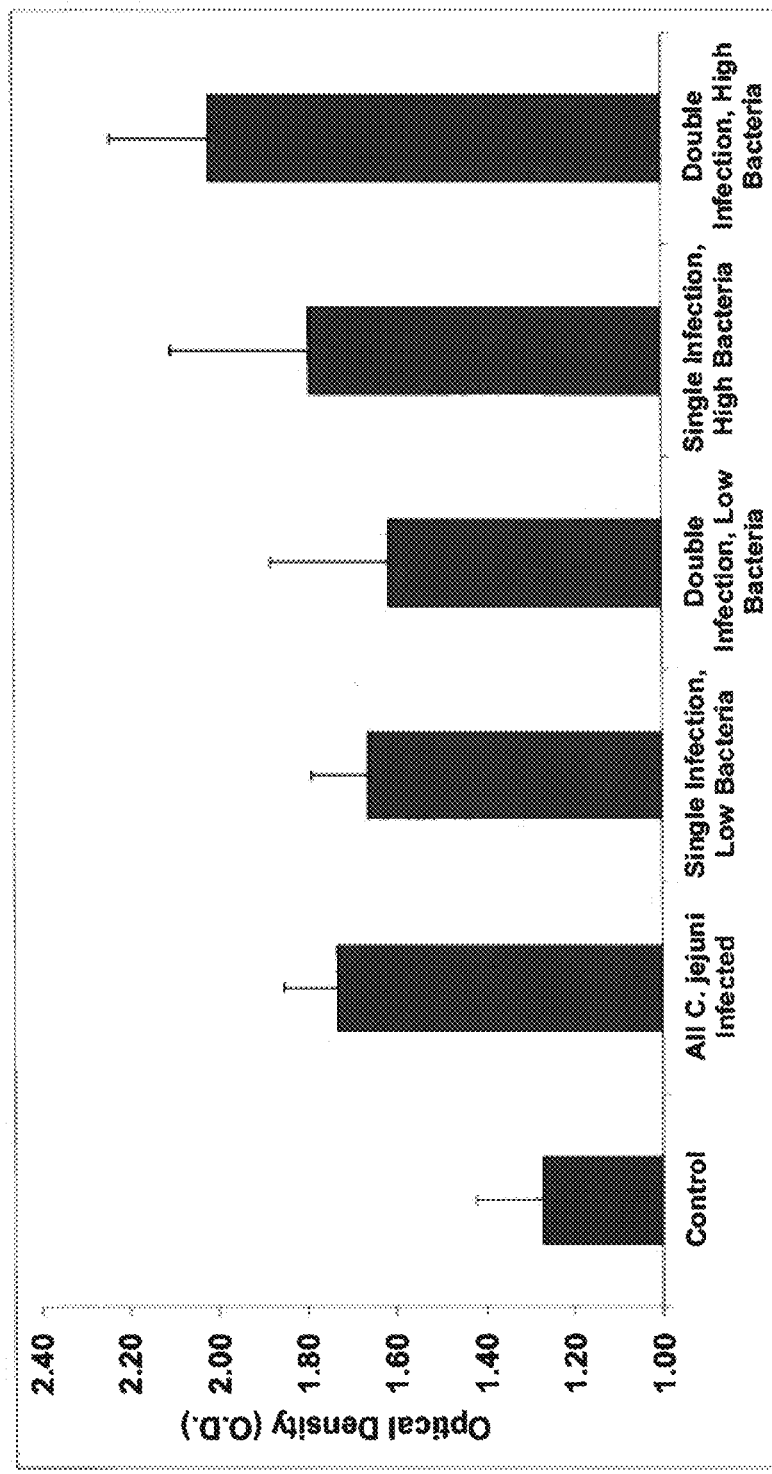
FIG. 18 depicts a difference between high and low bacteria counts in small bowel of rats in accordance with various embodiments of the present invention.
Figure 19:
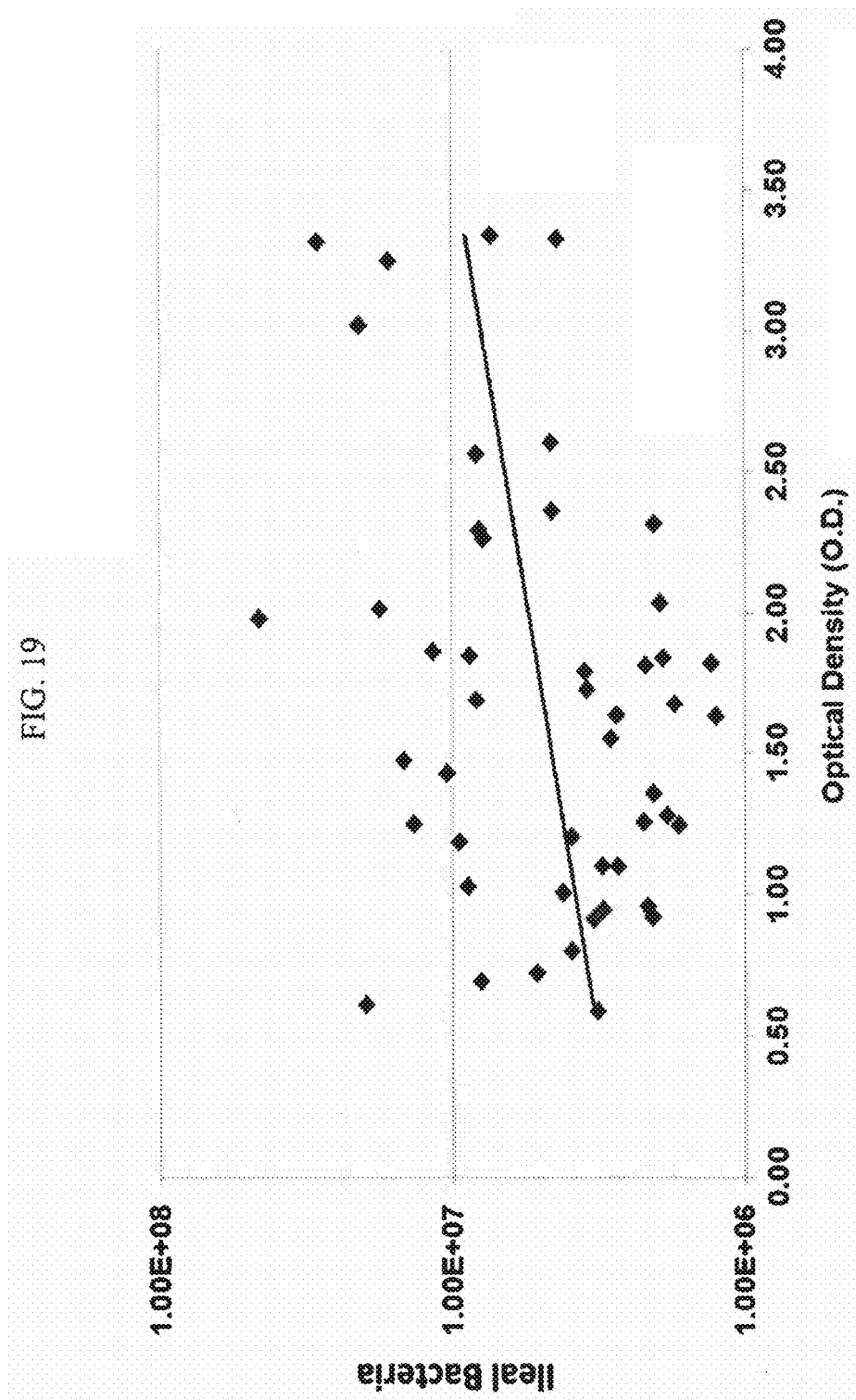
FIG. 19 depicts a comparison between antibody titers and SIBO levels (r=0.3, P=0.04) in accordance with various embodiments of the present invention.

To demonstrate the role of antibodies to CdtB in the phenotype of post-infectious IBS, an ELISA was developed using *C. jejuni* anti-CdtB. In this study, control rats, rats with single exposure to *C. jejuni* and rats with two exposures to *C. jejuni*, 2 months apart, were tested and compared to the outcome of small intestinal bacterial overgrowth by PCR of small bowel enteric flora. In FIG. 18 it is apparent that anti-CdtB was not only dependent on the previous infection with *C. jejuni* but also the development of small intestinal bacterial overgrowth. Among rats receiving *C. jejuni*, those with bacterial overgrowth had higher titers of anti-CdtB than those with no bacterial overgrowth irrespective of number of infections with *C. jejuni*. This is further demonstrated by the significant correlation between circulating anti-CdtB and greater degree of small intestinal bacterial overgrowth based on qPCR of total bacteria (FIG. 19).

Demonstration of Anti-CdtB and Anti-Vinculin in Humans with Post-Infectious IBS

Figure 20:
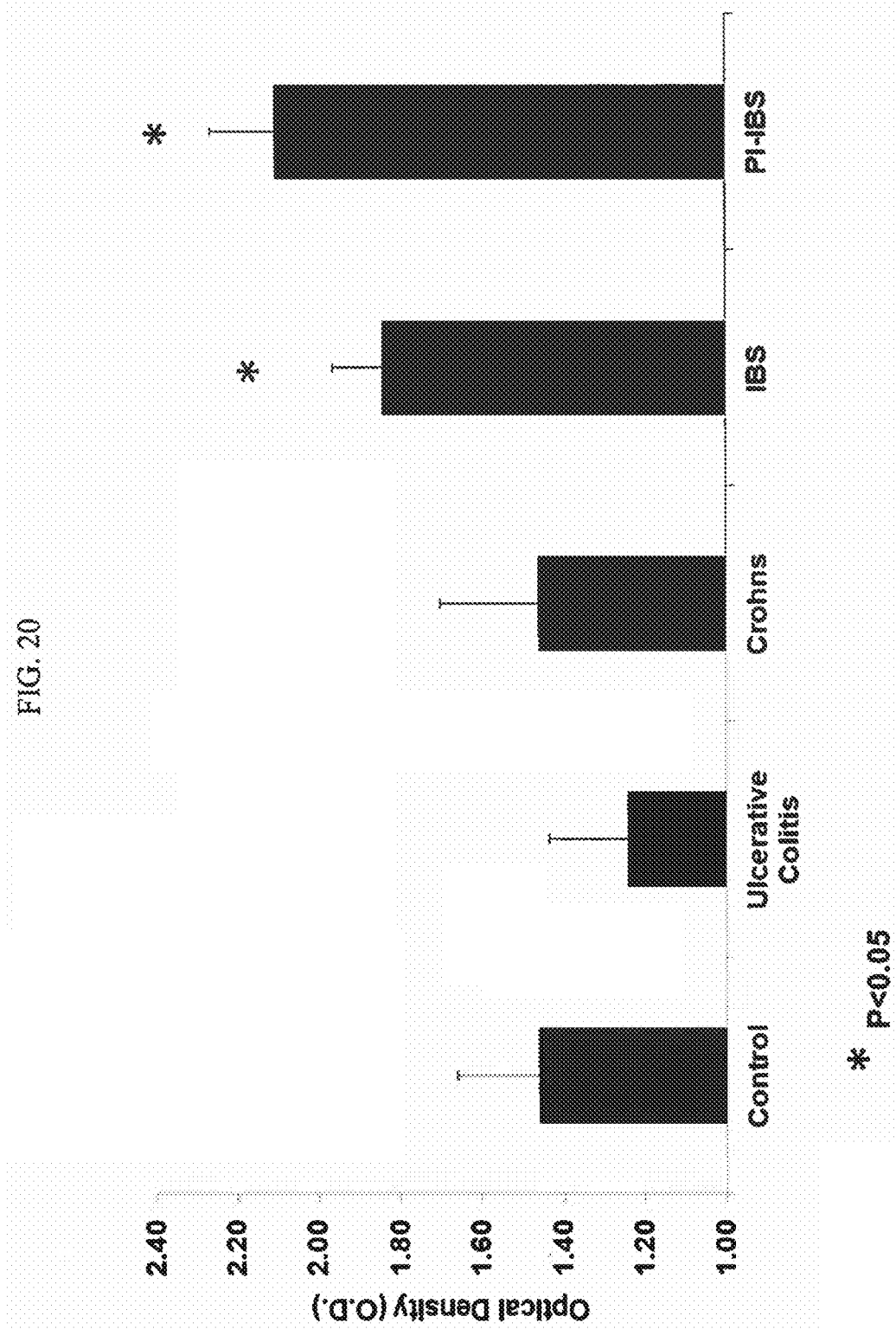
FIG. 20 depicts cdtB antibodies in human serum in accordance with various embodiments of the present invention.

In this final experiment, serum was collected from 43 humans with IBS, 20 healthy subjects and 20 subjects with inflammatory bowel disease (10 subjects with Crohn's disease and 10 subjects with ulcerative colitis). Using absolute values, subjects with IBS had the greater titer of anti-CdtB antibodies compared to IBD or controls (FIG. 20) Using an OD>2 as a diagnosis of IBS and post-infectious IBS, this threshold was able to identify IBS with a sensitivity of 85.7% and specificity of 67.2% in comparison to inflammatory bowel disease (Table 2b).

TABLE 2b

Test dynamics of anti-CdtB to diagnose IBS

|  |  | ELISA Positive | |
| --- | --- | --- | --- |
|  |  | Yes | No |
| IBS vs. IBD | IBS | 18 | 20 |
|  | IBD | 3 | 17 |
| Test Characteristics | Sensitivity | 85.7% |  |
|  | Specificity | 67.2% |  |

Figure 21:
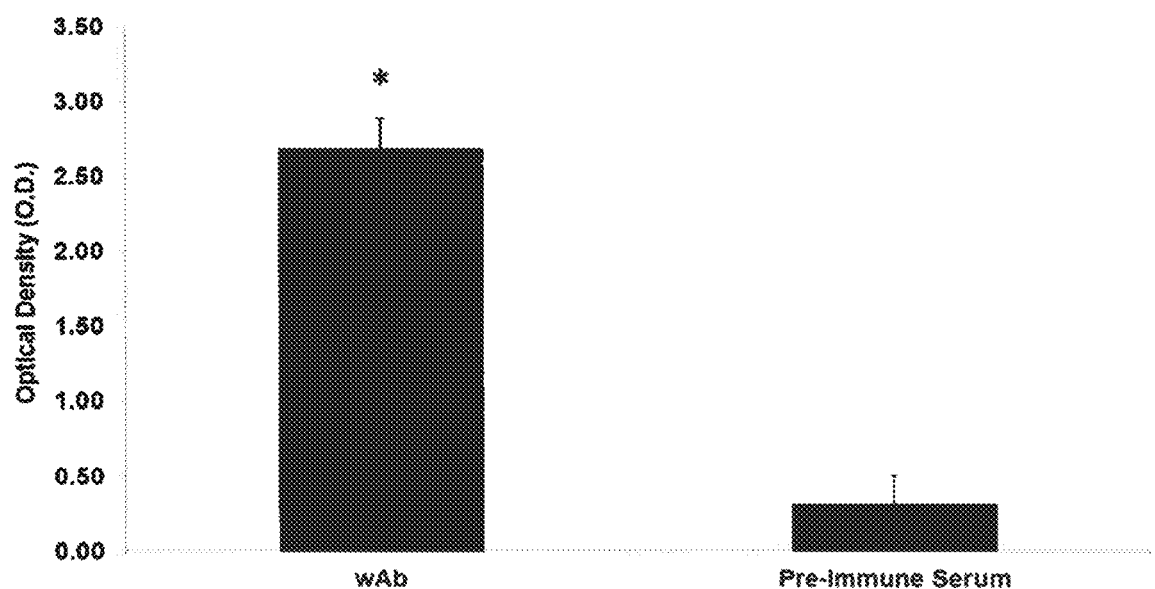
FIG. 21 depicts cdtB and pre-immune serum vs. vinculin protein in accordance with various embodiments of the present invention.
Figure 22:
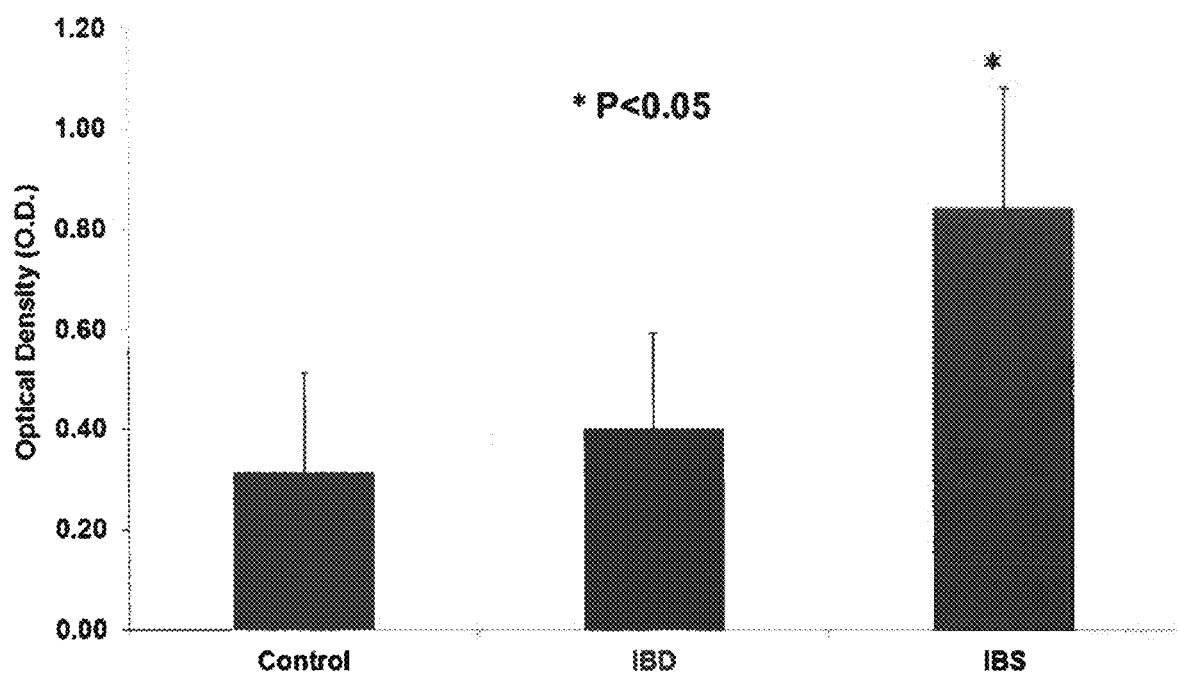
FIG. 22 depicts vinculin antibodies in human serum in accordance with various embodiments of the present invention.
Figure 24A:
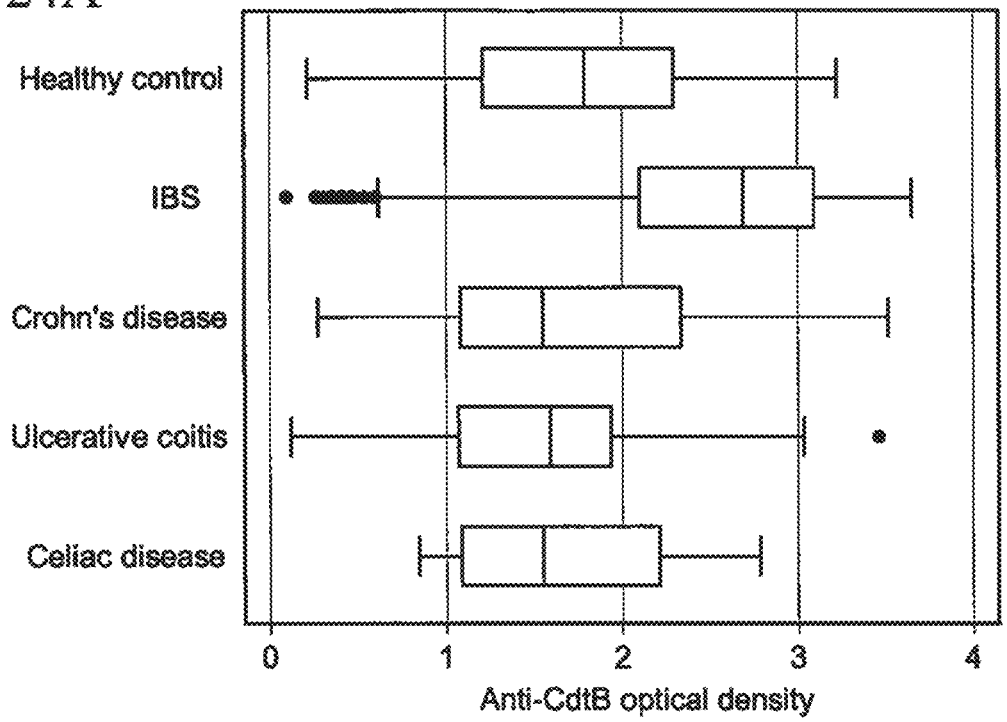
FIG. 24A depicts comparison of anti-CdtB antibody OD among the groups in accordance with various embodiments of the present invention.
Figure 24B:
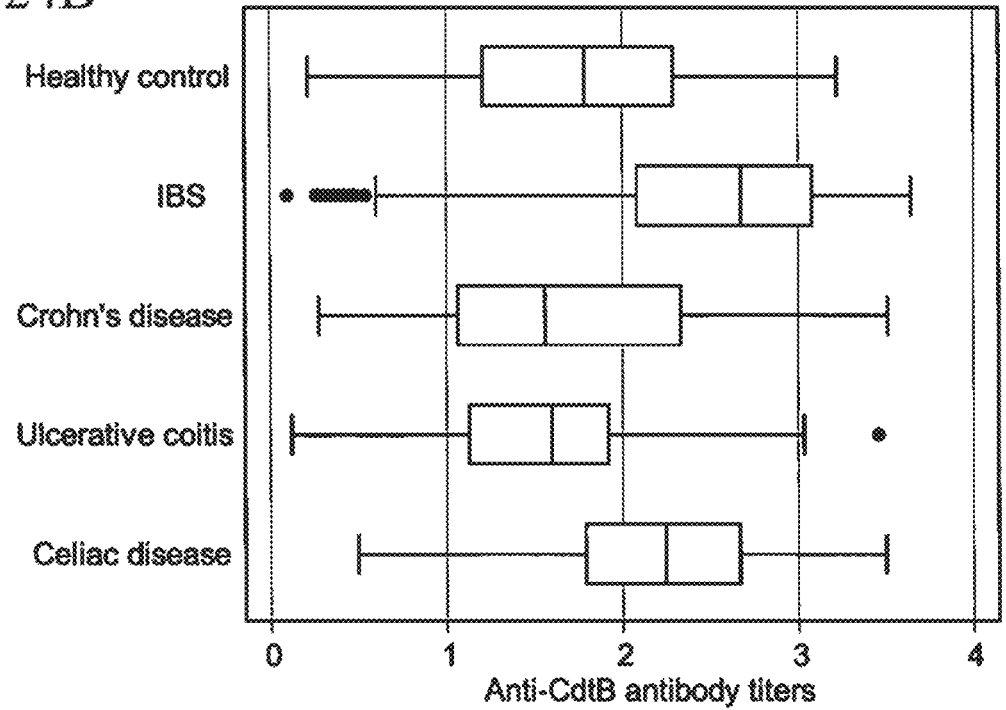
FIG. 24B depicts comparison of optical density (OD) for the anti-CdtB antibody among the groups. Dots represent outlier subjects beyond the whisker plot. Titers were higher in IBS subjects in comparison to any other group (p<0.001) Titers were higher in subjects with celiac disease as compared to healthy controls and IBD subjects (p<0.001)
Figure 25A:
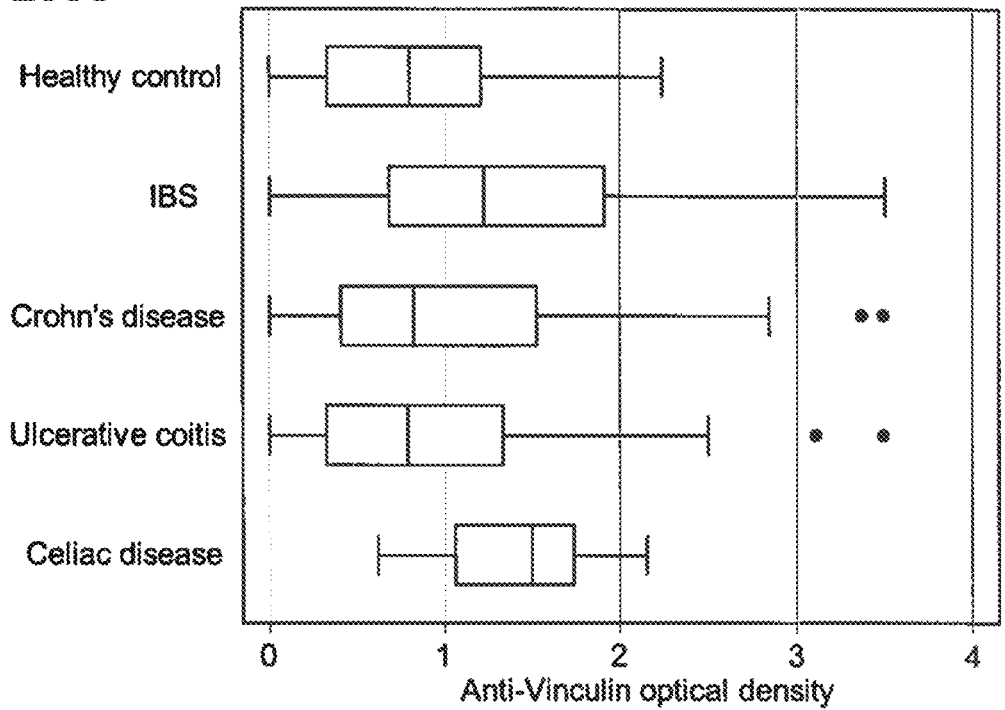
FIG. 25A depicts comparison of anti-vinculin antibody OD among the groups in accordance with various embodiments of the present invention.
Figure 25B:
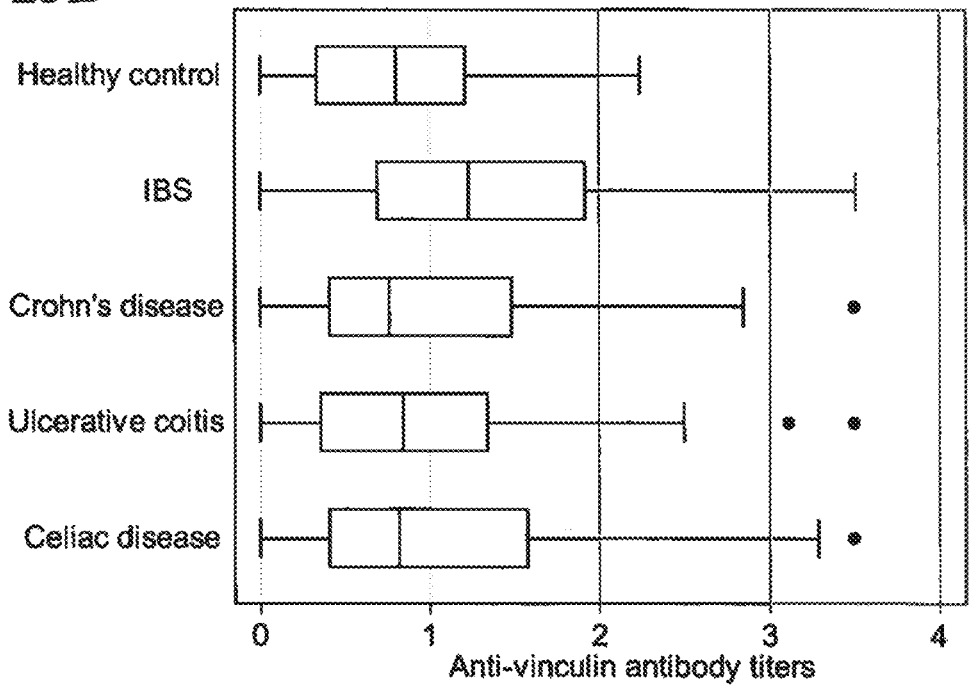
FIG. 25B depicts comparison of optical density (OD) for the anti-vinculin antibody among the groups. Dots represent outlier subjects beyond the whisker plot. Titers were higher in IBS subjects as compared to any other group (p<0.001)
Figure 26A:
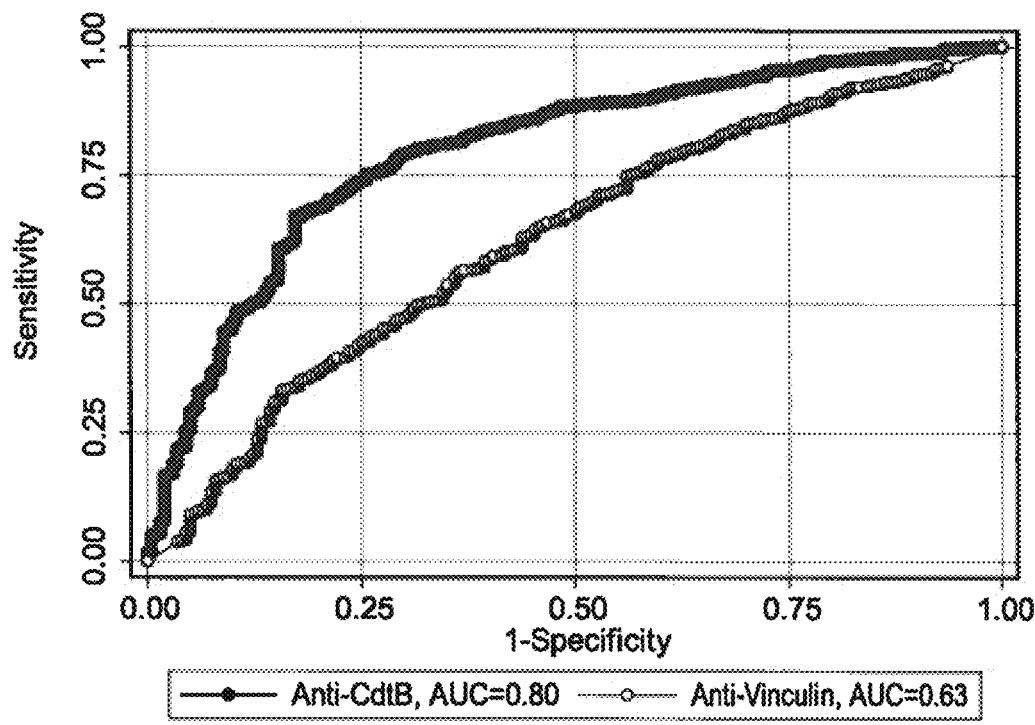
FIG. 26A depicts receiver operator curve (ROC) comparing anti-CdtB and anti-vinculin levels between IBS subjects and all non-IBS subjects in the study in accordance with various embodiments of the present invention. (Anti-CdtB—top line; anti-vinculin—bottom line.)
Figure 26B:
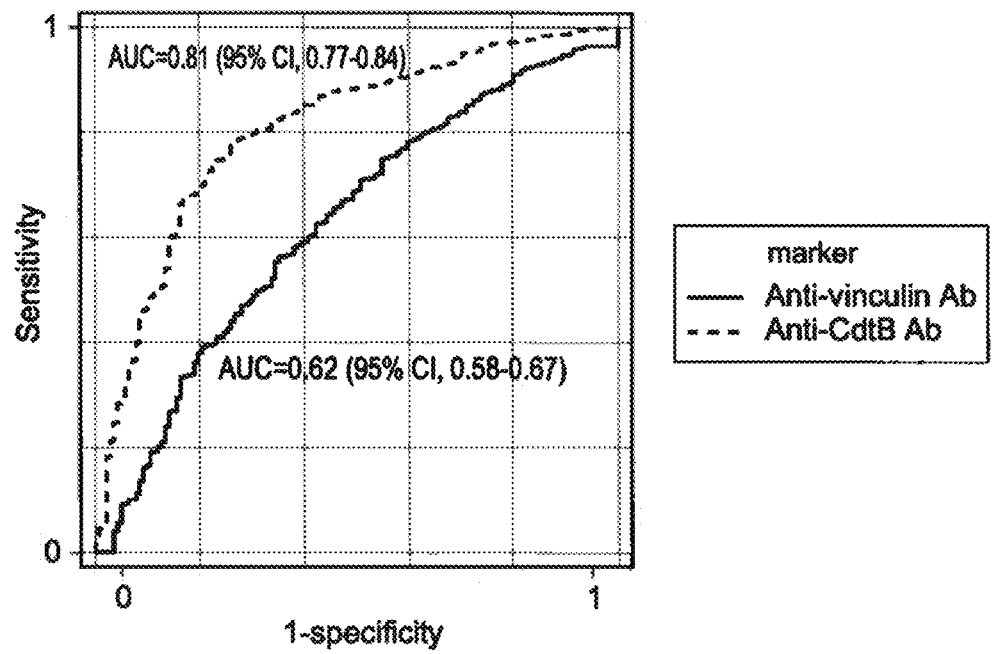
FIG. 26B depicts receiver operator curve (ROC) comparing anti-CdtB and anti-vinculin levels between IBS subjects and IBD subjects in the study. AUC, Area under the curve; CI, confidence interval. (Anti-CdtB—top line; anti-vinculin—bottom line.)
Figure 26C:
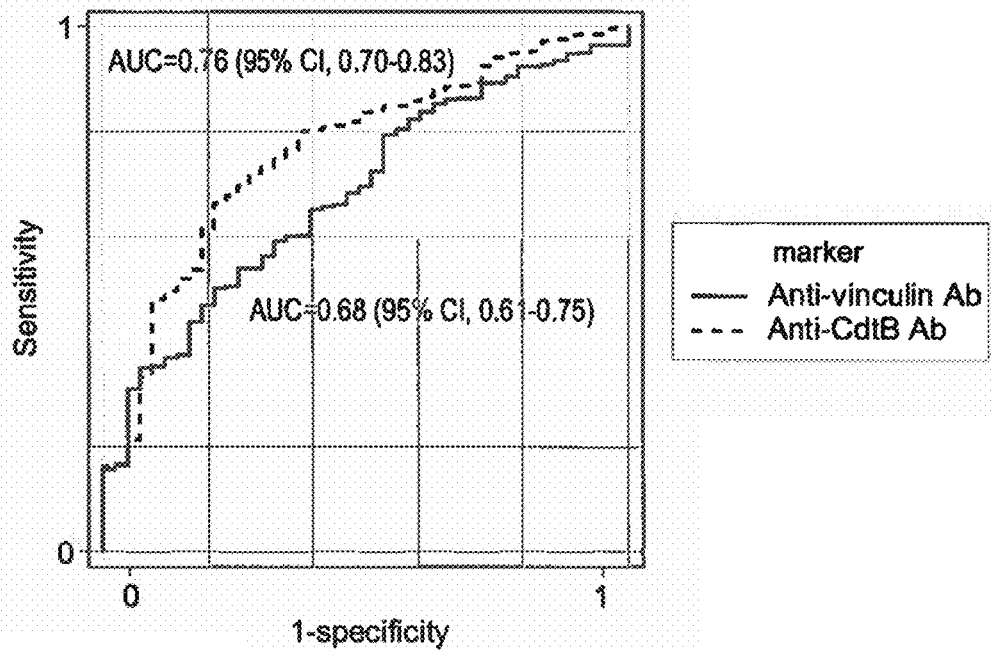
FIG. 26C depicts receiver operator curve (ROC) comparing anti-CdtB and anti-vinculin levels between IBS subjects and healthy subjects in the study. (Anti-CdtB—top line; anti-vinculin—bottom line.)
Figure 27:
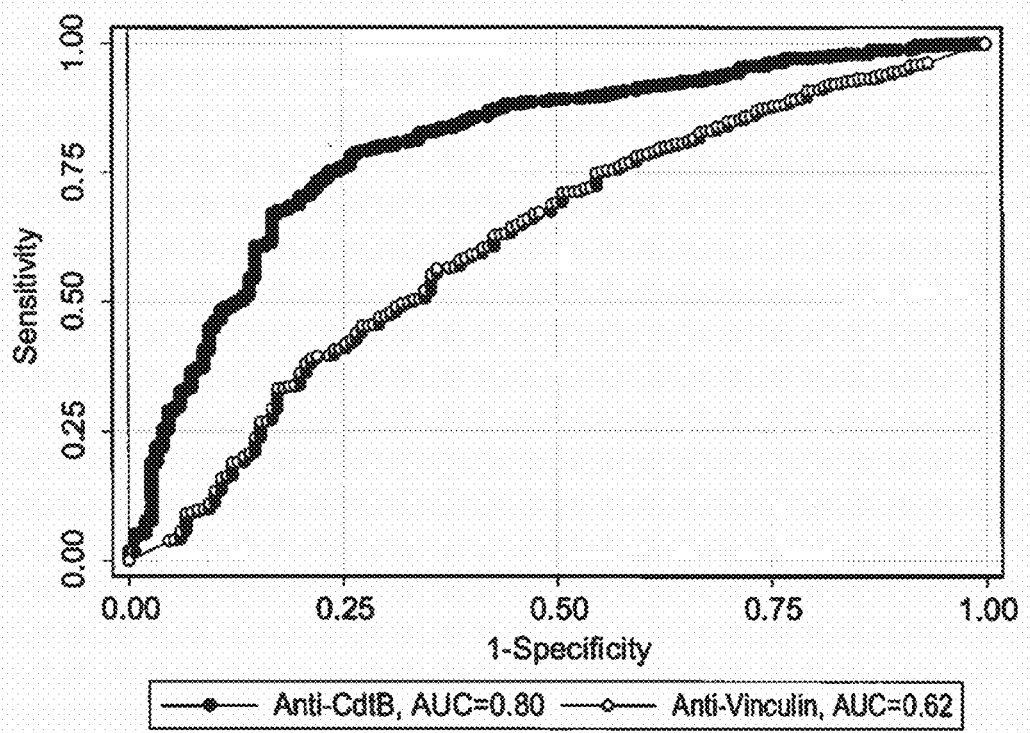
FIG. 27 depicts receiver operator curve (ROC) comparing anti-CdtB and anti-vinculin levels between IBS subjects and all IBD subjects in the study in accordance with various embodiments of the present invention. (Anti-CdtB—top line; anti-vinculin—bottom line.)
Figure 28:
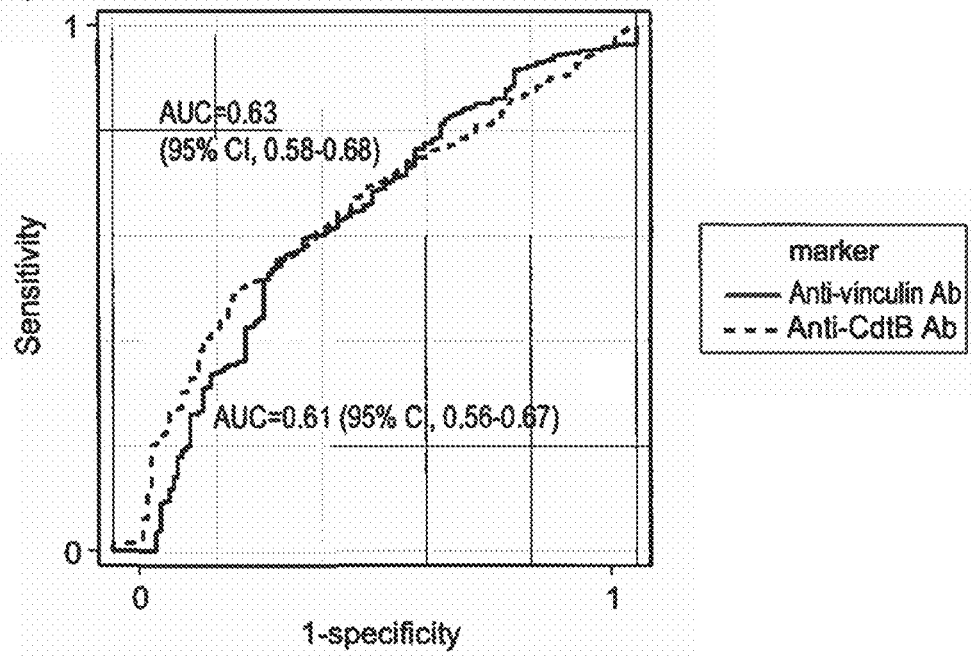
FIG. 28 depicts receiver operator curve (ROC) comparing anti-CdtB and anti-vinculin levels between IBS and celiac subjects. (Anti-CdtB—top line at the beginning; anti-vinculin—bottom line at the beginning.)
Figure 29:
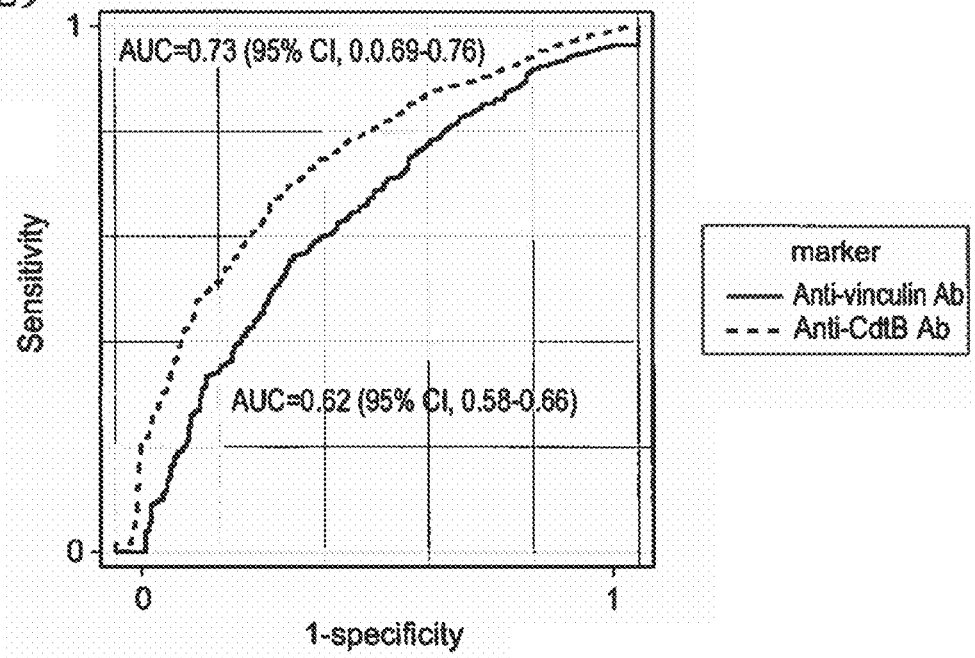
FIG. 29 depicts receiver operator curve (ROC) comparing anti-CdtB and anti-vinculin levels between IBS and non-IBS subjects with chronic diarrhea (i.e., CD, UC and celiac disease). (Anti-CdtB—top line; anti-vinculin—bottom line.)
Figure 30:
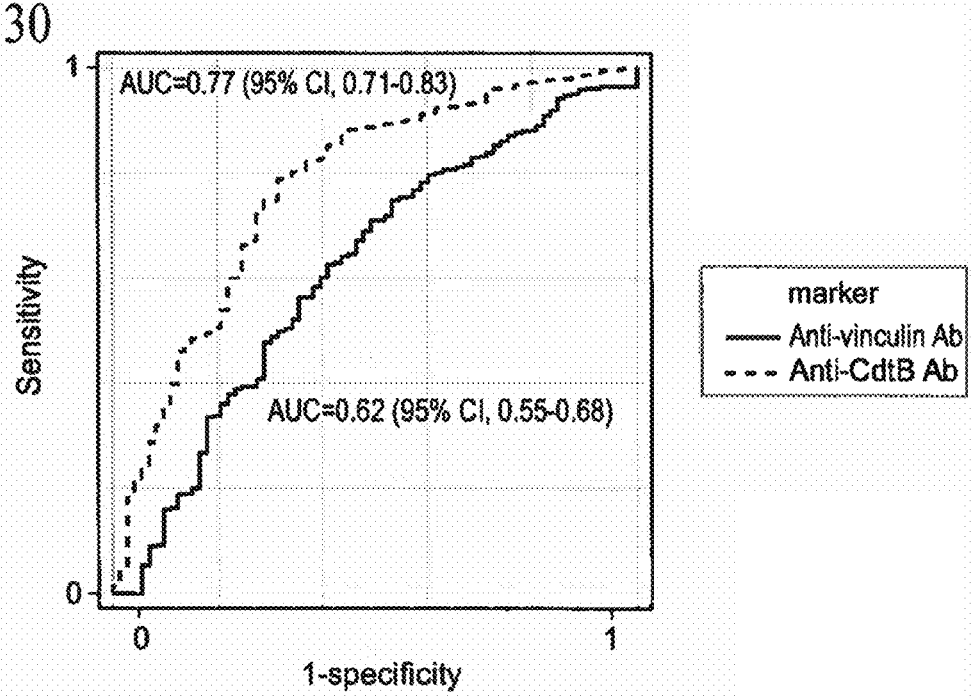
FIG. 30 depicts receiver operator curve (ROC) comparing anti-CdtB and anti-vinculin levels between IBS and CD subjects. (Anti-CdtB—top line; anti-vinculin—bottom line.)
Figure 31:
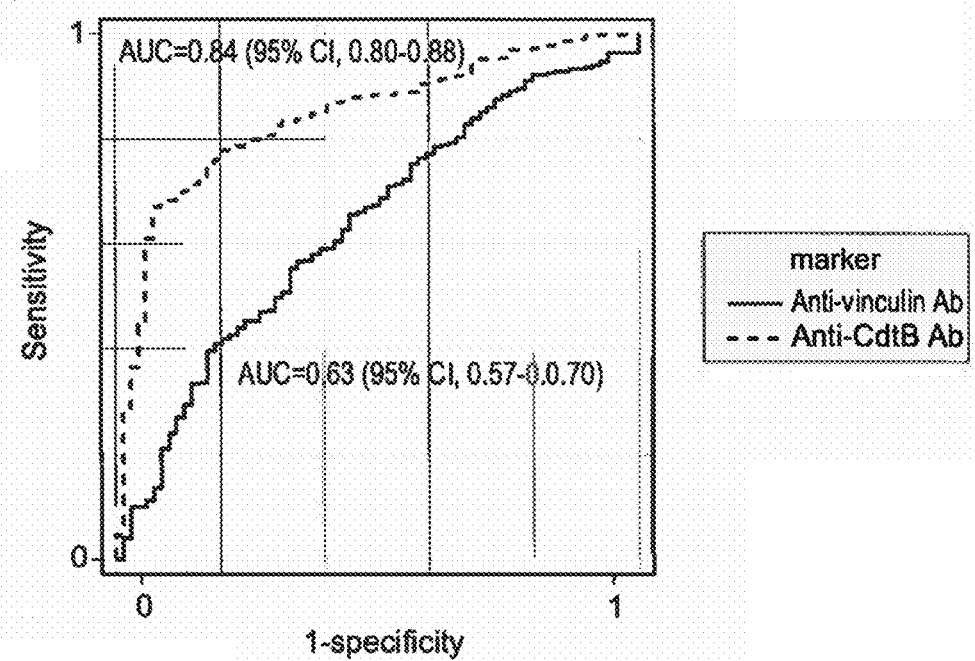
FIG. 31 depicts receiver operator curve (ROC) comparing anti-CdtB and anti-vinculin levels between IBS and UC subjects. (Anti-CdtB—top line; anti-vinculin—bottom line.)

Using vinculin as the ELISA substrate, applying pre-immune serum to the wells produced a very low response. However, the application of wAb to the wells produced a vigorous response. This suggested that anti-CdtAb strongly react to vinculin in the ELISA (FIG. 21). When ELISA testing for vinculin was conducted using serum from the three human groups, again there was significantly higher titers of anti-vinculin in IBS subjects.

Finally, ELISA using latrophillin or c-kit demonstrated no difference between IBS, controls and subjects with inflammatory bowel disease suggesting the differences were not due to non-specific binding (data not shown).

Circulating Antibodies to Cytolethal Distending Toxin B Correlates with the Development of Small Intestinal Bacterial Overgrowth in a Rat Model of Post-Infectious IBS The level of serum anti-CdtB antibodies in the rat model of post-infectious IBS was examined and correlated with the development of SIBO.

Methods: Male Sprague-Dawley rats (n=100) were obtained as infants and randomized to three groups. The first group was gavaged with *C. jejuni* 81-176 ($10^8$ cfu/mL) as juveniles and two months later as adults (J+/A+). The second group was gavaged with *C. jejuni* only as adults (J−/A+). The third group was never exposed to *C. jejuni* (controls). Three months after the adult infection all rats were euthanized. After euthanasia, segments of ileum, jejunum and duodenum were ligated and removed as previously described (Chatterjee, et al). From each bowel segment, DNA was extracted from luminal contents and qPCR using universal bacterial primers was used to determine the presence or absence of SIBO. SIBO was defined as bacterial counts in excess of 2 standard deviations above mean of controls for each segment. At euthanasia, blood was taken and serum isolated. A 96 well plate was coated with CdtB to which rat serum was added and incubated for 90 minutes. Wells were washed and incubated with a fluorescent secondary antibody and read on a plate reader.

Results: ELISA for detection of anti-CdtB in serum of control rats demonstrated an optical density (OD) of 1.27±0.15. All rats exposed to *C. jejuni* had a greater OD of 1.73±0.12 (P<0.05). In the J−/A+ group, the single exposure to *C. jejuni* resulted in SIBO in 26% of rats. In J+/A+ double exposed rats, SIBO was seen in 46% (P<0.05). Anti-CdtB was greater if rats had SIBO irrespective of whether they had a single (1.79±0.31) or double exposure (2.02±0.22) to *C. jejuni*. Rats that did not have SIBO had titers <1.7. Plotting the level of bacteria in the ileum against the ELISA findings demonstrated a correlation between levels of bacteria and anti-CdtB (R=0.3, P<0.05).

Conclusions: Antibodies to CdtB develop after exposure to *C. jejuni* but appear to develop in a pattern that relates to the development of SIBO more than the number of exposures to *C. jejuni*. Based on the affinity for ICC and ganglia, the inventors believe that these antibodies are important to the pathophysiology of IBS perhaps by affecting gut motor function leading to SIBO.

Antibodies to Cytolethal Distending Toxin B and Auto-Antibodies to Human Vinculin are Elevated in IBS Subjects In an animal model of post-infectious IBS, antibodies to CdtB bind neurological elements in the gut wall including interstitial cells of Cajal (ICC) and ganglia through a process of molecular mimicry/autoimmunity. The protein on these nerves to which this mimicry occurs was found to be vinculin, and antibodies to vinculin predict SIBO in rats. The inventors translate these antibody tests to humans to determine the titers of anti-CdtB and anti-vinculin antibodies in the serum of subjects with IBS and inflammatory bowel disease (IBD).

Methods: Consecutive IBS subjects meeting Rome III criteria were recruited from a GI Motility clinic (n=45). In addition, 30 subjects with IBD were recruited from a tertiary care IBD clinic. Finally, 20 healthy controls were identified based on a negative symptom questionnaire. All subjects were consented and serum samples were obtained. An enzyme-linked immunosorbent assay (ELISA) was created by coating 96 well plates with either 0.4 μg of recombinant vinculin or 0.4 μg/mL of purified CdtB per well. Serum from each subject was added to the wells and incubated for 90 minutes. The wells were washed and then secondary antibodies were added to each well. The optical density (OD) measures were determined using a plate reader.

Results: In plates coated with CdtB, the mean OD for IBS serum was 1.89±0.12. This was significantly greater than for subjects with IBD (1.35±0.22) (P<0.05) or healthy controls (1.46±0.20) (P<0.05). In plates coated with vinculin, the mean OD for IBS serum was 0.53±0.07. This was significantly greater than for subjects with IBD (0.21±0.09) (P<0.05). There was a trend for a difference from healthy controls (0.31±0.10) (P=0.11). There was no difference between IBS-C or IBS-D for either antibody.

Conclusions: Both anti-CdtB and autoimmune anti-vinculin antibodies are detectable in IBS subjects and are seen to be elevated in IBS compared to controls and IBD. The detection of anti-CdtB and anti-vinculin suggest new clues to the diagnosis and pathophysiology of IBS. This is the first study to link acute gastroenteritis to an autoimmune process in IBS.

Molecular Mimicry Leads to Autoimmunity to Vinculin in Humans: The Missing Link in the Pathophysiology of IBS The inventors investigate the human antigen to which anti-CdtB binds.

Methods: First, non-IBS human full thickness ileal tissue (from right hemicolectomy) was obtained. Ileal sections were incubated with purified rabbit antibodies to CdtB, washed and incubated with fluorescent secondary antibodies. Colocalization studies were performed with anti-c-kit (specific for ICC), S-100 (specific for neurons) and PGP 9.5 (specific for ganglia). Next, immunoprecipitation was performed by generating a column with anti-CdtB through which a lysate of human enteric neuronal cells (Emory University) was passed. Anti-CdtB adherent protein was eluted and two western blots were performed. One was incubated with anti-CdtB and the other with anti-CdtB pre-incubated with CdtB protein (blocking peptide). A band was identified at 117 kDa, purified and identified by mass spectroscopy as human vinculin. An aliquot of 0.4 ug of commercial vinculin was coated per well in 96 well plates. Anti-CdtB was added to one series of wells, and anti-CdtB mixed with whole CdtB protein (blocking peptide) to another.

Results: Using full-thickness human ileal tissue, anti-CdtB was specific for ICC and ganglia. This was based on colocalization of anti-CdtB with anti-c-kit, PGP 9.5 and S-100 (see figure). Thus anti-CdtB appeared to be interacting with a human protein on ICCs and ganglia. Based on immunoprecipitation, a protein band was identified at 117 kDa. Using mass spectroscopy this protein was identified as human vinculin. Subsequently, human vinculin was obtained commercially and by ELISA, anti-CdtB had a high affinity for human vinculin but not the control peptide. Binding to vinculin was blocked by the CdtB peptide.

Conclusions: In the pathophysiology of post-infectious IBS, subjects develop antibodies to CdtB which have cross reactivity through molecular mimicry to vinculin, a cell membrane cytoskeletal protein important in neural cell migration and adherence. Given our emerging data of reduced vinculin levels in post-infectious rats, molecular mimicry to vinculin may be important to the cause of SIBO and IBS through effects on ICC and ganglia.

Vinculin Expression is Reduced in an Animal Model of Post-Infectious IBS

The inventors assess vinculin expression in the post-infectious rat model.

Methods: Sprague-Dawley rats were divided into 3 groups. Group 1 rats served as controls (n=20). Group 2 rats were gavaged with $10^8$ cfu/mL *C. jejuni* as adults (J−/A+). Group 3 rats were gavaged with *C. jejuni* as juveniles and then again 2 months later a second time as adults. For infected rats, they were euthanized 3 months after clearance of *C. jejuni*. At the time of euthanasia, sections of small bowel (duodenum, jejunum, and ileum) were ligated and contents for total bacterial contents by qPCR as previously described. A segment of mid small bowel was also obtained and retained in RNA later. After homogenizing, extraction of RNA and conversion to cDNA, qPCR was used to determine the level of vinculin in the bowel wall after normalizing for β-actin. The level of vinculin was assessed based on the number of *C. jejuni* infections and the presence or absence of SIBO in this animal model.

Results: Based on normal bacterial levels in the small bowel segments of normal subjects, SIBO was identified in 26% and 46% of rats with single and double exposure to *C. jejuni*. Overall, vinculin expression was reduced in small bowel of rats exposed to *C. jejuni* (0.058±0.0053) compared to control rats (0.087±0.0053) ($P<0.001$). Furthermore, there was a greater reduction of vinculin with two exposures to *C. jejuni* compared to a single exposure (see figure) ($P<0.0001$). There was also a trend to lower vinculin expression in rats with SIBO ($P=0.05$).

Conclusions: Vinculin expression is reduced by exposure to *C. jejuni*. This reduction is dependent on the number of exposures to *C. jejuni* with greater reduction in rats that have been exposed to *C. jejuni* twice. Finally, SIBO is associated with a lower level of vinculin expression. Vinculin may be important in the pathogenesis of post-infectious IBS.

Subjects (18-65 yrs) with Rome positive IBS were recruited from Cedars-Sinai Medical Center and Beth Israel Deaconess Medical Center. Subjects were assessed for symptoms and demographics followed by collection of sera. Subjects were excluded if they had concomitant GI disease, previous GI surgery, adhesions, unstable thyroid disease, diabetes, or HIV. Healthy controls were recruited based on the completion of a GI symptom questionnaire. On this questionnaire, subjects had to have marked <10 for bloating, diarrhea, abdominal pain, and constipation inclusive on a 0-100 VAS. Subjects with inflammatory bowel disease were recruited from an expert tertiary care medical center. Subjects with Crohn's disease or ulcerative colitis were excluded if there was a history of biologic therapy and current prednisone use. Serum from all 3 groups was used to perform and ELISA to determine antibodies to human recombinant vinculin.

In total 165 IBS, 30 IBD and 26 healthy control subjects were evaluated. Demographics were similar between groups. Overall, IBS had a significantly greater optical density in the ELISA for anti-vinculin antibodies compared to IBD and healthy subjects. (FIG. 23) Comparing the two major centers for IBS recruitment, results from both centers were similarly abnormal (P=NS). Interestingly, subjects with a history of acute gastroenteritis, even higher levels of antibodies were seen ($P<0.05$).

Anti-vinculin antibodies are elevated in IBS compared to non-IBS. This is the first diagnostic test for IBS based on serum and a pathophysiologic mechanism of IBS through acute gastroenteritis precipitated molecular mimicry and autoimmunity.

Example 3—Materials and Methods

Subject Groups

For the validation of this serum marker, subjects from a 180 center large scale randomized controlled therapeutic trial in diarrhea-predominant IBS (D-IBS) were recruited (TARGET 3). Subjects with D-IBS were selected based on the presence of Rome III criteria. 6 Healthy controls were recruited from Cedars-Sinai Medical Center and the Beth Israel Deaconess Medical Center. All healthy controls were screened for prior history of gastrointestinal disease and for active gastrointestinal symptoms based on history and completion of a bowel symptom questionnaire Subjects with inflammatory bowel disease (IBD) and celiac disease were recruited based on the presence of intestinal complaints and histologic confirmation of chronic inflammatory changes in the colon or small intestine consistent with Crohn's disease, ulcerative colitis (UC) or celiac disease.

Subjects were excluded from the study if they had a history of diabetes, HIV, unstable thyroid disease, and chronic narcotic use. For IBS subjects and healthy controls, bowel surgery (excluding cholecystectomy or appendectomy) was also an exclusion criteria.

Patient Data

Patient demographics were obtained for all subjects including age and gender. In the case of IBD, the type of disease (UC or Crohn's disease).

Plasma Collection

Plasma was collected from all subjects. This was collected by venipuncture in a lavender top tube, centrifuged at 3500 rpm for 15 minutes and then stored frozen at −80° C. until the time of testing. In the case of the D-IBS subjects from TARGET 3, plasma was collected prior to treatment in the trial.

ELISA Testing

ELISAs were performed using either a complete recombinant *Campylobacter* CdtB protein (Creative Biomart, Shirley, N.Y.) or full length vinculin protein (Novoprotein, Short Hills, N.J.) as antigens at 1.2 µg/ml concentration. Antigens were immobilized overnight at 4° C. onto high-binding 96-well plates (Grenier Bio-One, Monroe, N.C.) in Borate Buffered Saline (BBS) (*Medicago*, Uppsala, Sweden) at a pH of 8.2. Wells were alternately coated with antigen or left uncoated in BBS to allow determination of non-specific binding of plasma. Wells were blocked with 3% bovine serum albumin in 1×PBS for 1 hour at room temperature. Coated and uncoated wells were then incubated with a 1:512 dilution of plasma for CdtB and a 1:32 dilution of plasma for vinculin for 1 hour at room temperature. Antibodies to CdtB and vinculin were used as positive controls. This was followed by 1 hour incubation with HRP conjugated secondary antibodies (Jackson ImmunoResearch, West Grove, Pa.). Each step was followed by a series of washes using 0.05% PBS-Tween 20. Finally, a 3,3',5,5'-Tetramethylbenzidine (TMB) substrate solution (Pierce, Rockford, Ill.) was used for visualization and immediately read on a BioTek Synergy HT plate reader (Winooski, Vt.). The optical densities (OD) were read for 90 minutes at 370 nm and used to compare levels of anti-CdtB or anti-vinculin. Raw OD values were used for the data analysis.

Statistical Analysis (Data w/o Celiac Patients)

Data were expressed as mean±standard error (SE) and exact 95% confidence intervals (CI). Multiple group comparisons were performed using one-way analysis of variance (ANOVA) after equality of variances was confirmed by Bartlett's test. Normality of the data distribution was assessed using histograms with overlapping Kernel density and normal distributions curves. Distribution of anti-vinculin and anti-CdtB normalized after values were transformed to square roots and squares respectively. Student's t-test was used for comparisons of normally distributed variables between two groups. Pearson's chi-squared test was used for comparison of categorical data. Receiver operating characteristic (ROC) curves were constructed using nonparametric methodology. Confidence intervals for areas under curves (AUC) were computed using DeLong's method. Sensitivity, specificity and likelihood ratios of each independent value of anti-vinculin and anti-CdtB to a precision of 0.01 OD were calculated and were assessed to capture the optimal cut-offs. A P value of <0.05 was considered significant. Analysis was performed using STATA version 11.2 (STATA Corp., Texas, USA)

Statistical Analysis (Data w/Celiac Patients)

Numerical variables were summarized by mean±standard deviation. Normality of the data distributions was assessed using histograms with overlapping Kernel density and normal distributions curves. The anti-vinculin distribution was normalized by a square root transformation. Homogeneity of variance was assessed by Bartlett's test.

Student's t-test was used for comparisons of normally distributed variables between two groups. Normally distributed variables were compared across more than two groups by one-way ANOVA and Dunnett's post hoc tests with IBS as the reference group. Categorical variables were summarized by frequency and percent. Pearson's chi-square test was used for comparison of categorical data. Receiver operating characteristic (ROC) curves were constructed in the standard fashion. Confidence intervals for areas under curves (AUC) were computed using the method of DeLong et al 21. Sensitivity, specificity and likelihood ratios of anti-vinculin and anti-CdtB to a precision of 0.01 OD were calculated and were assessed to obtain the favorable cut-offs. The 0.05 significance level was used throughout. Statistical analysis was performed using STATA version 11.2 (STATA Corp., Texas, USA) and SAS version 9.3 (SAS Institute, Cary, N.C., USA).

Example 3—Results

Patient Demographics (w/o Analysis Relating to Celiac Patients)

In total, 2767 subjects were recruited (Table 5A). This included 2564 D-IBS subjects, 43 healthy subjects, 10 celiac and 150 IBD subjects (n=78 Crohn's, 72 ulcerative colitis (UC)). There were significantly more females in the healthy volunteers, IBS and celiac cohorts as compared with the IBD cohort (P=0.01). IBS subjects were on average 6.7 years older than non-IBS subjects (P<0.01). Age was not significantly different between the other groups.

TABLE 5A

Patient demographics.

| | Number of subjects | Age | % of females |
|---|---|---|---|
| Healthy controls | 43 | 36.0 ± 9.9 | 67.4 |
| IBS | 2564 | 46.4 ± 13.6 | 68.2 |
| CD | 78 | 41.8 ± 13.1 | 56.4 |
| UC | 72 | 40.2 ± 12.9 | 55.5 |
| IBD (UC + CD) | 150 | 41.0 ± 13.0 | 56.0 |
| Celiac disease | 10 | 35.6 ± 10.3 | 70 |

Values are given as mean ± SD; OD—optical density; CD—Crohn's disease, UC—ulcerative colitis Patient Demographics (w/Analysis Relating to Celiac Patients)

In total, 2681 subjects were recruited (Table 5B). This included 2375 D-IBS subjects, 43 healthy subjects, 121 celiac and 142 IBD subjects (n=73 Crohn's, n=69 ulcerative colitis). IBS subjects were on average 3.9 years older than the non-IBS groups (p<0.001). There were no differences in sex distribution of IBS and non-IBS subjects; however, percentage of females was greater in the healthy controls, IBS and celiac groups as compared with the IBD group (P<0.001).

TABLE 5B

Patient demographics.

| | Number of subjects | Age (range) | % of females |
|---|---|---|---|
| Healthy controls | 43 | 36.0 ± 9.9 (22-62) | 67.4 |
| D-IBS | 2375 | 44.4 ± 12.2 (18-65) | 67.6 |
| CD | 73 | 40.6 ± 11.3 (18-65) | 56.2 |
| UC | 69 | 41.2 ± 12.2 (19-63) | 55.1 |
| IBD (UC + CD) | 142 | 40.9 ± 11.7 (18-65) | 55.6 |
| Celiac disease | 121 | 41.6 ± 12.3 (19-65) | 76 |

Values are given as mean ± standard deviation, CD—Crohn's disease, UC—ulcerative colitis.

ELISA comparisons between groups (w/o Celiac Patients)

Anti-CdtB levels in IBS subjects were significantly higher than in all non-IBS subjects (2.54±0.01 (95% CI 2.52-2.57) compared to 1.68±0.05 (95% CI 1.58-1.79)) (P<0.001) (FIG. 1A). There were no significant differences in anti-CdtB levels among non-IBS subjects (F-test P=0.25).

Anti-vinculin levels were significantly higher in IBS subjects when compared to all non-IBS subjects (1.3334±0.02 (95% CI 1.30-1.37) compared to 1.01±0.06 (95% CI 0.89-1.12)) (P<0.001) (FIG. 2A). Differences in anti-vinculin levels among non-IBS subjects were not statistically significant (F-test P=0.08).

ELISA Comparisons Between Groups (w/Celiac Patients)

Using optical density levels, anti-CdtB antibody levels in D-IBS subjects (2.53±0.69) were significantly higher than healthy subjects (1.81±0.73), Crohn's disease (1.72±0.81), ulcerative colitis (1.54±0.68) and celiac disease (2.23±0.70) (P<0.001) (FIG. 1B). There were no differences in anti-CdtB levels between healthy subjects and IBD subjects (p=0.23); however, subjects with celiac disease had higher anti-CdtB levels than all other non-IBS groups (p<0.001).

Anti-vinculin levels were also significantly higher in D-IBS subjects (1.34±0.85) when compared to healthy subjects (0.81±0.59), Crohn's disease (1.05±0.91), ulcerative colitis (0.96±0.77) and celiac disease (1.07±0.98) (P<0.0001) (FIG. 1B). Differences in anti-vinculin levels among non-IBS subjects were not statistically significant.

Sensitivity and Specificity Analyses (w/o Celiac Patients)

Receiver operating characteristics (ROC) were used to assess the utility of anti-vinculin and anti-CdtB levels in differentiating IBS subjects from non-IBS, IBD and healthy individuals. FIGS. 3A and 4 demonstrate the ROC curves for these two tests when comparing IBS subjects to all non-IBS subjects and to IBD subjects, respectively. The anti-CdtB test performed better than anti-vinculin and appeared equally discriminating of IBS from all non-IBS subjects and from the IBD group alone. In subgroup analysis, there appeared to be no difference based on the type of IBD (data not shown). The ROC curve for both anti-CdtB and anti-vinculin show that D-IBS can be discriminated from healthy subjects based on this test.

The optical density (OD) levels for each test were then used to determine the ideal threshold for identification of D-IBS. Tables 2A and 3A demonstrate some potential optical density thresholds for the identification of IBS based on sensitivity, specificity and likelihood ratio. For D-IBS, a higher specificity even when associated with a lower sensitivity is more desirable. In D-IBS an ideal test would definitively diagnose IBS, thus reducing the need for invasive testing. So specificity and likelihood ratio was deemed more important. Based on the ROC curves, the ideal level for anti-CdtB appeared to be a level of ≥2.48 and for anti-vinculin the optimal level was of ≥1.62 appear to optimize specificity with relatively limited effects on sensitivity.

TABLE 3A

Favorable cutoffs of anti-CdtB for diagnosis of IBS over other causes

| OD | Specificity % | Sensitivity % | +LR | −LR |
|---|---|---|---|---|
| ≥2.48 | 84.7 | 60.7 | 4.0 | 0.5 |
| ≥2.79 | 91.1 | 44.4 | 5.0 | 0.6 |

OD—optical density, +LR—positive likelihood ratio, −LR—negative likelihood ratio

TABLE 4A

Favorable cutoffs of anti-vinculin for diagnosis of IBS over other causes

| OD | Specificity % | Sensitivity % | +LR | −LR |
|---|---|---|---|---|
| ≥1.62 | 82.3 | 35.0 | 2.0 | 0.78 |
| ≥1.86 | 86.7 | 26.5 | 2.0 | 0.8 |
| ≥2.23 | 92.1 | 15.7 | 2.0 | 0.9 |

OD—optical density, +LR—positive likelihood ratio, −LR—negative likelihood ratio Sensitivity and Specificity Analyses (w/Celiac Patients)

Receiver operating characteristics (ROC) were used to assess the utility of anti-vinculin and anti-CdtB levels in differentiating D-IBS subjects from IBD subjects. FIG. 3B demonstrates the ROC curves for these two tests when comparing D-IBS subjects to IBD subjects. While both tests were effective at discriminating D-IBS subjects from the IBD group, the area-under-the-curve (AUC) for the diagnosis of D-IBS vs. IBD was higher for anti-CdtB than for anti-vinculin (0.81 and 0.62, respectively). In subgroup analysis, there appeared to be no difference based on the type of IBD (data not shown). The ROC curves for D-IBS compared to non-IBS, celiac subjects and healthy controls were also discriminatory.

The optical density (OD) levels for each test were then used to determine the ideal threshold for identification of D-IBS as compared to IBD. Tables 2B and 3B demonstrate some potential optical density thresholds for the identification of D-IBS based on sensitivity, specificity and likelihood ratio. An ideal test would definitively diagnose IBS, thus reducing the need for invasive testing. Therefore, we focused on specificity and positive likelihood ratio. Based on this, the ideal threshold for anti-CdtB to identify D-IBS appeared to be ≥2.80, while for anti-vinculin the optimal threshold appeared to be ≥1.68.

TABLE 3B

Favorable cut offs for anti-CdtB for the diagnosis of D-IBS over IBD

| OD | Specificity % | Sensitivity % | +LR | −LR |
|---|---|---|---|---|
| ≥2.49 | 85.9 | 60.0 | 4.3 | 0.5 |
| ≥2.80 | 91.6 | 43.7 | 5.2 | 0.6 |
| ≥3.04 | 95.8 | 28.3 | 6.7 | 0.7 |

OD—optical density, +LR—positive likelihood ratio, −LR—negative likelihood ratio

TABLE 4B

Favorable cut offs for anti-vinculin for the diagnosis of D-IBS over IBD

| OD | Specificity % | Sensitivity % | +LR | −LR |
|---|---|---|---|---|
| ≥1.53 | 80.3 | 37.8 | 1.9 | 0.8 |
| ≥1.68 | 83.8 | 32.6 | 2.0 | 0.8 |
| ≥1.80 | 84.5 | 28.9 | 1.8 | 0.8 |

OD—optical density, +LR—positive likelihood ratio, −LR—negative likelihood ratio Gender Effect on Biomarker (w/o Celiac Patients)

Anti-CdtB and anti-vinculin levels were also compared in females only and in males only. Despite gender differences between subjects with D-IBS and control groups, both biomarkers could be used to successfully identify D-IBS in both males and females.

Headings used herein are simply for organization and are not intended to limit the disclosure in any manner. The content of any individual section may be equally applicable to all sections.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of detecting the presence or absence of an antibody capable of binding specifically to cytolethal distending toxin (CDT), CdtA, CdtB, CdtC, or a fragment thereof, comprising:
obtaining a biological sample from a subject having a symptom of post-infectious irritable bowel syndrome (PI-IBS);
detecting the presence or absence of an antibody capable of binding specifically to cytolethal distending toxin (CDT), CdtA, CdtB, CdtC, or a fragment thereof in an enzyme-linked immunosorbent assay (ELISA), immunohistochemistry, flow cytometry, a radioimmuno assay, or affinity purification, by contacting CDT, CdtA, CdtB, CdtC, or a fragment thereof, to the biological sample and detecting a signal that indicates the presence of the antibody capable of binding to CDT, CdtA, CdtB, CdtC, or a fragment thereof.

2. The method of claim 1, comprising contacting CdtB or the fragment thereof to the biological sample obtained from the subject.

3. The method of claim 1, comprising contacting CdtB of *Campylobacter jejuni* or the fragment thereof to the biological sample obtained from the subject.

4. The method of claim 3, wherein the CdtB of *Campylobacter jejuni* has an amino acid sequence at least 80% identical to SEQ ID NO:5.

5. The method of claim 3, wherein CdtB of *Campylobacter jejuni* has an amino acid sequence as set forth in SEQ ID NO:5.

6. The method of claim 1, wherein the antibody is capable of binding specifically to an epitope on 5 to 22 contiguous residues of SEQ ID NO:5.

7. The method of claim 6, wherein the epitope is on 17 contiguous residues as disclosed by SEQ ID NO:3.

8. The method of claim 1, wherein the antibody is capable of binding specifically to an epitope on SEQ ID NO:4.

9. The method of claim 1, comprising contacting CdtB of *Campylobacter coli* or the fragment thereof to the biological sample obtained from the subject.

10. The method of claim 9, wherein the CdtB of *Campylobacter coli* has an amino acid sequence at least 80% identical to SEQ ID NO:1.

11. The method of claim 9, wherein the CdtB of *Campylobacter coli* has an amino acid sequence as set forth in SEQ ID NO:1.

12. The method of claim 1, wherein the CdtB is CdtB of *Escherichia coli*, *Salmonella*, *Shigella* or *Clostridium difficile*.

13. The method of claim 1, wherein the biological sample is whole blood, plasma or serum.

14. The method of claim 1, further comprising directing the subject to a SIBO treatment when the presence of the antibody capable of binding specifically to CDT, CdtA, CdtB, CdtC, or the fragment thereof is detected.

15. The method of claim 1, wherein the subject having the PI-IBS is a human subject.

16. A method of detecting the presence or absence of an antibody capable of binding specifically to cytolethal distending toxin B (CdtB) of *Campylobacter jejuni* or a fragment thereof, comprising:
   obtaining whole blood, plasma or serum from a subject having a symptom of post-infectious irritable bowel syndrome (PI-IBS);
   detecting the presence or absence of an antibody capable of binding specifically to cytolethal distending toxin B (CdtB) of *Campylobacter jejuni* or a fragment thereof in an enzyme-linked immunosorbent assay (ELISA) by contacting CdtB of *Campylobacter jejuni* or a fragment thereof to the whole blood, plasma or serum and detecting a signal that indicates the presence of the antibody capable of binding to CdtB of *Campylobacter jejuni* or the fragment thereof.

17. The method of claim 16, further comprising directing the subject to a PI-IBS treatment when the presence of the antibody capable of binding specifically CdtB or the fragment thereof is detected.

18. The method of claim 16, further comprising administering to the subject a PI-IBS treatment when the presence of the antibody capable of binding specifically CdtB or the fragment thereof is detected.

* * * * *